US010598671B2

(12) United States Patent
Heath et al.

(10) Patent No.: US 10,598,671 B2
(45) Date of Patent: Mar. 24, 2020

(54) IL-17F-SPECIFIC CAPTURE AGENTS, COMPOSITIONS, AND METHODS OF USING AND MAKING

(71) Applicants: California Institute of Technology, Pasadena, CA (US); Indi Molecular, Inc., Culver City, CA (US)

(72) Inventors: James R. Heath, South Pasadena, CA (US); Heather Agnew, Culver City, CA (US); Blake Farrow, Pasadena, CA (US); David Bunck, Pasadena, CA (US); Jingxin Liang, Pasadena, CA (US); Arundhati Nag, Pasadena, CA (US); Samir Das, Pasadena, CA (US); Bert Tsunyin Lai, Culver City, CA (US); Suresh Mark Pitram, La Jolla, CA (US)

(73) Assignees: Indi Molecular, Inc., Culver City, CA (US); California Institute of Technology, Pasadena, CA (US)

( * ) Notice: Subject to any disclaimer, the term of this patent is extended or adjusted under 35 U.S.C. 154(b) by 115 days.

(21) Appl. No.: 15/211,759

(22) Filed: Jul. 15, 2016

(65) Prior Publication Data

US 2017/0052199 A1 Feb. 23, 2017

Related U.S. Application Data

(60) Provisional application No. 62/309,756, filed on Mar. 17, 2016, provisional application No. 62/277,430, filed on Jan. 11, 2016, provisional application No. 62/192,899, filed on Jul. 15, 2015.

(51) Int. Cl.

| | |
|---|---|
| ***G01N 33/68*** | (2006.01) |
| ***C07K 7/64*** | (2006.01) |
| ***C07K 14/54*** | (2006.01) |
| ***C07K 7/06*** | (2006.01) |

(52) U.S. Cl.

CPC ........... *G01N 33/6869* (2013.01); *C07K 7/06* (2013.01); *C07K 7/64* (2013.01); *C07K 14/54* (2013.01); *C07K 2319/00* (2013.01); *G01N 2333/54* (2013.01)

(58) Field of Classification Search

CPC . C07K 7/64; C07K 14/54; C07K 7/06; C07K 2319/00; G01N 33/6869; G01N 2333/54

See application file for complete search history.

(56) References Cited

U.S. PATENT DOCUMENTS

| | | | |
|---|---|---|---|
| 4,899,755 | A | 2/1990 | Lauffer et al. |
| 5,021,556 | A | 6/1991 | Srinivasan |
| 5,075,099 | A | 12/1991 | Srinivasan et al. |
| 5,118,797 | A | 6/1992 | Jurisson et al. |
| 5,183,653 | A | 2/1993 | Linder et al. |
| 5,364,613 | A | 11/1994 | Sieving et al. |
| 5,367,080 | A | 11/1994 | Toner et al. |
| 5,387,409 | A | 2/1995 | Nunn et al. |
| 5,474,756 | A | 12/1995 | Tweedle et al. |
| 5,608,110 | A | 3/1997 | Ramalingam et al. |
| 5,656,254 | A | 8/1997 | Ramalingam et al. |
| 5,662,885 | A | 9/1997 | Pollak et al. |
| 5,665,329 | A | 9/1997 | Ramalingam et al. |
| 5,688,487 | A | 11/1997 | Linder et al. |
| 5,720,934 | A | 2/1998 | Dean et al. |
| 5,780,006 | A | 7/1998 | Pollak et al. |
| 5,846,519 | A | 12/1998 | Tweedle et al. |
| 5,849,261 | A | 12/1998 | Dean et al. |
| 5,879,658 | A | 3/1999 | Dean et al. |
| 5,886,142 | A | 3/1999 | Thakur et al. |
| 5,976,495 | A | 11/1999 | Pollak et al. |
| 6,093,382 | A | 7/2000 | Wedeking et al. |
| 6,143,274 | A | 11/2000 | Tweedle et al. |
| 2006/0153839 | A1 | 7/2006 | Mohamed et al. |
| 2010/0009896 | A1 | 1/2010 | Agnew et al. |
| 2011/0263515 | A1 | 10/2011 | Agnew et al. |
| 2015/0132314 | A1 | 5/2015 | Masternak et al. |

FOREIGN PATENT DOCUMENTS

| | | | |
|---|---|---|---|
| WO | 1986/006605 | A1 | 11/1986 |
| WO | 1991/003200 | A1 | 3/1991 |
| WO | 1995/003280 | A1 | 2/1995 |
| WO | 1995/006633 | A1 | 3/1995 |
| WO | 1995/028179 | A1 | 10/1995 |
| WO | 1995/028967 | A1 | 11/1995 |
| WO | 1996/023526 | A2 | 8/1996 |
| WO | 1997/036619 | A2 | 10/1997 |
| WO | 1998/018496 | A2 | 5/1998 |
| WO | 1998/018497 | A2 | 5/1998 |
| WO | 1998/046612 | A1 | 10/1998 |
| WO | 1998/052618 | A1 | 11/1998 |
| WO | 1999/017809 | A2 | 4/1999 |
| WO | 2012/106671 | A1 | 8/2012 |

(Continued)

OTHER PUBLICATIONS

Alexander et al. (1998) "Intracranial black-blood MR angiography with high-resolution 3D fast spin echo," Magn. Reson. Med. 40:298-310.

Altschul et al. (1997) "Gapped BLAST and PSI-BLAST: a new generation of protein database search programs," Nucleic Acids Res. 25:3389-3402.

Bundgaard (1985) Design of Prodrugs. Elsevier Science Pub. Co. pp. 7-9, 21-24.

Claverie et al. (1993) "Information enhancement methods for large scale sequence analysis," Comput. Chem. 17(3):191-201.

Das et al. (Sep. 17, 2015) "A General Synthetic Approach for Designing Epitope Targeted Macrocyclic Peptide Ligands," Angew. Chem. Int. Ed. 54(45):13219-13224.

(Continued)

*Primary Examiner* — Shafiqul Haq

(74) *Attorney, Agent, or Firm* — Pabst Patent Group LLP

(57) ABSTRACT

The present application provides stable peptide-based IL-17F capture agents and methods of use as detection agents. The application further provides methods of manufacturing IL-17F capture agents.

50 Claims, 18 Drawing Sheets

Specification includes a Sequence Listing.

(56) References Cited

FOREIGN PATENT DOCUMENTS

| | | | |
|---|---|---|---|
| WO | 2013/009869 | A2 | 1/2013 |
| WO | 2013/033561 | A1 | 3/2013 |
| WO | 2014/074907 | A1 | 5/2014 |

OTHER PUBLICATIONS

Edelman et al. (1990) "Extracranial carotid arteries: evaluation with 'black blood' MR angiography," Radiology. 177(1):45-50.

Goodrich et al. (1996) "A Quantitative Study of Ramped Radio Frequency, Magnetization Transfer, and Slab Thickness in Three-Dimensional Time-of-Flight Magnetic Resonance Angiography in a Patient Population," Invest. Radial. 31(6)323-32.

Iwata et al. (Jan. 2000) "A new, convenient method for the preparation of 4-[18F]fluorobenzyl halides," Applied Radiation and Isotopes. 52(1):87-92.

Liu et al. (Jul. 1999) "99mTc-Labeled Small Peptides as Diagnostic Radiopharmaceuticals" Chem. Rev. 99:9.2235-2.

Myers et al. (1988) "Optimal Alignments in Linear Space," CABIOS. 4:11-17.

Poethko et al. (May 1, 2004) "Two-Step Methodology for High-Yield Routine Radiohalogenation of Peptides: 18F-Labeled RGD and Octreotide Analogs," The Journal of Nuclear Medicine. 45(5):892-902.

Schottelius et al. (Jun. 1, 2004) "First 18F-Labeled Tracer Suitable for Routine Clinical Imaging of sst Receptor-Expressing Tumors Using Positron Emission Tomography," Clinical Cancer Research, 10(11):3593-3606.

Wilson et al. (1990) "Reductive amination of [18F]fluorobenzaldehydes: Radiosyntheses of [2-18F]- and [4-18F] fluorodexetimides" Journal of Labeled Compounds and Radiopharmaceuticals. XXVIII(10):1189-1199.

Wootton et al. (Jun. 1993) "Statistics of local complexity in amino acid sequences and sequence databases," Comput. Chem. 17(2):149-63.

International Search Report and Written Opinion for PCT/US2016/042558 dated Jan. 23, 2017, 20 pp.

Coppock et al., "Peptide-based protein capture agents with high affinity, selectivity, and stability as antibody replacements in biodetection assays," Optical Sensing I, vol. 9107, May 22, 2014, 6 pp.

Millward et al. "In situ click chemistry: from small molecule discovery to synthetic antibodies," Integrative Biology, vol. 5, No. 1, Jan. 1, 2013, 17 pp.

Das et al., "A General Synthetic Approach for Designing Epitope Targeted Macrocyclic Peptide Ligands," Angewandte Chemie International Edition, vol. 54, No. 45, Nov. 2, 2015, 7 pp.

Zhang et al., "Function of interleukin-17 familycytokines," Protein & Cell, vol. 2, No. 1, Feb. 20, 2011, 16 pp.

Biotin-PEG$_3$-FFQKPES[Az4]PPVPGGS (amino acids 40-54)

Biotin-PEG$_3$-GI[Az4]NENQRVS (amino acids 60-69)

```
IL-17A:    IVKAGITIPRNP.GCPNSEDKNFPRTVMVNLNIHNRNTNTN..PKRSSDYYNRST
IL-17F:    RKIPKVGHTFFQKPESCPPVPGG........SMKLDIGIINENQRVSMSRNIESRST
Epitope1:             FFQKPESXPPVPGG........S
Epitope2:                                       GIXNENQRVS
```
X = Az4 substitution (click handle)

1) $His_6$-$PEG_3$-FFQKPESSPPVPGGS
2) $His_6$-$PEG_3$-FFQKPESS*PVSPGPG* (scrambled C-terminal to click handle)
3) $His_6$-$PEG_3$-*SQFEKFP*SPPVPGGS (scrambled N-terminal to click handle)

Chemical Formula: $C_{88}H_{143}N_{35}O_{24}S$
Exact Mass: 2106.08
Molecular Weight: 2107.36

Chemical Formula: $C_{90}H_{147}N_{35}O_{25}S$
Exact Mass: 2150.10
Molecular Weight: 2151.41

Chemical Formula: $C_{92}H_{151}N_{35}O_{26}S$
Exact Mass: 2194.13
Molecular Weight: 2195.47

Chemical Formula: $C_{94}H_{155}N_{35}O_{27}S$
Exact Mass: 2238.16
Molecular Weight: 2239.52

Chemical Formula: $C_{96}H_{159}N_{35}O_{28}S$
Exact Mass: 2282.18
Molecular Weight: 2283.57

Chemical Formula: $C_{98}H_{163}N_{35}O_{29}S$
Exact Mass: 2326.21
Molecular Weight: 2327.62

```
                                                            *
IL-17F  .........  .........  .........  ...RKIPKVG HTFFQKPEG   17
IL-17A  .........  .........  .........  ...IVRAG  ITIPRNF.G   14

                          0                    ⊂⊃        1
IL-17F  PPVPGG....  ....SHRLDI  GIINENQRVS  HSRNIESRST  PWNYTVTWD   59
IL-17A  PNSEDKNFPR  TVMVNLNIHN  RNTNTN..PK  RSSDYYNRST  PWNLHRNED   62

                   2                          3
IL-17F  PNRYPSEVVQ  AQ RNLG IN  A..QGKEDIS  MN VPI.QQE  TLVVRBKHQG  106
IL-17A  PERYPSVIWE  AK RHLG IN  A..DGNVDYH  MN VPI.QQE  ILVLRREPPH  109

         *                    4
IL-17F  SV........  ....SPQLEK  VL..VTVG T  VTPVIHHVQ  ...          133
IL-17A  PN........  ....SFRLEK  IL..VSVG T  VTPIVHHVA  ...          136
```

in IL-17F, the distance between PCCs binding to Epitope 1 and 2 is ~15 Å

Chemical Formula: $C_{94}H_{154}N_{36}O_{27}S$
Exact Mass: 2251.15
Molecular Weight: 2252.52

Chemical Formula: $C_{96}H_{158}N_{36}O_{28}S$
Exact Mass: 2295.18
Molecular Weight: 2296.57

Chemical Formula: $C_{98}H_{162}N_{36}O_{29}S$
Exact Mass: 2339.20
Molecular Weight: 2340.62

Chemical Formula: $C_{100}H_{166}N_{36}O_{30}S$
Exact Mass: 2383.23
Molecular Weight: 2384.68

Chemical Formula: $C_{102}H_{170}N_{36}O_{31}S$
Exact Mass: 2427.26
Molecular Weight: 2428.73

FIG. 14

Pf.HRP-2 sequence. Repeat motifs, many of which were converted into SynEps for screening, are show in different colors MVSFSKNKVLSAAVFASVLLLDNNNSAFNNNLCSKNAKGLNLNKRL
LHETQAHVDDAHHAHHVADAHHAHHAADAHHAHHAADAHHA
HHAADAHHAHHAADAHHAHHAAYAHHAHHAADAHHAHHASD
AHHAADAHHAAYAHHAHHAADAHHAHHASDAHHAADAHHAAY
AHHAHHAADAHHAADAHHATDAHHAHHAADARHATDAHHAAD
AHHATDAHHAADAHHAADAHHATDAHHAADAHHATDAHHAAD
AHHAADAHHATDAHHAHHAADAHHAAAHHATDAHHATDAHHA
AAHHEAATHCLRH cy(YKYYR)-link-cy(YKYYR)

Chemical Formula: $C_{130}H_{188}N_{34}O_{30}S$
Exact Mass: 2737.40
Molecular Weight: 2739.20 cy(YKYYR)-linker-cy(GWNVDL) biligand with linker developed through library screening

SEQUENCE LISTING

```
<160> NUMBER OF SEQ ID NOS: 42

<210> SEQ ID NO 1
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 1

Phe Phe Gln Lys Pro Glu Ser
1               5


<210> SEQ ID NO 2
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 2

Phe Phe Gln Lys Pro Glu Ser Cys Pro Pro Val Pro Gly Gly
1               5                   10


<210> SEQ ID NO 3
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 3

Asn Glu Asn Gln Arg Val Ser
1               5


<210> SEQ ID NO 4
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 4

Gly Ile Ile Asn Glu Asn Gln Arg Val Ser
1               5                   10


<210> SEQ ID NO 5
```

<211> LENGTH: 5
<212> TYPE: PRT
<213> ORGANISM: Artificial Sequence
<220> FEATURE:
<223> OTHER INFORMATION: Synthetic Peptide

<400> SEQUENCE: 5

Phe Tyr Lys Thr His
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 6

Phe Tyr Lys Gln His
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 7

Phe Tyr Leu Thr His
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 8

Phe Tyr Leu Gln His
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 9

Arg Arg Ala Thr Ser
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 10

Arg Arg Ala Gln Ser
1               5

<210> SEQ ID NO 11
<211> LENGTH: 5

-continued

<212> TYPE: PRT
<213> ORGANISM: Artificial Sequence
<220> FEATURE:
<223> OTHER INFORMATION: Synthetic Peptide

<400> SEQUENCE: 11

Lys Tyr Gly Glu Val
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 12

Leu Tyr Gly Glu Val
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 13

Val His Lys Ser Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 14

Val His Leu Ser Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 15

Gln Lys His Gly Pro
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 16

Thr Lys His Gly Pro
1               5

<210> SEQ ID NO 17
<211> LENGTH: 5
<212> TYPE: PRT

<213> ORGANISM: Artificial Sequence
<220> FEATURE:
<223> OTHER INFORMATION: Synthetic Peptide

<400> SEQUENCE: 17

Gln Leu His Gly Pro
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 18

Thr Leu His Gly Pro
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 19

Tyr Asp Leu Gln Arg
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 20

Tyr Asp Leu Thr Arg
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 21

Tyr Asp Lys Gln Arg
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 22

Tyr Asp Lys Thr Arg
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 23

Lys Lys Gly Trp Pro
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 24

Lys Leu Gly Trp Pro
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 25

Leu Lys Gly Trp Pro
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 26

Leu Leu Gly Trp Pro
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 27

Arg Ser Tyr Asn Leu
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 28

Arg Ser Tyr Asn Lys
1               5

<210> SEQ ID NO 29
<211> LENGTH: 5
<212> TYPE: PRT
<213> ORGANISM: Artificial Sequence
<220> FEATURE:

<223> OTHER INFORMATION: Synthetic Peptide

<400> SEQUENCE: 29

Tyr Lys Tyr Tyr Arg
1 5

<210> SEQ ID NO 30
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 30

Gly Trp Asn Val Asp Leu
1 5

<210> SEQ ID NO 31
<211> LENGTH: 163
<212> TYPE: PRT
<213> ORGANISM: Homo sapiens

<400> SEQUENCE: 31

Met Thr Val Lys Thr Leu His Gly Pro Ala Met Val Lys Tyr Leu Leu
1 5 10 15

Leu Ser Ile Leu Gly Leu Ala Phe Leu Ser Glu Ala Ala Ala Arg Lys
20 25 30

Ile Pro Lys Val Gly His Thr Phe Phe Gln Lys Pro Glu Ser Cys Pro
35 40 45

Pro Val Pro Gly Gly Ser Met Lys Leu Asp Ile Gly Ile Ile Asn Glu
50 55 60

Asn Gln Arg Val Ser Met Ser Arg Asn Ile Glu Ser Arg Ser Thr Ser
65 70 75 80

Pro Trp Asn Tyr Thr Val Thr Trp Asp Pro Asn Arg Tyr Pro Ser Glu
85 90 95

Val Val Gln Ala Gln Cys Arg Asn Leu Gly Cys Ile Asn Ala Gln Gly
100 105 110

Lys Glu Asp Ile Ser Met Asn Ser Val Pro Ile Gln Gln Glu Thr Leu
115 120 125

Val Val Arg Arg Lys His Gln Gly Cys Ser Val Ser Phe Gln Leu Glu
130 135 140

Lys Val Leu Val Thr Val Gly Cys Thr Cys Val Thr Pro Val Ile His
145 150 155 160

Arg Val Gln

<210> SEQ ID NO 32
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 32

Pro Pro Val Pro Gly Gly Ser
1 5

<210> SEQ ID NO 33
<211> LENGTH: 12
<212> TYPE: PRT
<213> ORGANISM: Artificial Sequence
<220> FEATURE:

```
<223> OTHER INFORMATION: Synthetic Peptide
<220> FEATURE:
<221> NAME/KEY: MISC_FEATURE
<222> LOCATION: (1)..(1)
<223> OTHER INFORMATION: Biotin
<220> FEATURE:
<221> NAME/KEY: MISC_FEATURE
<222> LOCATION: (2)..(2)
<223> OTHER INFORMATION: PEG3
<220> FEATURE:
<221> NAME/KEY: MISC_FEATURE
<222> LOCATION: (5)..(5)
<223> OTHER INFORMATION: L-azidolysine

<400> SEQUENCE: 33

Xaa Xaa Gly Ile Xaa Asn Glu Asn Gln Arg Val Ser
1               5                   10


<210> SEQ ID NO 34
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Amidogen
<220> FEATURE:
<221> NAME/KEY: MISC_FEATURE
<222> LOCATION: (2)..(2)
<223> OTHER INFORMATION: L-propargylglycine
<220> FEATURE:
<221> NAME/KEY: MISC_FEATURE
<222> LOCATION: (3)..(7)
<223> OTHER INFORMATION: any of seventeen L-amino acids (excluding Cys,
      Met, and Ile)
<220> FEATURE:
<221> NAME/KEY: MISC_FEATURE
<222> LOCATION: (3)..(7)
<223> OTHER INFORMATION: triazole cyclization
<220> FEATURE:
<221> NAME/KEY: MISC_FEATURE
<222> LOCATION: (9)..(9)
<223> OTHER INFORMATION: TentaGel S NH2 resin

<400> SEQUENCE: 34

Xaa Xaa Xaa Xaa Xaa Xaa Xaa Met Xaa
1               5


<210> SEQ ID NO 35
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 35

Ala His His Ala His His Ala Ala Asp
1               5


<210> SEQ ID NO 36
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 36

Ala His His Ala Thr Asp Ala His His Ala Ala Ala His His Glu Ala
1               5                   10                  15
```

```
Ala Thr His Cys Leu
            20


<210> SEQ ID NO 37
<211> LENGTH: 155
<212> TYPE: PRT
<213> ORGANISM: Homo sapiens

<400> SEQUENCE: 37

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
        35                  40                  45

Leu Asn Ile His Asn Arg Asn Thr Asn Thr Asn Pro Lys Arg Ser Ser
    50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155


<210> SEQ ID NO 38
<211> LENGTH: 163
<212> TYPE: PRT
<213> ORGANISM: Homo sapiens

<400> SEQUENCE: 38

Met Thr Val Lys Thr Leu His Gly Pro Ala Met Val Lys Tyr Leu Leu
1               5                   10                  15

Leu Ser Ile Leu Gly Leu Ala Phe Leu Ser Glu Ala Ala Ala Arg Lys
            20                  25                  30

Ile Pro Lys Val Gly His Thr Phe Phe Gln Lys Pro Glu Ser Cys Pro
        35                  40                  45

Pro Val Pro Gly Gly Ser Met Lys Leu Asp Ile Gly Ile Ile Asn Glu
    50                  55                  60

Asn Gln Arg Val Ser Met Ser Arg Asn Ile Glu Ser Arg Ser Thr Ser
65                  70                  75                  80

Pro Trp Asn Tyr Thr Val Thr Trp Asp Pro Asn Arg Tyr Pro Ser Glu
                85                  90                  95

Val Val Gln Ala Gln Cys Arg Asn Leu Gly Cys Ile Asn Ala Gln Gly
            100                 105                 110

Lys Glu Asp Ile Ser Met Asn Ser Val Pro Ile Gln Gln Glu Thr Leu
        115                 120                 125

Val Val Arg Arg Lys His Gln Gly Cys Ser Val Ser Phe Gln Leu Glu
    130                 135                 140

Lys Val Leu Val Thr Val Gly Cys Thr Cys Val Thr Pro Val Ile His
145                 150                 155                 160
```

His Val Gln

<210> SEQ ID NO 39
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 39

Phe Phe Gln Lys Pro Glu Ser Ser Pro Pro Val Pro Gly Gly Ser
1 5 10 15

<210> SEQ ID NO 40
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 40

Phe Phe Gln Lys Pro Glu Ser Ser Pro Val Ser Pro Gly Pro Gly
1 5 10 15

<210> SEQ ID NO 41
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 41

Ser Gln Phe Glu Lys Phe Pro Ser Pro Pro Val Pro Gly Gly Ser
1 5 10 15

<210> SEQ ID NO 42
<211> LENGTH: 309
<212> TYPE: PRT
<213> ORGANISM: Plasmodium falciparum

<400> SEQUENCE: 42

Met Val Ser Phe Ser Lys Asn Lys Val Leu Ser Ala Ala Val Phe Ala
1 5 10 15

Ser Val Leu Leu Leu Asp Asn Asn Asn Ser Ala Phe Asn Asn Asn Leu
20 25 30

Cys Ser Lys Asn Ala Lys Gly Leu Asn Leu Asn Lys Arg Leu Leu His
35 40 45

Glu Thr Gln Ala His Val Asp Asp Ala His His Ala His His Val Ala
50 55 60

Asp Ala His His Ala His His Ala Ala Asp Ala His His Ala His His
65 70 75 80

Ala Ala Asp Ala His His Ala His His Ala Ala Asp Ala His His Ala
85 90 95

His His Ala Ala Asp Ala His His Ala His His Ala Ala Tyr Ala His
100 105 110

His Ala His His Ala Ala Asp Ala His His Ala His His Ala Ser Asp
115 120 125

Ala His His Ala Ala Asp Ala His His Ala Ala Tyr Ala His His Ala
130 135 140

His His Ala Ala Asp Ala His His Ala His His Ala Ser Asp Ala His
145 150 155 160

-continued

```
His Ala Ala Asp Ala His His Ala Ala Tyr Ala His His Ala His His
                165                 170                 175

Ala Ala Asp Ala His His Ala Ala Asp Ala His His Ala Thr Asp Ala
            180                 185                 190

His His Ala His His Ala Ala Asp Ala Arg His Ala Thr Asp Ala His
        195                 200                 205

His Ala Ala Asp Ala His His Ala Thr Asp Ala His His Ala Ala Asp
    210                 215                 220

Ala His His Ala Ala Asp Ala His His Ala Thr Asp Ala His His Ala
225                 230                 235                 240

Ala Asp Ala His His Ala Thr Asp Ala His His Ala Ala Asp Ala His
                245                 250                 255

His Ala Ala Asp Ala His His Ala Thr Asp Ala His His Ala His His
            260                 265                 270

Ala Ala Asp Ala His His Ala Ala Ala His His Ala Thr Asp Ala His
        275                 280                 285

His Ala Thr Asp Ala His His Ala Ala Ala His His Glu Ala Ala Thr
    290                 295                 300

His Cys Leu Arg His
305
```

IL-17F-SPECIFIC CAPTURE AGENTS, COMPOSITIONS, AND METHODS OF USING AND MAKING

RELATED APPLICATIONS

This application claims priority from U.S. Provisional Patent Application No. 62/192,899, filed on Jul. 15, 2015; U.S. Provisional Patent Application No. 62/277,430, filed on Jan. 11, 2016; and U.S. Provisional Patent Application No. 62/309,756, filed on Mar. 17, 2016, each of which is incorporated herein by reference in its entirety.

BACKGROUND

Human interleukin-17 (IL-17A) is a pro-inflammatory cytokine secreted by activated T-cells. IL-17A is a validated target for treatment of severe plaque psoriasis. There are six different homodimeric cytokines (IL-17A-F) and the heterodimer IL-17A/F in the IL-17 cytokine family. IL-17F is the closest homologue to IL-17A and is 50% identical in sequence. IL-17A and IL-17F are secreted both as disulfide-linked homodimers (32-38 kDa) and as the IL-17A/F covalent heterodimer (40-45 kDa). Like IL-17A, IL-17F activates immune and non-immune cells to induce pro-inflammatory mediators. These mediators can induce neutrophil recruitment at inflammatory sites, promote local tissue destruction, induce neovascularization in tumors, enhance osteoclastogenesis, and protect from pathogen infection, resulting in disease development and host protection.

IL-17A is a validated target for treatment of severe plaque psoriasis. The current approach is to block IL-17A interaction with its receptor at the cell surface by neutralizing circulating IL-17A. This is done primarily through monoclonal antibodies and fragments thereof.

IL-17 cytokine family members mediate their effects through binding to the IL-17 receptor family, of which there are five related members (IL-17RA-IL-17RE). Both IL-17A and IL-17F bind as homodimers or heterodimers to the heterodimeric receptor complex formed between IL-17RA and IL-17RC. While the activity of IL-17F appears to be related to that of IL-17A, the potency differs, consistent with differences in receptor binding affinities.

Because of their roles in immunity and immune-mediated diseases, IL-17A and IL-17F have become an area of focus in therapeutic drug development. The very low natural abundance of circulating IL-17A and IL-17A/F has been a challenge for detecting these biomarkers by traditional sandwich immunoassays. Highly sensitive detection of the circulating levels of each homodimer (IL17A, IL-17F), as well as the IL-17A/F heterodimer, would be informative for understanding the involvement of each cytokine over the course of disease and treatment.

SUMMARY

The present disclosure relates to chemically synthesized capture agents (called protein-catalyzed capture agents, or PCC Agents) that are designed to bind to detect interleukin 17F (IL-17F), methods for making said capture agents using iterative in situ click chemistry, methods for using said capture agents to detect IL-17F, and assays employing said methods.

In one aspect, provided herein is a stable, synthetic capture agent that specifically binds IL-17F, wherein the capture agent comprises one or more designed anchor ligands. In certain embodiments, the capture agent comprises two anchor ligands joined by a linker. In another aspect, provided herein is a composition comprising one or more synthetic capture agents, as described herein, that specifically bind IL-17F. According to certain embodiments, the capture agent binds IL-17F with a greater affinity than IL-17A. According to certain embodiments, the capture agent binds IL-17F with at least 0.25, 0.5, 1, 2, 3, 4, 5, 6, 7, 8, 9, 10, 100 or 1000 greater affinity than IL-17A.

In another aspect, provided herein is a stable, synthetic capture agent that specifically binds IL-17F, wherein the capture agent comprises a first ligand having affinity for a first epitope on IL-17F, a second ligand having affinity for a second epitope on IL-17F, and a linker covalently connecting the first ligand to the second ligand. Particularly, the first ligand binds the first epitope (or a synthetic version thereof) in isolation and the second ligand binds the second epitope (or a synthetic version thereof) in isolation. In the capture agent, the first ligand and the second ligand cooperatively bind the first and second epitopes of IL-17F, respectively.

In another aspect, provided herein is a method for detecting IL-17F in a biological sample, comprising the step of treating the biological sample with one or more capture agents described herein.

Anchor Ligand

In one embodiment of the capture agent, the capture agent comprises two ligands that specifically bind IL-17F at two distinct epitopes. These anchor ligands (sometimes referred to herein as simply "ligands") can then be bound to each other by a linker that provides increased affinity for IL-17F. In certain embodiments, there is a first ligand and a second ligand that bind to a first epitope and a second epitope, respectively.

According to certain embodiments, the first epitope comprises the amino acid sequence of FFQKPES (SEQ ID NO:1) or FFQKPESCPPVPGG (SEQ ID NO:2). In certain embodiments, the first epitope is between 5 and 20 amino acids long. In other embodiments, the first epitope is between 7 and 13 amino acids long. In other embodiments, the first epitope is at most, 5, 6, 7, 8, 9, 10, 11, 12, 13, 14, 15, 16, 17, 18, 19 or 20 amino acids long.

According to certain embodiments, the first epitope comprises the amino acid sequence of NENQRVS (SEQ ID NO:3) or GIINENQRVS (SEQ ID NO:4). In certain embodiments, the first epitope is between 5 and 20 amino acids long. In other embodiments, the first epitope is between 7 and 10 amino acids long. In other embodiments, the first epitope is at most, 5, 6, 7, 8, 9, 10, 11, 12, 13, 14, 15, 16, 17, 18, 19 or 20 amino acids long.

According to certain embodiments, the first ligand comprises an amino acid sequence selected from FYKTH (SEQ ID NO:5), FYKQH (SEQ ID NO:6), FYLTH (SEQ ID NO:7), FYLQH (SEQ ID NO:8), RRATS (SEQ ID NO:9) and RRAQS (SEQ ID NO:10). According to certain embodiments, the first ligand comprises an amino acid sequence selected from RRATS (SEQ ID NO:9) and RRAQS (SEQ ID NO:10). In certain embodiments, the first ligand is cyclic. In certain embodiments, the first ligand comprises a 1,4-substituted-1,2,3-triazole residue (Tz4) or a 1,5-substituted-1,2,3-triazole residue (Tz5).

According to certain embodiments, the first ligand comprises an amino acid sequence selected from KYGEV (SEQ ID NO:11), LYGEV (SEQ ID NO:12), VHKSG (SEQ ID NO:13), VHLSG (SEQ ID NO:14), QKHGP (SEQ ID NO:15), TKHGP (SEQ ID NO:16), QLHGP (SEQ ID NO:17), TLHGP (SEQ ID NO:18), YDLQR (SEQ ID NO:19), YDLTR (SEQ ID NO:20), YDKQR (SEQ ID NO:21), YDKTR (SEQ ID NO:22), KKGWP (SEQ ID NO:23), KLGWP (SEQ ID NO:24), LKGWP (SEQ ID NO:25), LLGWP (SEQ ID NO:26), RSYNL (SEQ ID NO:27), and RSYNK (SEQ ID NO:28). According to certain embodiments, the first ligand comprises an amino acid sequence selected from TKHGP (SEQ ID NO:16), QKHGP (SEQ ID NO:15), KKGWP (SEQ ID NO:23) and RSYNK (SEQ ID NO:28). In certain embodiments, the first ligand is cyclic. In certain embodiments, the first ligand comprises a 1,4-substituted-1,2,3-triazole residue (Tz4) or a 1,5-substituted-1,2,3-triazole residue (Tz5).

According to certain embodiments, the first ligand comprises the sequence RRATS (SEQ ID NO:9) and the second ligand comprises the sequence QKHGP (SEQ ID NO:15). In other embodiments, the first ligand comprises the sequence RRATS (SEQ ID NO:9) and the second ligand comprises the sequence RSYNK (SEQ ID NO:28). In other embodiments, the first and second ligands are cyclic and comprise a Tz4 residue.

Linker

According to certain embodiments, the capture agent further comprises a linker that binds both the first and second ligand. According to certain embodiments, the length of the linker corresponds to distance between the first epitope and the second epitope. The length of the linker must be at least the distance between the first and second epitopes. In certain embodiments, the linker is longer than the distance between the first and second epitopes. According to certain embodiments, the linker is 1, 2, 3, 4, 5, 6, 7, 8, 9, 10, 20, 30, 40, 50, 60, 70, 80, 90 or 100% longer than the distance between the first and second epitopes.

According to certain embodiments, the linker is ~4.4 Å to ~26.4 Å, ~8.8 Å to ~26.4 Å or ~7 Å to ~15 Å in length. In certain embodiments, the length of the linker is ~15 Å.

In other embodiments, the linker comprises one or more repeat units of ethylene glycol. In some embodiments, the linker is $PEG_1$, $PEG_2$, $PEG_3$, $PEG_4$, or $PEG_5$. In other embodiments, the linker comprises a peptide. In other embodiments, the linker comprises an amino acid. In a particular embodiment, the linker is glycine. In other embodiments, the linker comprises an alkylene moiety, wherein the alkylene moiety is optionally substituted with one or more moieties provided herein.

Triazole Linkage

In one embodiment of the capture agent, the anchor ligand and secondary ligand are linked together via a 1,4-substituted-1,2,3-triazole residue (Tz4). In another embodiment, the secondary ligand and the tertiary ligand are linked together via a 1,4-substituted-1,2,3-triazole residue (Tz4). In yet another embodiment, the tertiary ligand and the quaternary ligand are linked together via a 1,4-substituted-1,2,3-triazole residue (Tz4). In yet another embodiment, the anchor ligand and secondary ligand are linked together via a 1,4-substituted-1,2,3-triazole residue, and the secondary ligand and the tertiary ligand are linked together via a 1,4-substituted-1,2,3-triazole residue. In yet another embodiment, the anchor ligand and secondary ligand are linked together via a 1,4-substituted-1,2,3-triazole residue, the secondary ligand and the tertiary ligand are linked together via a 1,4-substituted-1,2,3-triazole residue and the tertiary ligand and the quaternary ligand are linked together via a 1,4-substituted-1,2,3-triazole residue.

Capture Agents

According to certain embodiments, the capture agent has a structure selected from the following:

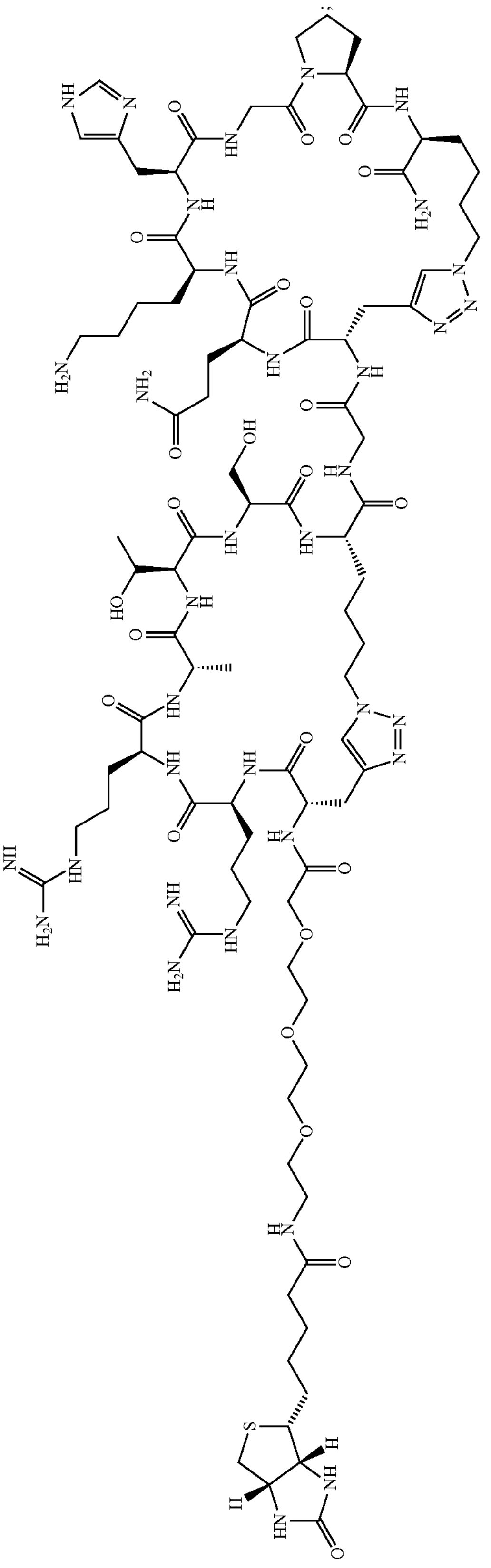
Chemical Formula: $C_{88}H_{143}N_{35}O_{24}S$
Exact Mass: 2106.08
Molecular Weight: 2107.36

-continued
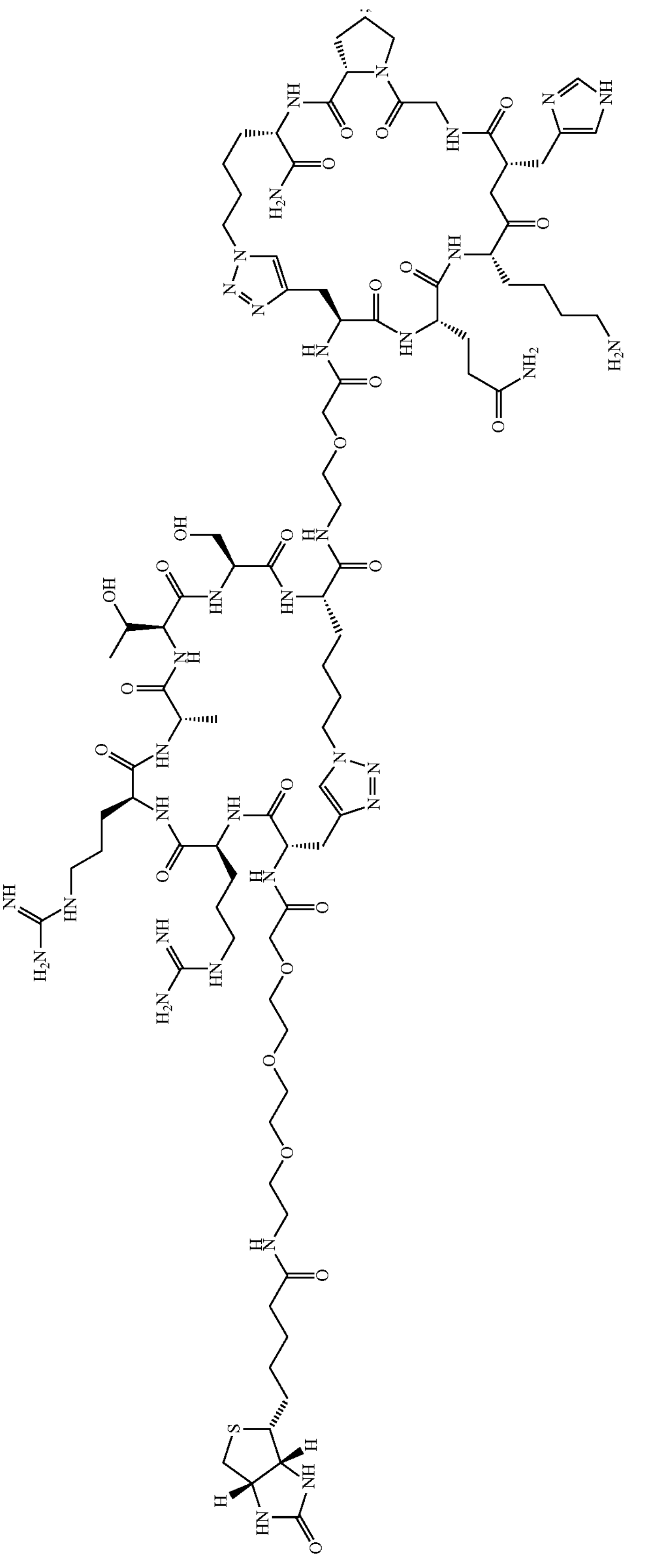
Chemical Formula: $C_{90}H_{147}N_{35}O_{25}S$
Exact Mass: 2150.10
Molecular Weight: 2151.41

-continued
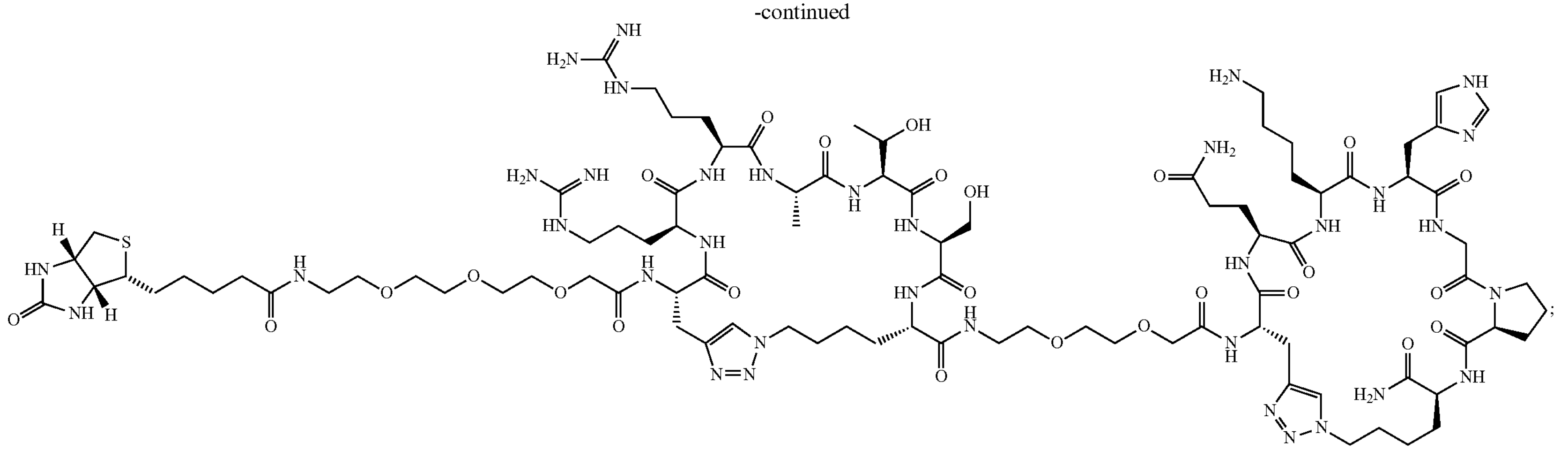
Chemical Formula: $C_{92}H_{151}N_{35}O_{26}S$
Exact Mass: 2194.13
Molecular Weight: 2195.47

-continued
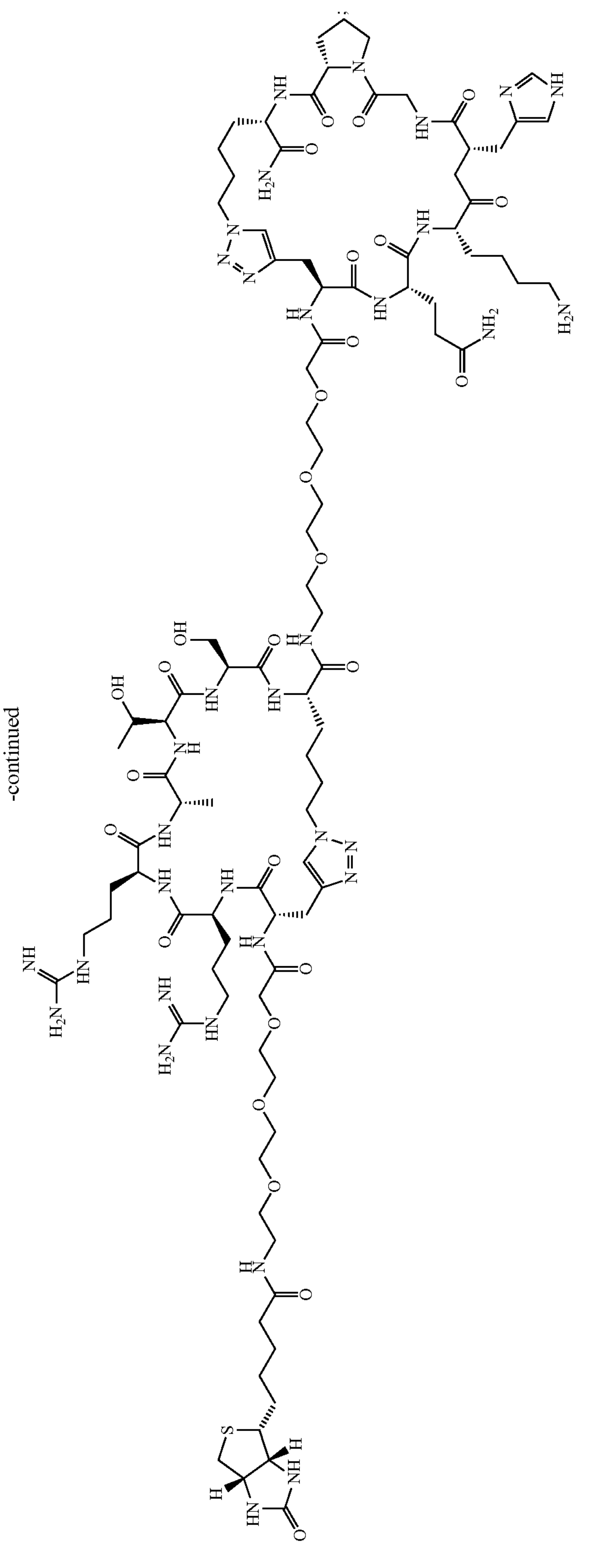
Chemical Formula: $C_{94}H_{155}N_{35}O_{27}S$
Exact Mass: 2238.16
Molecular Weight: 2239.52

-continued
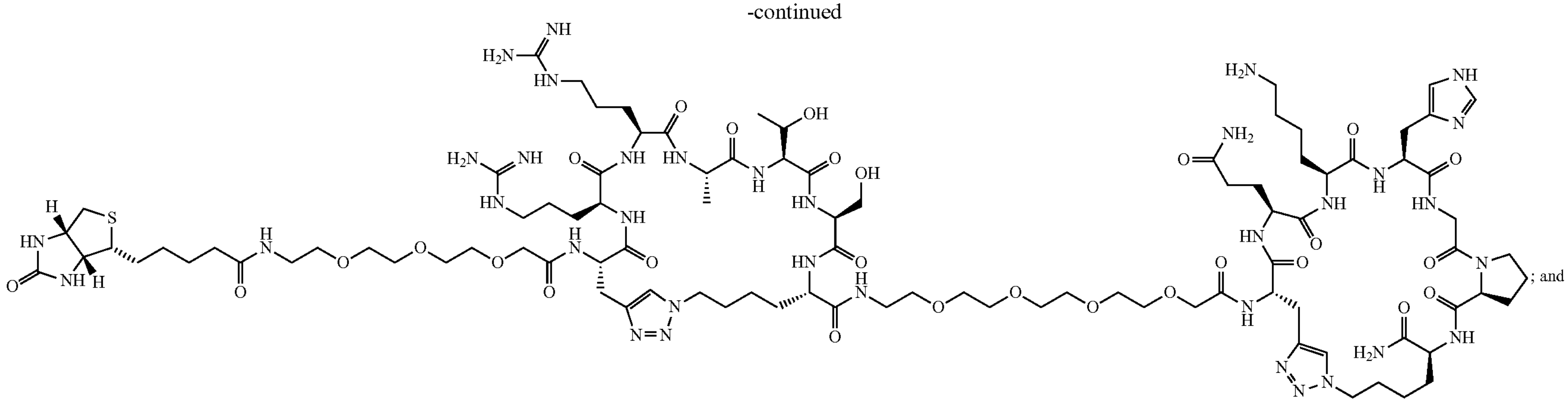
; and
Chemical Formula: $C_{96}H_{159}N_{35}O_{28}S$
Exact Mass: 2282.18
Molecular Weight: 2283.57

-continued
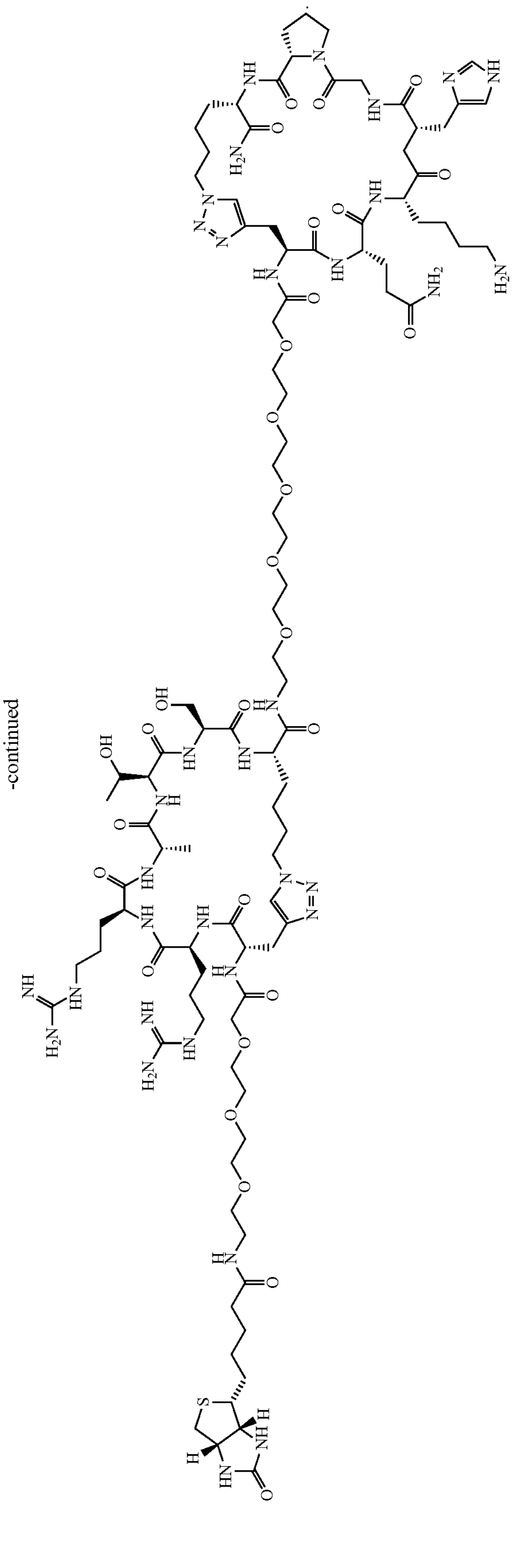
Chemical Formula: $C_{98}H_{163}N_{35}O_{29}S$
Exact Mass: 2326.21
Molecular Weight: 2327.62

According to other embodiments, the capture agent has a structure selected from the following:

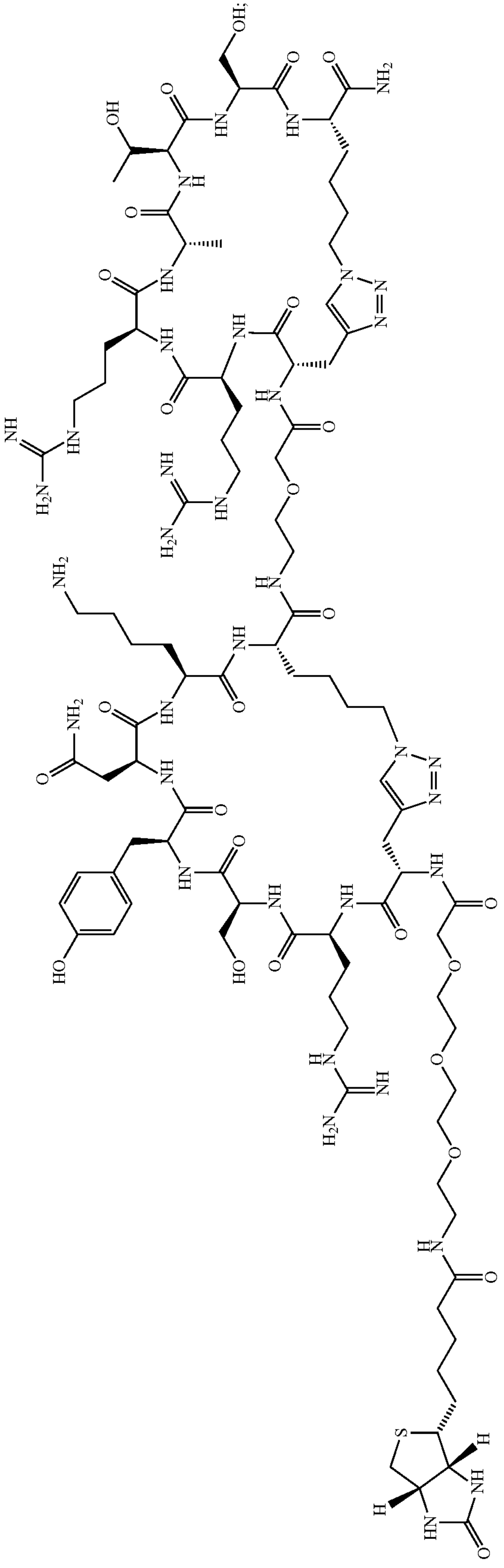
Chemical Formula: $C_{94}H_{154}N_{36}O_{27}S$
Exact Mass: 2251.15
Molecular Weight: 2252.52

-continued
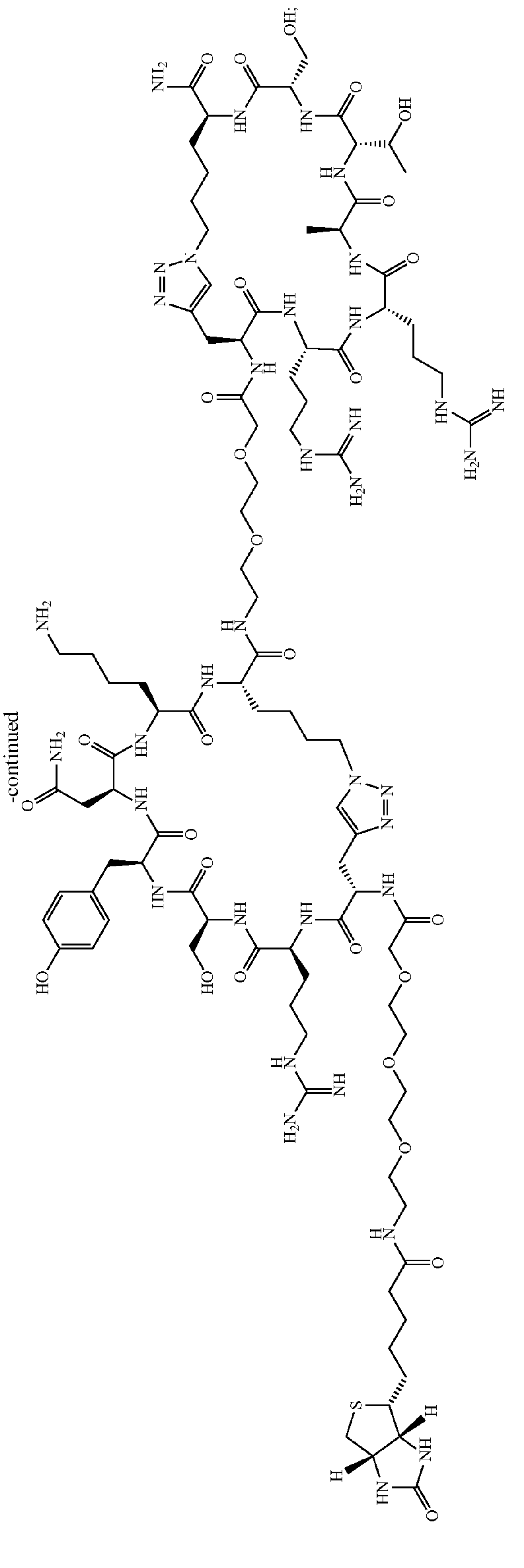
Chemical Formula: $C_{96}H_{158}N_{36}O_{28}S$
Exact Mass: 2295.18
Molecular Weight: 2296.57

-continued
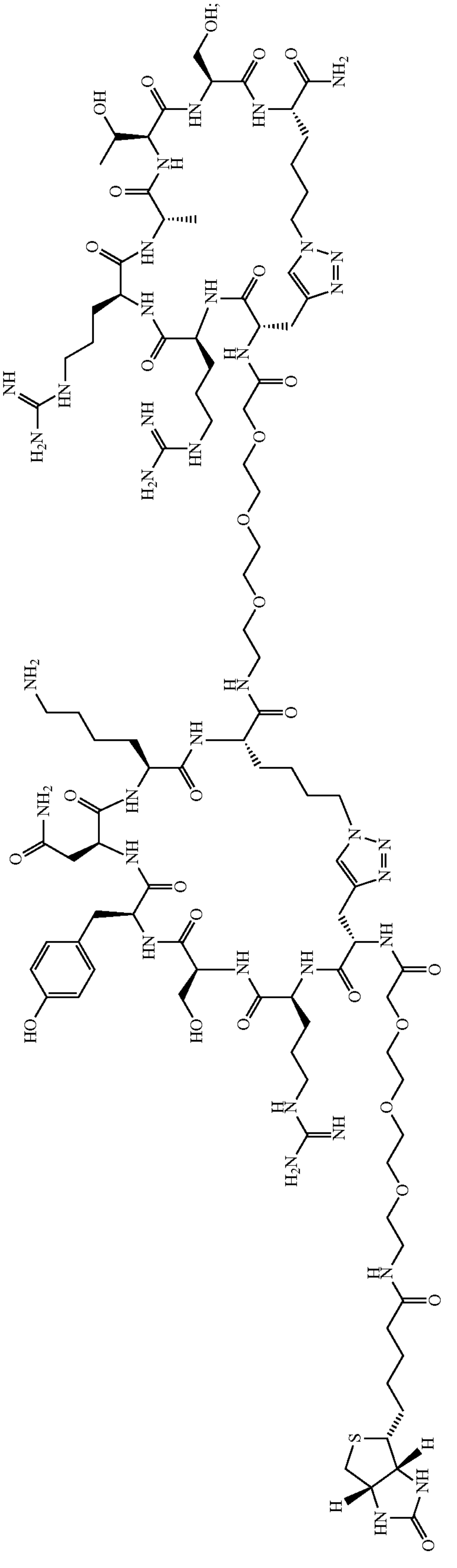
Chemical Formula: $C_{98}H_{162}N_{36}O_{29}S$
Exact Mass: 2339.20
Molecular Weight: 2340.62

-continued
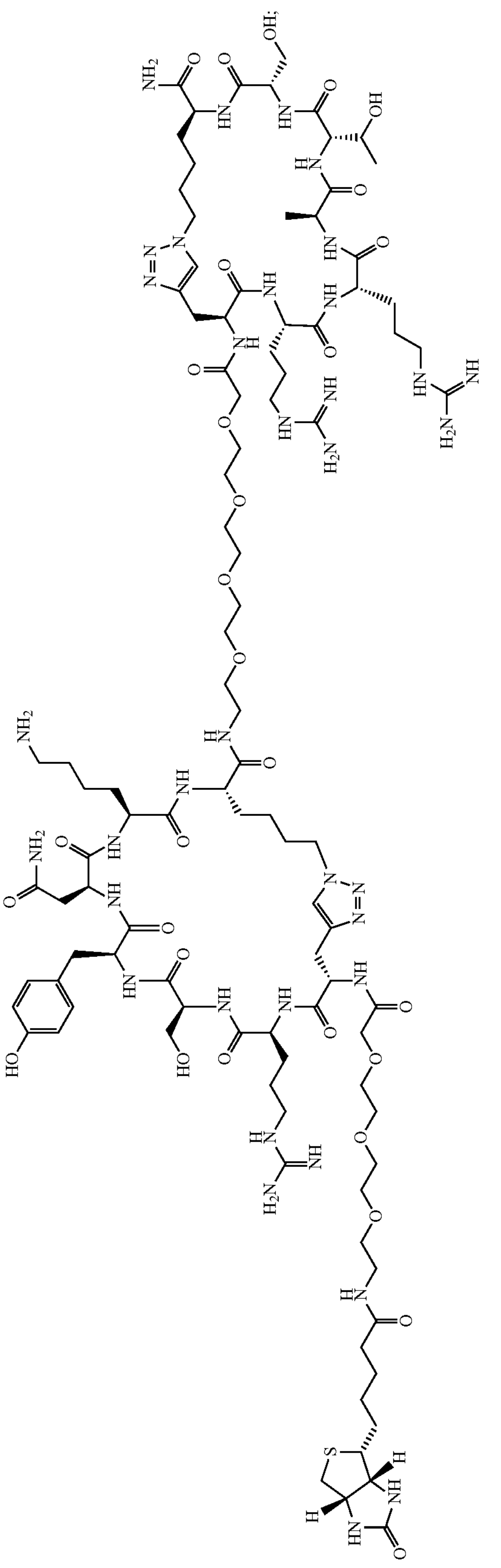
and
Chemical Formula: $C_{100}H_{166}N_{36}O_{30}S$
Exact Mass: 2383.23
Molecular Weight: 2384.68

-continued
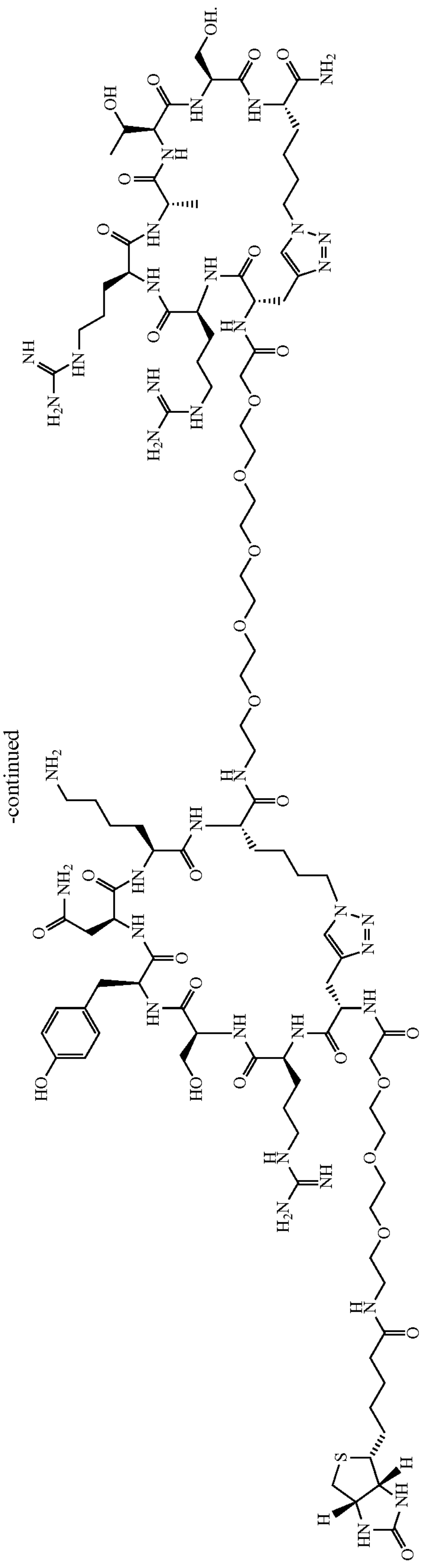
Chemical Formula: $C_{102}H_{170}N_{36}O_{31}S$
Exact Mass: 2427.26
Molecular Weight: 2428.73

Properties

In certain embodiments, the IL-17F capture agents provided herein are stable across a wide range of temperatures, pH values, storage times, storage conditions, and reaction conditions, and in certain embodiments the capture agents are more stable than a comparable antibody or biologic. In certain embodiments, the capture agents are stable in storage as a lyophilized powder. In certain embodiment, the capture agents are stable in storage at a temperature of about −80° C. to about 60° C. In certain embodiments, the capture agents are stable at room temperature. In certain embodiments, the capture agents are stable in human serum for at least 24 hours. In certain embodiments, the capture agents are stable at a pH in the range of about 3 to about 12. In certain embodiments, the capture agents are stable as a powder for two months at a temperature of about 60° C.

Detectable Labels

In some embodiments, the capture agent is labeled with a label selected from the group consisting of biotin, copper-DOTA, biotin-PEG3, aminooxyacetate, $^{19}$FB, $^{18}$FB and FITC-PEG3. In other embodiments, the capture agent is labeled with the detectable moiety consisting of $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, $^{11}$C and $^{76}$Br. In other embodiments, the label is a fluorescent label. In a particular embodiment, the detectable label is 18F.

Methods and Uses

As used herein, the terms "capture agent of the invention", or "capture agents of the invention" refer to synthetic protein-catalyzed capture agents which bind IL-17F, as described herein.

Also provided is a method of detecting IL-17F in a subject, comprising the step of contacting a biological sample from the subject with one or more capture agents of the invention. Also provided is the use of one or more capture agents of the invention for the detection of IL-17F in a subject.

Also provided is a method of detecting IL-17F in a biological sample using an immunoassay, wherein the immunoassay utilizes a capture agent as described herein, and wherein said capture agent replaces an antibody or its equivalent in the immunoassay. In certain embodiments, methods are provided for identifying, detecting, quantifying, or separating IL-17F in a biological sample using the capture agents as described herein. In one embodiment of the method, the immunoassay is selected from the group of Western blot, pull-down assay, dot blot, and ELISA.

Also provided is a method of detecting the presence of IL-17F in a human or mammalian subject, the method comprising the steps of:

a) administering to a biological sample from the subject one or more capture agents of the invention, wherein each capture agent is linked to a detectable moiety; and
b) detecting the moiety linked to each capture agent in the subject; wherein detection of the moiety indicates the presence of IL-17F in the subject.

Also provided herein is a method of detecting IL-17F in a sample comprising:

a) exposing the sample to one or more capture agents of the invention, wherein each capture agent is linked to a detectable moiety;
b) binding IL-17F in the biological sample to a capture agent; and
c) detecting the moiety linked to each capture agent on the substrate; wherein detection of the moiety on the substrate detects IL-17F in the sample.

Kits

Provided herein in certain embodiments are kits comprising one or more capture agents of the invention. In certain embodiments, these kits may be used for identifying, detecting, quantifying, and/or separating IL-17F, and in certain embodiments the kits may be used in the diagnosis and/or staging of a condition associated with the presence of IL-17F. In certain embodiments, a kit as provided herein comprises: (a) a substrate comprising an adsorbent thereon, wherein the adsorbent is suitable for binding IL-17F, and (b) a washing solution or instructions for making a washing solution, wherein the combination of the adsorbent and the washing solution allows detection of IL-17F. In other embodiments, the kits provided herein may be used in the treatment of a condition associated with the presence of IL-17F.

In certain embodiments, a kit may further comprise instructions for suitable operational parameters in the form of a label or a separate insert. For example, the kit may have standard instructions informing a consumer/kit user how to wash the probe after a sample of plasma or other tissue sample is contacted on the probe.

In certain embodiments, a kit comprises (a) one or more capture agents that specifically bind IL-17F; and (b) a detection reagent. Such kits can be prepared from the materials described herein.

The kits provided herein may optionally comprise a standard or control information, and/or a control amount of material, so that the test sample can be compared with the control information standard and/or control amount to determine if the test amount of IL-17F detected in a sample is an amount consistent with a diagnosis of a particular condition.

Synthesis of Capture Agents

Provided herein are methods for making (i.e., synthesizing) IL-17F-specific capture agents of the invention. In one embodiment, the method comprises the steps of:

a. selecting a first ligand that binds to a first epitope on the target protein,
b. selecting a second ligand that binds to a second epitope on the target protein,
c. selecting a linker that has a length that allows the linker to bind both the first ligand and the second ligand when both the first and the second ligands are specifically binding the first and second epitopes, respectively, and
d. binding the linker to the first and second ligands, thereby producing the synthetic capture agent that specifically binds to the target protein.

In certain embodiments the ligands are identified using the following steps:

1) a pre-clear to eliminate non-specific binders,
2) a product screen to identify hits resulting from epitope-templated in situ click chemistry,
3) a target screen against His-tagged IL-17F protein, and
4) another target screen against His-tagged IL-17F protein in 2% (v/v) human serum to identify peptides whose binding to IL-17F is unperturbed by serum proteins.

In certain embodiments, the first epitope and the second epitope are ~4.4 Å to ~26.4 Å, ~8.8 Å to ~26.4 Å or ~7 Å to ~15 Å or ~15 Å distant from each other. In some embodiments, the linker is longer than the distance between the first and second epitope. Optionally, the linker is 10-50%, 5-25% or 1-10% longer than the distance between the first and second epitope.

In certain embodiments, the capture agent has a binding affinity for the target protein greater than either of the ligands. In some embodiments, the capture agent has a binding affinity that is at least 50, 75 or 90% of the binding affinity of a full cooperative binder. In other embodiments, the capture agent has a binding affinity that is at least 1, 2, 3, 4, 5, 6, 7, 8, 9, 10, 20, 30, 40, 50, 60, 70, 80, 90 or 100% of the binding affinity of a full cooperative binder.

In certain embodiments, the target protein is a synthetic epitope, wherein the synthetic epitope comprises at least a 20 amino acid sequence of a full length protein, wherein at least one amino acid of the synthetic epitope comprises an azide or an acetylene group. In some embodiments, the synthetic epitope is at least 10, 20, 30, 40, 50, 60, 70, 80, 90, 100, 110, 120, 150, 200, 250 or 300 amino acid sequence of a full length protein. In some embodiments, at least two amino acids of the synthetic epitope comprise an azide or an acetylene group. In other embodiments, at least 3, 4, 5, 6, 7, 8, 9 or 10 amino acids of the synthetic epitope comprise an azide or an acetylene group.

According to certain embodiments, the full length protein is a naturally occurring protein. According to other embodiments, the naturally occurring protein is IL-17.

According to certain embodiments, the capture agent binds the synthetic epitope and the full length protein with a binding affinity that is at least 50% of the binding affinity of a full cooperative binder. According to certain embodiments, the capture agent binds the synthetic epitope and the full length protein with a binding affinity that is at least 1, 2, 3, 4, 5, 6, 7, 8, 9, 10, 20, 30, 40, 50, 60, 70, 80, 90 or 100% of the binding affinity of a full cooperative binder.

BRIEF DESCRIPTION OF THE DRAWINGS

FIG. 1A. N-terminal sequence differences occur in the mature proteins that discriminate IL-17F (SEQ ID NO:38) from IL-17A (SEQ ID NO:37). This region of uniqueness corresponds to Arg-31 to Thr-79 in IL-17F. FIG. 1B. Sequence of the designed Epitope1 fragment containing a biotin-$PEG_3$ assay handle and a strategically substituted azide click handle (C48Az4; Az4=L-azidolysine), (Biotin-$PEG_3$-FFQKPES (SEQ ID NO:1) [Az4]PPVPGGS) (SEQ ID NO:32). FIG. 1C. Sequence of the designed Epitope2 fragment containing a biotin-$PEG_3$ assay handle and a strategically substituted azide click handle (I62Az4), (Biotin-$PEG_3$-GI[Az4]NENQRVS) (SEQ ID NO:33).

FIG. 2A. Sandwich ELISAs for human IL-17F protein against $PEG_3$-biotin-modified Cy(RRATS) (SEQ ID NO:9) and Cy(RRAQS) (SEQ ID NO:10) yield EC50 values of 66 to 52 nM. A similarly assayed biotinylated monoclonal antibody (TA319597, Origene) shows similar binding affinity. FIG. 2B. Point ELISAs for human IL-17F and IL-17A proteins against the two macrocyclic peptide ligands, $PEG_3$-biotin-modified Cy(RRATS) (SEQ ID NO:9) and Cy(RRAQS) (SEQ ID NO:10), demonstrate preferential binding to IL-17F. FIG. 2C. Mass spectrum of Cy(RRATS) (SEQ ID NO:9)-$PEG_3$-biotin. FIG. 2D. Mass spectrum of Cy(RRAQS) (SEQ ID NO:10)-$PEG_3$-biotin.

FIG. 3A. His-tagged IL-17F epitopes were synthesized to contain strategic scrambling of the sequences either N-terminal or C-terminal to the location of the click handle (C48S). 1) SEQ ID NO:39, 2) SEQ ID NO:40, 3) SEQ ID NO:41. Scrambled residues are shown in italics. FIG. 3B. Point ELISAs for the His-tagged IL-17F epitopes against the two macrocyclic peptide ligands, $PEG_3$-biotin-modified Cy(RRATS) (SEQ ID NO:9) and Cy(RRAQS) (SEQ ID NO:10), demonstrate preferential binding to the sequence FFQKPES (SEQ ID NO:1).

FIG. 4A. Sandwich ELISAs for human IL-17F protein against $PEG_3$-biotin-modified Cy(QKHGP) (SEQ ID NO:15), Cy(TKHGP) (SEQ ID NO:16), Cy(KKGWP) (SEQ ID NO:23), and Cy(RSYNK) (SEQ ID NO:28) yield EC50 values of 72 to 15 nM. FIG. 4B. Point ELISAs for human IL-17F and IL-17A proteins against the four macrocyclic peptide ligands, $PEG_3$-biotin-modified Cy(QKHGP) (SEQ ID NO:15), Cy(TKHGP) (SEQ ID NO:16), Cy(KKGWP) (SEQ ID NO:23), and Cy(RSYNK) (SEQ ID NO:28), demonstrate preferential binding to IL-17F. FIG. 4C. Point ELISAs for human IL-17F and IL-17A proteins against macrocyclic peptide ligands, RRATS (SEQ ID NO:9), RSYNK (SEQ ID NO:28), (QKHGP) (SEQ ID NO:15), demonstrate preferential binding to IL-17F or IL-17A.

FIG. 5A. In the monomeric IL-17F protein, the distance between the sequence FFQKPES (SEQ ID NO:1) (in IL-17F Epitope1) and IL-17F Epitope2, NENQRVS (SEQ ID NO:3) is ~15 Å. Using a linker whose length is similar to the distance between the two binding sites on the protein, a biligand can be synthesized containing macrocycles targeted to each of the two IL-17F epitopes. FIG. 5B. In the homodimeric IL-17F protein, the distance between the sequence FFQKPES (SEQ ID NO:1) (in IL-17F Epitope1) from one monomer and IL-17F Epitope2, NENQRVS (SEQ ID NO:3) from the other monomer is ~7 Å. Using a linker whose length is similar to the distance between the two binding sites bridging the protein dimer, another biligand can be synthesized containing macrocycles targeted to each of the two IL-17F epitopes. PDB ID: 1JPY.

FIG. 6A. Biotin-$PEG_3$-Cy(RRATS) (SEQ ID NO:9)-Gly-Cy(QKHGP) (SEQ ID NO:15) (Gly=4.4 Å). FIG. 6B. Biotin-$PEG_3$-Cy(RRATS) (SEQ ID NO:9)-$PEG_1$-Cy(QKHGP) (SEQ ID NO:15) ($PEG_1$=8.8 Å). FIG. 6C. Biotin-$PEG_3$-Cy(RRATS) (SEQ ID NO:9)-$PEG_2$-Cy(QKHGP) (SEQ ID NO:15) ($PEG_2$=13.2 Å). FIG. 6D. Biotin-$PEG_3$-Cy(RRATS) (SEQ ID NO:9)-$PEG_3$-Cy(QKHGP) (SEQ ID NO:15) ($PEG_3$=17.6 Å). FIG. 6E. Biotin-$PEG_3$-Cy(RRATS) (SEQ ID NO:9)-$PEG_4$-Cy(QKHGP) (SEQ ID NO:15) ($PEG_4$=22 Å). FIG. 6F. Biotin-$PEG_3$-Cy(RRATS) (SEQ ID NO:9)-$PEG_5$-Cy(QKHGP) (SEQ ID NO:15) ($PEG_5$=26.4 Å).

Chem. Int. Ed. Engl. 2015, incorporated herein by reference in its entirety). Using that procedure, one identifies at least one unique peptide binder to each of at least two epitopes on the target. Those peptide binders are validated via carrying out binding assays against the full protein target (11) as well as against the SynEps. For those binding assays, the SynEps are prepared with the naturally occurring residue in place of the click handle (16). Ideally, the different regions of the target protein to which the different ligands bind will be relatively close together (a few nanometers or less) in the tertiary protein structure. For even a single SynEp, a screen can produce PCCs that bind to two different sites.

Figure 8:
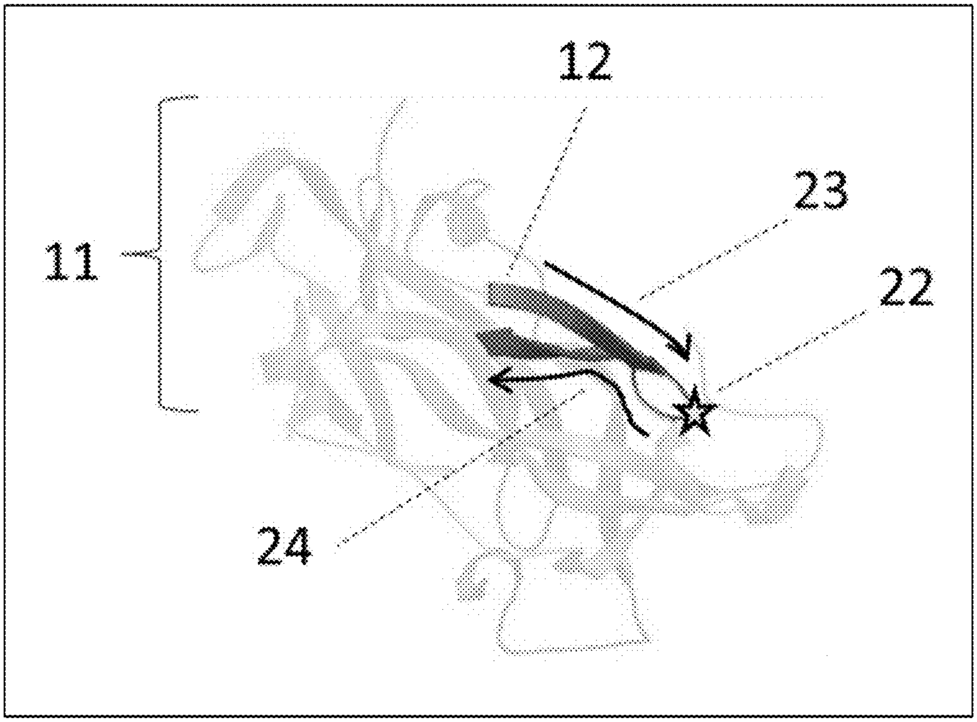

FIG. 8: PCC that binds to two different sites. The region representing the epitope of interest (12) is highlighted against a dimmer background of the full protein (11). The amino acid residue that was substituted for a click handle in the SynEp structure is indicated by a star (22). During the SynEp screening steps, PCCs that bind to the N-terminal side of the epitope (23) or the C-terminal side (24) may both be identified.

Figure 9:
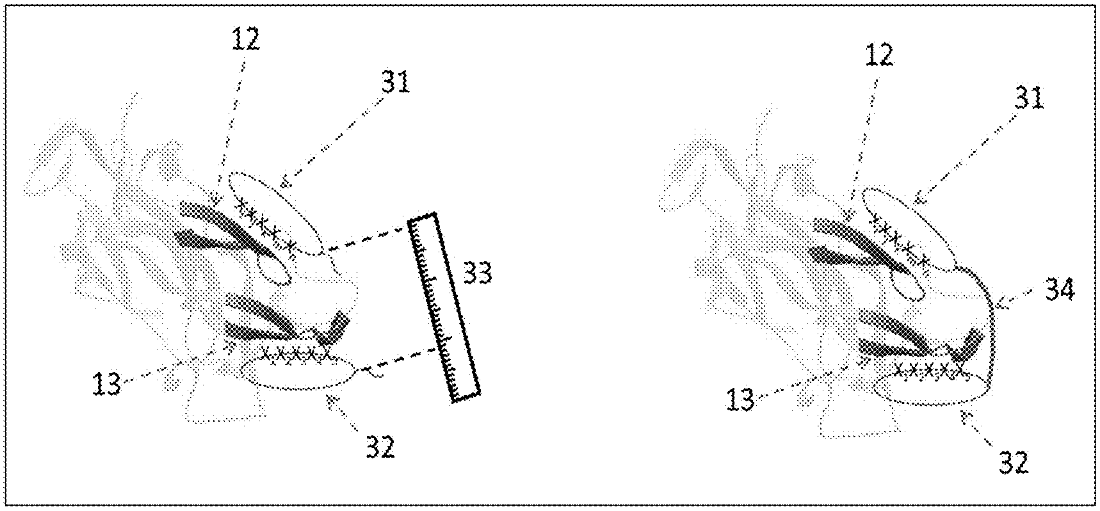

FIG. 9: Estimation of optimal linker length. A first PCC (31) that binds to the N-side of one epitope (12) and a second PCC (32) binding to the C-side of a second epitope (13) are shown. Analysis of this binding arrangement, together with the structure of the protein from, for example, the Protein Database, permits an estimate of the length of an optimized linker (33). Such an estimate can narrow down the choice of candidate linkers to a very small number. One example might be to use such a length estimate to select one or two length-marched polyethylene glycol oligomers for testing. The best linker (34) is the one that brings the biligand affinity closest to that of a fully cooperative binder.

Figure 10:
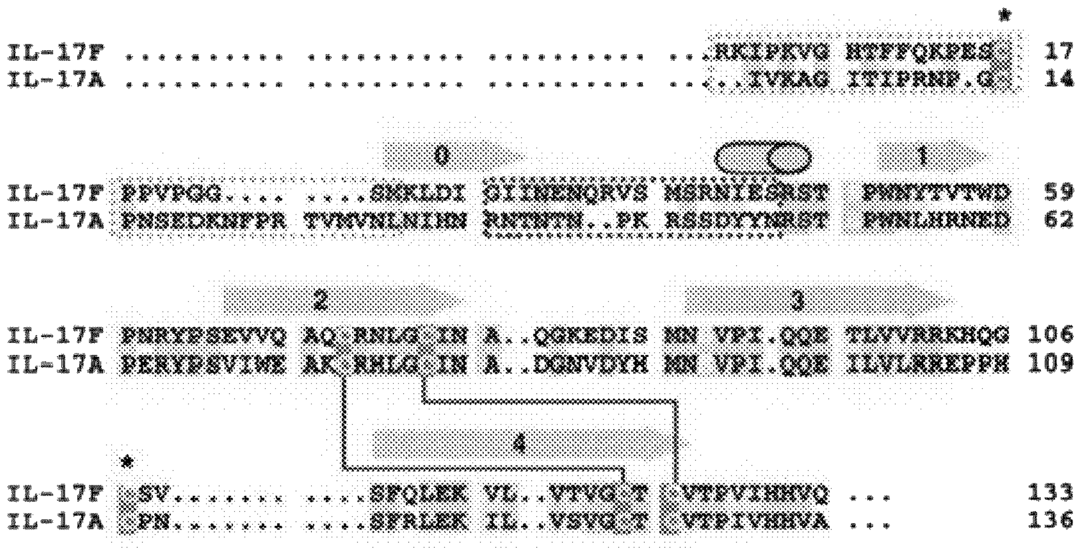

FIG. 10: IL-17F and IL-17A are close homologs. Alignment of IL-17F (SEQ ID NO:38) and IL-17A (SEQ ID NO:37). Residues shaded green are identical, yellow are homologous and no highlight are unique.

Figure 11:
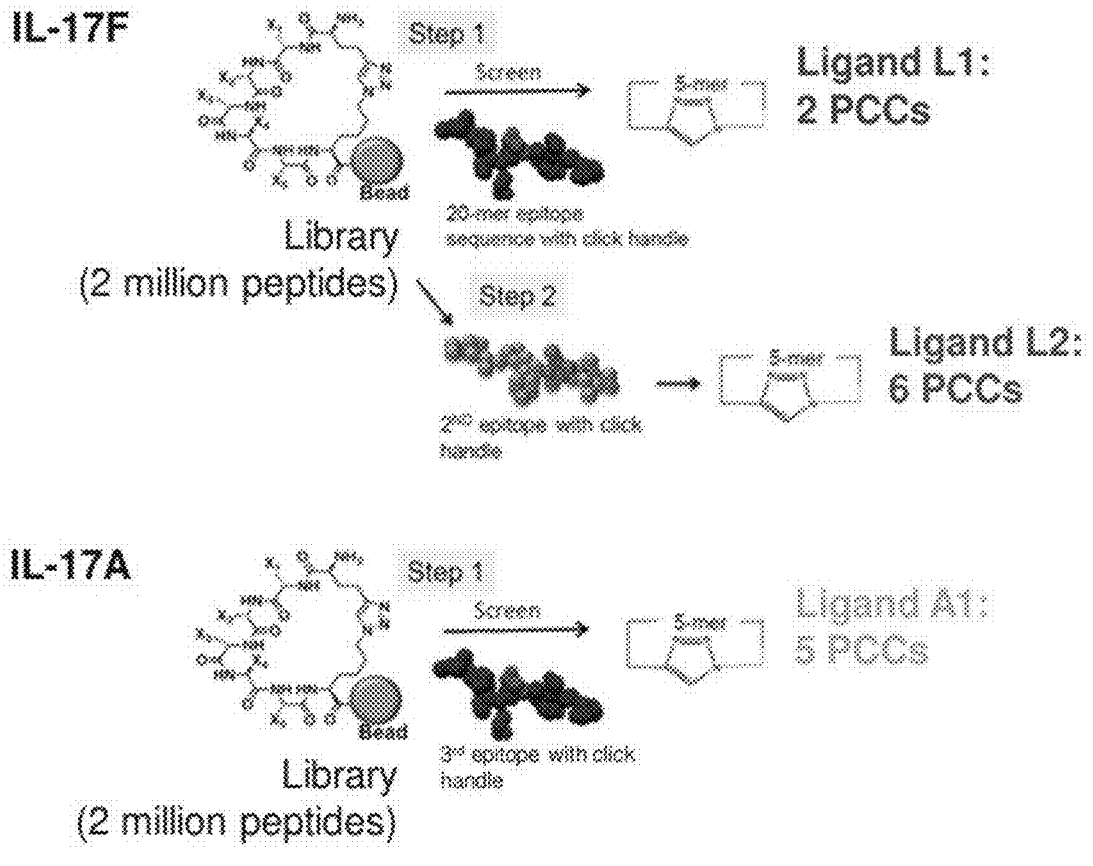

FIG. 11: Generation of ligands for IL-17F and IL-17A. Anchor ligands were generated against IL-17F using two epitopes and against IL-17A using one epitope.

Figure 12A:
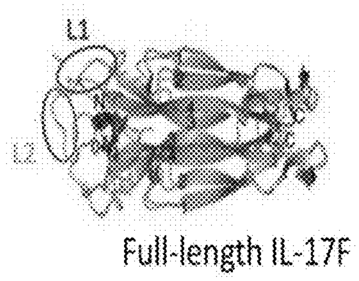
Figure 12C:
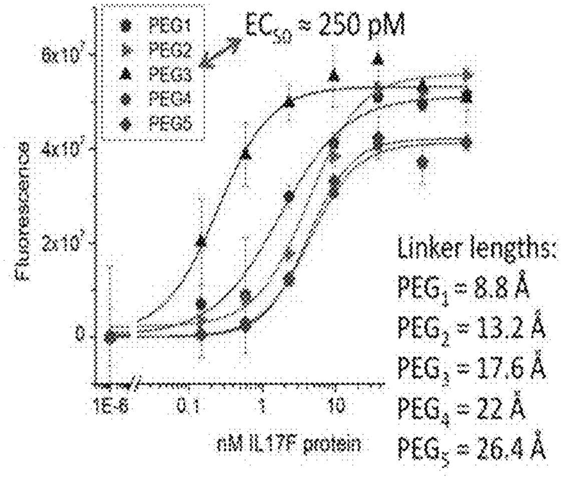
Figure 12B:
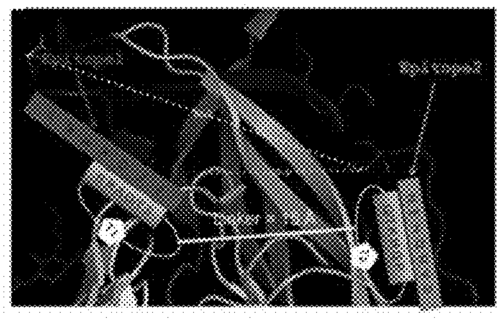
Figure 12D:
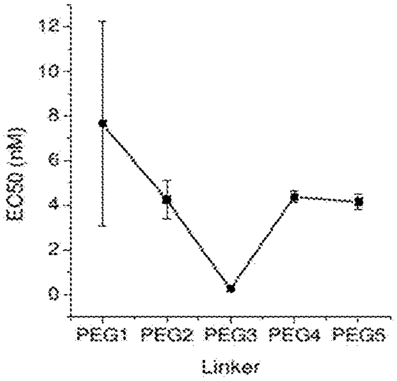

FIGS. 12A-12D: Designing an optimized PCC biligand against IL-17F by exploiting cooperativity. FIG. 12A. Drawing of full-length IL-17F. PCCs were developed against the epitopes labeled L1 and L2. FIG. 12B. Expanded view of IL-17F showing the targeted region. The distance between the chemically accessible spots on the PCCs is estimated to be 15 Å. FIG. 12C. Demonstration that a linker of length closest to 15 Å ($PEG_3$) yields the best binder (by ~10-fold). Biligands are of the form Biotin-$PEG_3$-Cy(RSYNK) (SEQ ID NO:28)-$PEG_x$-Cy(RRATS) (SEQ ID NO:9) (x=1 to 5). FIG. 12D. Graph showing that that a linker of length closest to 15 Å ($PEG_3$) yields the best binder (by ~10-fold).

Figure 13A:
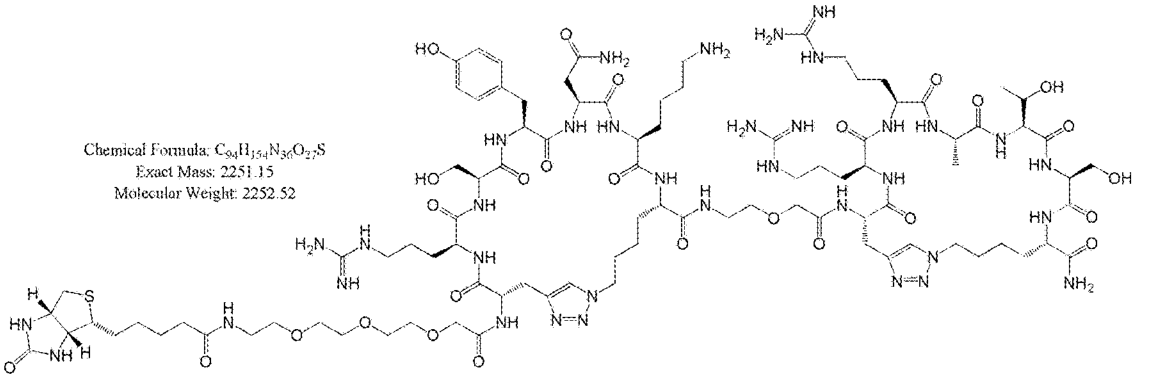
Figure 13B:
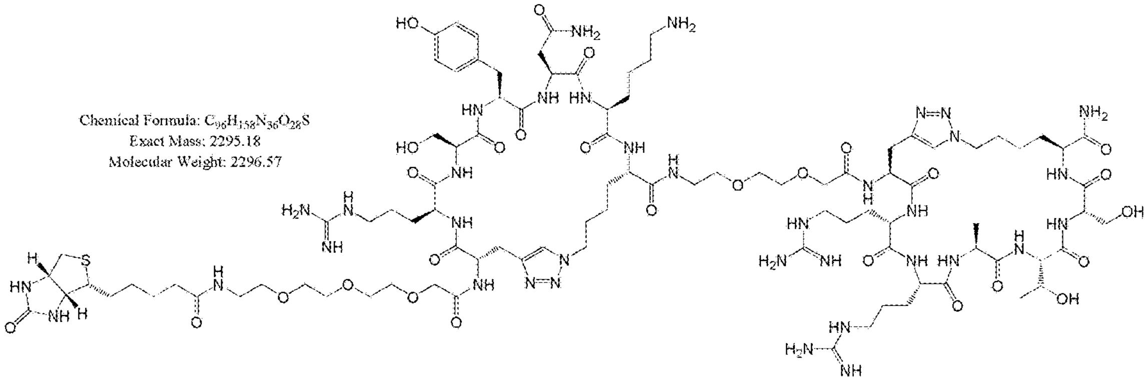
Figure 13C:
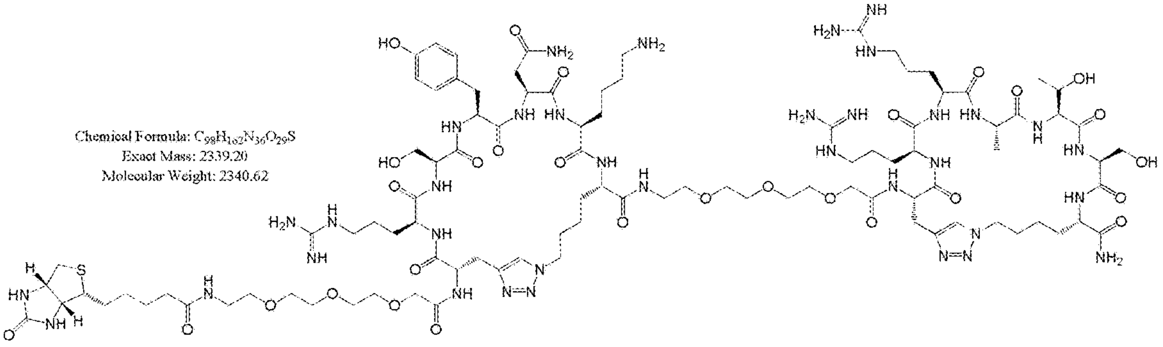
Figure 13D:
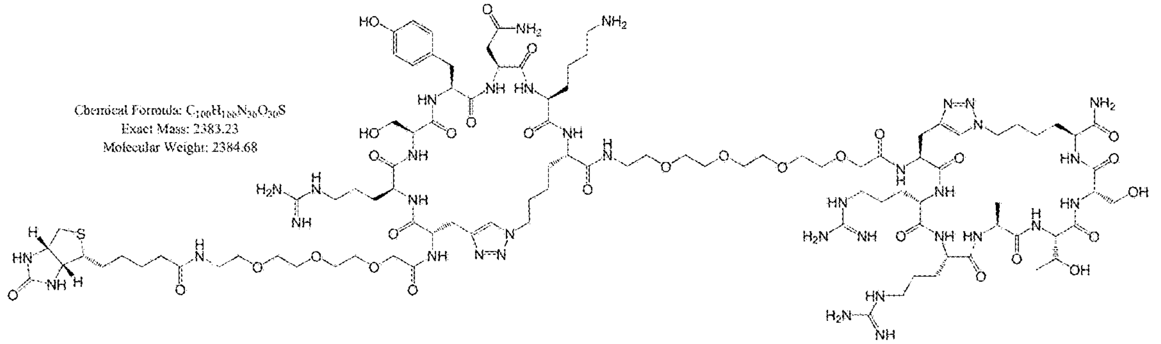
Figure 13E:
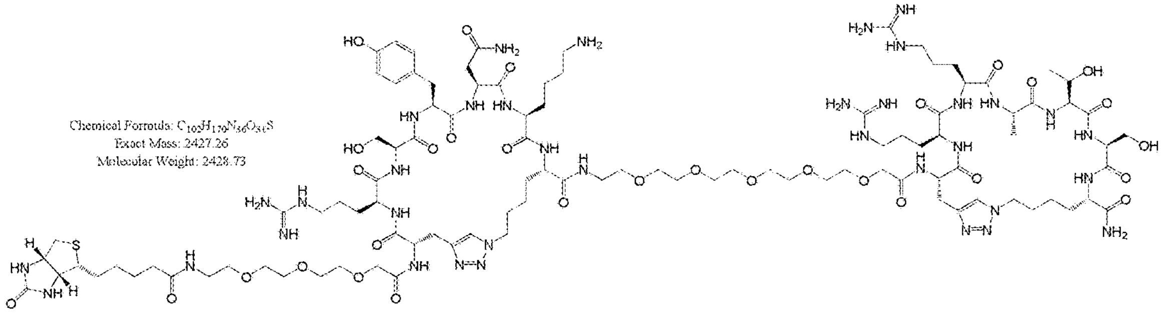

FIGS. 13A-13E: Structures of biligands with PEG linkers ranging from 8.8 to 26.4 Å to join the two macrocycles. FIG. 13A. Biotin-$PEG_3$-Cy(RSYNK) (SEQ ID NO:28)-$PEG_1$-Cy (RRATS) (SEQ ID NO:9) ($PEG_1$=8.8 Å). FIG. 13B. Biotin-$PEG_3$-Cy(RSYNK) (SEQ ID NO:28)-$PEG_2$-Cy(RRATS) (SEQ ID NO:9) ($PEG_2$=13.2 Å). FIG. 13C. Biotin-$PEG_3$-Cy(RSYNK) (SEQ ID NO:28)-$PEG_3$-Cy(RRATS) (SEQ ID NO:9) ($PEG_3$=17.6 Å). FIG. 13D. Biotin-$PEG_3$-Cy (RSYNK) (SEQ ID NO:28)-$PEG_4$-Cy(RRATS) (SEQ ID NO:9) ($PEG_4$=22 Å). FIG. 13E. Biotin-$PEG_3$-Cy(RSYNK) (SEQ ID NO:28)-$PEG_5$-Cy(RRATS) (SEQ ID NO:9) ($PEG_5$=26.4 Å).

FIG. 14: *Plasmodium falciparum* Histidine Rich Protein-2 (Pf.HRP-2). The sequence map of Pf.HRP-2 is shown (SEQ ID NO:42).

Figure 15:
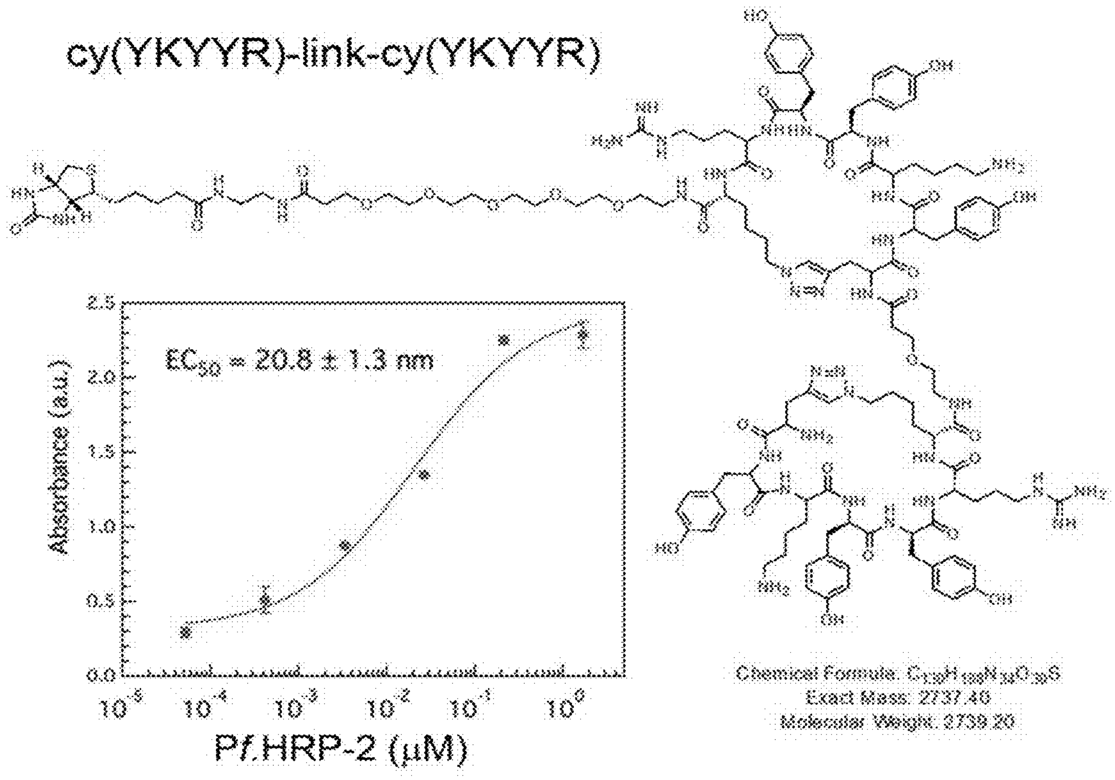

FIG. 15: Structure and EC50 data on YKYYR (SEQ ID NO:29) dimer.

Figure 16:
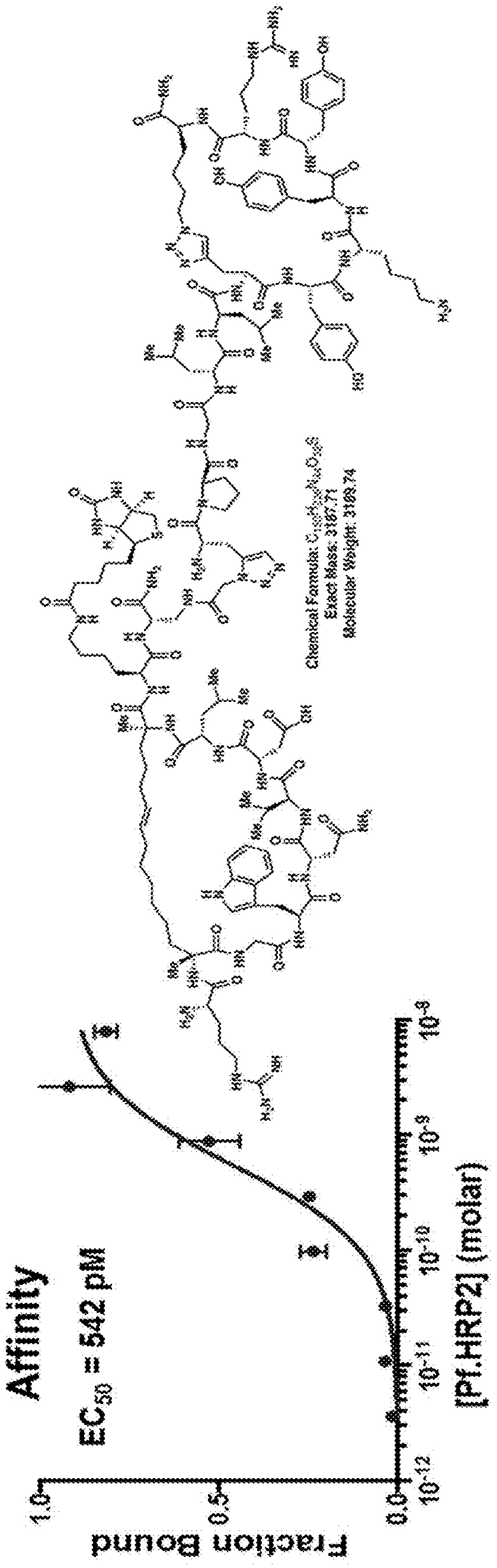

FIG. 16: cy(YKYYR) (SEQ ID NO:29)-linker-cy(GWNVDL) (SEQ ID NO:30) biligand with linker developed through library screening.

DETAILED DESCRIPTION

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Unless the context requires otherwise, throughout the present specification and claims, the word “comprise” and variations thereof, such as, “comprises” and “comprising” are to be construed in an open, inclusive sense, that is as “including, but not limited to”.

Reference throughout this specification to “one embodiment” or “an embodiment” means that a particular feature, structure or characteristic described in connection with the embodiment is included in at least one embodiment of the present invention. Thus, the appearances of the phrases “in one embodiment” or “in an embodiment” in various places throughout this specification are not necessarily all referring to the same embodiment. Furthermore, the particular features, structures, or characteristics may be combined in any suitable manner in one or more embodiments.

Definitions

“Amino” refers to the —$NH_2$ radical.

“Cyano” refers to the —CN radical.

“Hydroxy” or “hydroxyl” refers to the —OH radical.

“Imino” refers to the =NH substituent.

“Nitro” refers to the —$NO_2$ radical.

“Oxo” refers to the =O substituent.

“Thioxo” refers to the =S substituent.

“Alkyl” refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n propyl, 1 methylethyl (isopropyl), n-butyl, n-pentyl, 1,1 dimethylethyl (t-butyl), 3 methylhexyl, 2 methylhexyl, ethenyl, prop-1-enyl, but-1-enyl, pent-1-enyl, penta 1,4 dienyl, ethynyl, propynyl, butynyl, pentynyl, hexynyl, and the like. Unless stated otherwise specifically in the specification, an alkyl group may be optionally substituted.

“Alkylene” or “alkylene chain” refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group may be optionally substituted.

"Aminocarbonyl" refers to a radical of the formula —$C(=O)NR_aR_a$, where each $R_a$ is independently H, alkyl or a linker moiety.

"α-amino carbonyl" refers to a radical of the formula —$C(=O)CR_b(NR_aR_a)$, where each $R_a$ is independently H, alkyl or a linker moiety and $R_b$ is H or alkyl. In some embodiments, an alpha amino carbonyl is part of a cyclic moiety (e.g., peptide) where the carbonyl is within the ring and the amino ($NR_aR_a$) is exocyclic. For example, in certain embodiments an alpha aminocarbonyl is useful for Edman degradation of cyclic peptides.

α-amido carbonyl" refers to a radical of the formula —$C(=O)CR_b(N(C=O)R_aR_a)$, where each $R_a$ is independently H, alkyl or a linker moiety and $R_b$ is H or alkyl. In some embodiments, an alpha amido carbonyl is part of a cyclic moiety (e.g., peptide) where the carbonyl is within the ring and the amido ($N(C=O)R_aR_a$) is exocyclic.

"Alkylamino" refers to a radical of the formula —$NHR_a$ or —$NR_aR_a$ where each $R_a$ is, independently, an alkyl radical as defined above containing one to twelve carbon atoms. Unless stated otherwise specifically in the specification, an alkylamino group may be optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7 dimethyl bicyclo[2.2.1]heptanyl, and the like. Unless otherwise stated specifically in the specification, a cycloalkyl group may be optionally substituted.

"Cycloalkylalkyl" refers to a radical of the formula —$R_bR_d$ where $R_b$ is an alkylene chain as defined above and $R_d$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2 trifluoroethyl, 1,2 difluoroethyl, 3 bromo 2 fluoropropyl, 1,2 dibromoethyl, and the like. Unless stated otherwise specifically in the specification, a haloalkyl group may be optionally substituted.

"Heterocyclyl" or "heterocyclic ring" refers to a stable 3 to 18 membered non aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2 oxopiperazinyl, 2 oxopiperidinyl, 2 oxopyrrolidinyl, oxazolidinyl, piperidinyl, piperazinyl, 4 piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1 oxo thiomorpholinyl, and 1,1 dioxo thiomorpholinyl. Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —RbRe where Rb is an alkylene chain as defined above and Re is a heterocyclyl radical as defined above, and if the heterocyclyl is a nitrogen containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5 to 14 membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4 benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2 a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2 oxoazepinyl, oxazolyl, oxiranyl, 1-oxidopyridinyl, 1 oxidopyrimidinyl, 1-oxidopyrazinyl, 1-oxidopyridazinyl, 1 phenyl 1H pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula $—R_bR_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (e.g., alkyl, alkylene, alkoxy, alkylamino, aminocarbonyl, α-aminocarbonyl, α-amidocarbonyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $—NR_gR_h$, $—NR_gC(=O)R_h$, $—NR_gC(=O)NR_gR_h$, $—NR_gC(=O)OR_h$, $—NR_gSO2R_h$, $—OC(=O)NR_gR_h$, $—OR_g$, $—SR_g$, $—SOR_g$, $—SO_2R_g$, $—OSO_2R_g$, $—SO_2OR_g$, $=NSO_2R_g$, and $—SO_2NR_gR_h$. "Substituted" also means any of the above groups in which one or more hydrogen atoms are replaced with $—C(=O)R_g$, $—C(=O)OR_g$, $—C(=O)NR_gR_h$, $—CH_2SO_2R_g$, $—CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Prodrug" is meant to indicate a compound that may be converted under physiological conditions or by solvolysis to a biologically active compound of the invention (i.e., a disclosed capture agent). Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7 9, 21 24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable disclosed capture agents being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled disclosed capture agents, for example, those incorporating a radioactive isotope, are useful in drug and/or substrate tissue distribution studies. The radioactive isotopes tritium, i.e. $^3H$, and carbon- 14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled capture agents can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed capture agents. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2 dimethylaminoethanol, 2 diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

The compounds (capture agents) of the invention, or their pharmaceutically acceptable salts may contain one or more asymmetric centers and may thus give rise to enantiomers, diastereomers, and other stereoisomeric forms that may be defined, in terms of absolute stereochemistry, as (R) or (S) or, as (D) or (L) for amino acids. The present invention is meant to include all such possible isomers, as well as their racemic and optically pure forms. Optically active (+) and ( ), (R) and (S), or (D) and (L) isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. (D)-amino acids (also referred to as D-amino acids) are referred to herein in lower case letters (e.g. D-valine is referred to as "v"), while (L)-amino acids (also referred to herein as L-amino acids) are referred to in upper case letters (e.g. L-valine or valine is referred to as "V"). Glycine is non-chiral and is referred to as "G".

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present invention includes tautomers of any said compounds.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

The term "capture agent" as used herein refers to a composition that comprises two or more target-binding moieties and which specifically binds to a target protein via those target-binding moieties. Each target-binding moiety exhibits binding affinity for the target protein, either individually or in combination with other target-binding moieties. In certain embodiments, each target-binding moiety binds to the target protein via one or more non-covalent interactions, including for example hydrogen bonds, hydrophobic interactions, and van der Waals interactions. A capture agent may comprise one or more organic molecules, including for example polypeptides, peptides, polynucleotides, and other non-polymeric molecules. In some aspects a capture agent is a protein catalyzed capture agent (PCC).

The term "epitope" as used herein refers to a distinct molecular surface of a protein (e.g., IL-17F). Typically, the epitope is a polypeptide and it can act on its own as a finite sequence of 10-40 amino acids.

The terms "polypeptide," "peptide," and "protein" are used interchangeably herein to refer to an amino acid sequence comprising a polymer of amino acid residues. The terms apply to amino acid polymers in which one or more amino acid residues is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids, and isomers thereof. Naturally occurring amino acids are those encoded by the genetic code, as well as those amino acids that are later modified, e.g., hydroxyproline, carboxyglutamate, O-phosphoserine, and isomers thereof. The term "amino acid analogs" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

The term "non-natural amino acid" as used herein refers to an amino acid that is different from the twenty naturally occurring amino acids (alanine, arginine, glycine, asparagine, aspartic acid, cysteine, glutamine, glutamic acid, serine, threonine, histidine, lysine, methionine, proline, valine, isoleucine, leucine, tyrosine, tryptophan, phenylalanine) in its side chain functionality. The non-natural amino acid can be a close analog of one of the twenty natural amino acids, or it can introduce a completely new functionality and chemistry, as long as the hydrophobicity of the non-natural amino acid is either equivalent to or greater than that of the natural amino acid. The non-natural amino acid can either replace an existing amino acid in a protein (substitution), or be an addition to the wild type sequence (insertion). The incorporation of non-natural amino acids can be accomplished by known chemical methods including solid-phase peptide synthesis or native chemical ligation, or by biological methods.

The terms "specific binding," "selective binding," "selectively binds," or "specifically binds" as used herein refer to capture agent binding to an epitope on a predetermined antigen. Typically, the capture agent binds with an affinity ($K_D$) of approximately less than $10^{-7}$ M, such as approximately less than $10^{-8}$ M, $10^{-9}$ M or $10^{-10}$ M or even lower.

The term "$K_D$" as used herein refers to the dissociation equilibrium constant of a particular capture agent-antigen interaction. Typically, the capture agents of the invention bind to IL-17 with a dissociation equilibrium constant (Ks) of less than approximately $10^{-6}$ M, $10^{-7}$ M, such as less than approximately $10^{-8}$ M, $10^{-9}$ M or $10^{-10}$ M or even lower, for example, as determined using surface plasmon resonance (SPR) technology in a Biacore instrument using the antigen as the ligand and the capture agent as the analyte, and binds to the predetermined antigen with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the capture agent, so that when the $K_D$ of the capture agent is very low (that is, the capture agent is highly specific), then the amount with which the affinity for the antigen is lower than the affinity for a non-specific antigen may be at least 10,000 fold.

The term "$k_d$" ($sec^{-1}$) as used herein refers to the dissociation rate constant of a particular capture agent-antigen interaction. Said value is also referred to as the $k_{off}$ value.

The term "$k_a$" ($M^{-1} \times sec^{-1}$) as used herein refers to the association rate constant of a particular capture agent-antigen interaction.

The term "$K_D$" (M) as used herein refers to the dissociation equilibrium constant of a particular capture agent-antigen interaction.

The term "$K_A$" ($M^{-1}$) as used herein refers to the association equilibrium constant of a particular capture agent-antigen interaction and is obtained by dividing the $k_a$ by the $k_d$.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

The term "condition" as used herein refers generally to a disease, event, or a change in health status. A change in health status may be associated with a particular disease or event, in which case the change may occur simultaneously with or in advance of the disease or event. In those cases where the change in health status occurs in advance of a disease or event, the change in health status may serve as a predictor of the disease or event. For example, a change in health status may be an alteration in the expression level of a particular gene associated with a disease or event. Alternatively, a change in health status may not be associated with a particular disease or event.

The terms "treat," "treating," or "treatment" as used herein generally refer to preventing a condition or event, slowing the onset or rate of development of a condition or delaying the occurrence of an event, reducing the risk of developing a condition or experiencing an event, preventing or delaying the development of symptoms associated with a condition or event, reducing or ending symptoms associated with a condition or event, generating a complete or partial regression of a condition, lessening the severity of a condition or event, or some combination thereof.

An "effective amount" or "therapeutically effective amount" as used herein refers to an amount effective, at dosages and for periods of time necessary, to achieve a desired therapeutic result. A therapeutically effective amount of a disclosed capture agent may vary according to factors such as the disease state, age, sex, and weight of the individual, and the ability of the capture agent to elicit a desired response in the individual.

The term "stable" as used herein with regard to a capture agent protein catalyzed capture agent or pharmaceutical formulation thereof refers to the agent or formulation retaining structural and functional integrity for a sufficient period of time to be utilized in the methods described herein.

The term "synthetic" as used herein with regard to a protein catalyzed capture agent or capture agent refers to the capture agent has been generated by chemical rather than biological means.

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "substantially identical" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

In certain embodiments, the term "IL-17F" as used herein refers to human IL-17F. In some embodiments, IL-17 comprises the following amino acid sequence or an amino acid sequence substantially identical to it.

(SEQ ID NO: 31)

```
1   MTVKTLHGPA MVKYLLLSIL GLAFLSEAAA RKIPKVGHTF FQKPESCPPV PGGSMKLDIG

61  IINENQRVSM SRNIESRSTS PWNYTVTWDP NRYPSEVVQA QCRNLGCINA QGKEDISMNS

121 VPIQQETLVV RRKHQGCSVS FQLEKVLVTV GCTCVTPVIH RVQ
```

In other embodiments, IL-17F is a protein encoded by the gene represented by Entrez Gene ID Number 112744.

Development of IL-17F Capture Agents

Antibodies are currently the default detection agent for use in diagnostic platforms. However, antibodies possess several disadvantages, including high cost, poor stability, and, in many cases, lack of proper characterization and high specificity. The ideal replacement for use in diagnostic assays should be synthetic, stable to a range of thermal and chemical conditions, and display high affinity and specificity for the target of interest.

A high quality monoclonal antibody possesses low-nanomolar affinity and high target specificity. Interestingly, structural and genetic analyses of the antigen recognition surface have shown that the majority of the molecular diversity of the variable loops is contained in a single highly variable loop (CDR-H3). In humans, this loop ranges in size from 1-35 residues (15 on average), can adopt a wide range of structural conformations, and is responsible for most of the interactions with the antigen. The other five loops are significantly less diverse and adopt only a handful of conformations. This suggests that a carefully selected "anchor" peptide can dominate the mode and strength of the interaction between a capture agent and its target protein. It also suggests that other peptide components, while providing only modest contributions to the total interaction energy, can supply important scaffolding features and specificity elements.

In situ click chemistry is a technique in which a small molecule enzymatic inhibitor is separated into two moieties, each of which is then expanded into a small library—one containing acetylene functionalities, and the other containing azide groups. The enzyme itself then assembles the 'best fit' inhibitor from these library components by selectively promoting 1,3-dipolar cycloaddition between the acetylene and azide groups to form a triazole linkage (the 'click' reaction). The protein effectively plays the role of an extremely selective variant of the Cu(I) catalyst that is commonly used for such couplings. The enzyme promotes the click reaction only between those library components that bind to the protein in the right orientation. The resultant inhibitor can exhibit far superior affinity characteristics relative to the initial inhibitor that formed the basis of the two libraries.

Sequential in situ click chemistry extends the in situ click chemistry concept to enable the discovery of multiligand capture agents (see: USSN 20100009896, incorporated herein by reference). This process was used previously to produce a triligand capture agent against the model protein carbonic anhydrase II (CAII). Sequential in situ click chemistry has several advantages. First, structural information about the protein target is replaced by the ability to sample a very large chemical space to identify the ligand components of the capture agent. For example, an initial ligand may be identified by screening the protein against a large (>106 element) one-bead-one-compound (OBOC) peptide library, where the peptides themselves may be comprised of natural, non-natural, and/or artificial amino acids. The resultant anchor ligand is then utilized in an in situ click screen, again using a large OBOC library, to identify a biligand binder. A second advantage is that the process can be repeated, so that the biligand is used as an anchor to identify a triligand, and so forth. The final capture agent can then be scaled up using relatively simple and largely automated chemistries, and it can be developed with a label, such as a biotin group, as an intrinsic part of its structure. This approach permits the exploration of branched, cyclic, and linear capture agent architectures. While many strategies for protein-directed multiligand assembly have been described, most require detailed structural information on the target to guide the screening strategy, and most (such as the original in situ click approach), are optimized for low-diversity small molecule libraries.

The present embodiment further generalizes the in situ click application to naively find an anchor ligand using in situ click. In previous approaches, a known binder was necessary to begin the ligand. This method provides a mechanism to find an anchor ligand de novo.

As described herein, an iterative in situ click chemistry approach was utilized to synthesize a biligand capture agent that specifically binds IL-17F. This in situ click chemistry approach comprised two steps. First, two "anchor" ligands were found that bound IL-17F at distinct but relatively close sites. Second, a linker of an appropriate size was found that bound the two ligands producing a capture agent with higher affinity for IL-17F.

The capture agents generated by the methods disclosed herein were found to display binding affinity for IL-17F. The capture agents were shown to function as both capture and detection agents in ELISA assays and efficiently immunoprecipitate IL-17F.

IL-17F Capture Agents

In one aspect, provided herein is a stable, synthetic capture agent that specifically binds IL-17F, wherein the capture agent comprises two or more "anchor" ligands (also referred to as simply "ligands" herein) and a linker and wherein the ligands selectively bind IL-17F.

In certain embodiments, a ligand comprises one or more polypeptides or peptides. In certain of these embodiments, a target-binding moiety comprises one or more peptides comprising D-amino acids, L-amino acids, and/or amino acids substituted with functional groups selected from the group consisting of substituted and unsubstituted alkyl, substituted and unsubstituted azido, substituted and unsubstituted alkynyl, substituted and unsubstituted biotinyl, substituted and unsubstituted azioalkyl, substituted and unsubstituted polyethyleneglycolyl, and substituted and unsubstituted 1,2,3-triazole.

In certain embodiments, the ligands are linked to one another via a covalent linkage through a linker. In certain of these embodiments, the ligand and linker are linked to one another via an amide bond or a 1,4-disubstituted-1,2,3-triazole linkage as shown below:

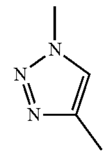

1,4-disubstituted-1,2,3-triazole linkage.

In those embodiments where the ligands and linker are linked to one another via a 1,4-disubstituted-1,2,3-triazole linkage, the 1,4-disubstituted-1,2,3-triazole linkage may be formed by Cu-Catalyzed Azide/Alkyne Cycloaddition (CuAAC).

In certain embodiments, the ligands and linker are linked to one another by a Tz4 linkage having the following structure:

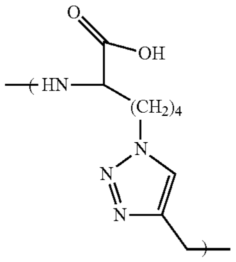

In certain embodiments, the ligands and linker are linked to one another by a Tz5 linkage having the following structure:

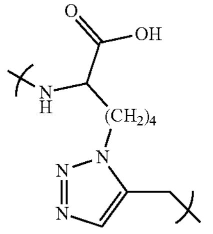

In those embodiments wherein one or more of the ligands and linker are linked to one another via amide bonds, the amide bond may be formed by coupling a carboxylic acid group and an amine group in the presence of a coupling agent (e.g., 0-(7-azabenzotriazol-1-yl)-N,N,N',N'-tetramethyluronium hexafluorophosphate (HATU), N-hydroxy-7-aza-benzotriazole (HOAt), or diisopropylethylamine (DIEA) in DMF).

In certain embodiments, the capture agents provided herein are stable across a range of reaction conditions and/or storage times. A capture agent that is "stable" as used herein maintains the ability to specifically bind to a target protein. In certain embodiments, the capture agents provided herein are more stable than an antibody binding to the same target protein under one or more reaction and/or storage conditions. For example, in certain embodiments the capture agents provided herein are more resistant to proteolytic degradation than an antibody binding to the same target protein.

In certain embodiments, the capture agents provided herein have a shelf-life of greater than six months, meaning that they are stable in storage for greater than six months. In certain of these embodiments, the capture agents have a shelf-life of one year or greater, two years or greater, or more than three years. In certain of these embodiments, the capture agents are stored as a lyophilized powder. In certain embodiments, the capture agents provided herein have a longer shelf-life than an antibody binding to the same target protein.

In certain embodiments, the capture agents provided herein are stable at temperatures ranging from about −80° to about 120° C. In certain of these embodiments, the capture agents are stable within a temperature range of −80° to −40° C.; −40° to −20° C.; −20° to 0° C.; 0° to 20° C.; 20° to 40° C.; 40° to 60° C.; 60° to 80° C.; and/or 80° to 120° C. In certain embodiments, the capture agents provided herein are stable across a wider range of temperatures than an antibody binding to the same target protein, and/or remain stable at a specific temperature for a longer time period than an antibody binding to the same target protein.

In certain embodiments, the capture agents provided herein are stable at a pH range from about 3.0 to about 8.0. In certain embodiments, the range is about 4.0 to about 7.0. In certain embodiments, the range is about 7.0 to about 8.0.

In certain embodiments, the capture agents provided herein are stable in human serum for more than 12 hours. In certain of these embodiments, the capture agents are stable in human serum for more than 18 hours, more than 24 hours, more than 36 hours, or more than 48 hours. In certain embodiments, the capture agents provided herein are stable for a longer period of time in human serum than an antibody binding to the same target protein. In certain embodiments, the capture agents are stable as a powder for two months at a temperature of about 60° C.

In certain embodiments, the capture agents provided herein may comprise one or more detection labels, including for example biotin, copper-1,4,7,10-tetraazacyclododecane-1,4,7,10-tetraacetic acid (copper-DOTA), $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, 11C, $^{76}$Br, $^{123}$I, $^{131}$I, $^{67}$Ga, $^{111}$In and $^{99m}$Tc, or other radiolabeled products that may include gamma emitters, proton emitters, positron emitters, tritium, or covered tags detectable by other methods (i.e., gadolinium) among others. In a particular embodiment, the detection label is $^{18}$F. In certain embodiments, the capture agents may be modified to be used as imaging agents. The imaging agents may be used as diagnostic agents.

In certain embodiments, the capture agents provided herein may be modified to obtain a desired chemical or biological activity. Examples of desired chemical or biological activities include, without limitation, improved solubility, stability, bioavailability, detectability, or reactivity. Examples of specific modifications that may be introduced to a capture agent include, but are not limited to, cyclizing the capture agent through formation of a disulfide bond; modifying the capture agent with other functional groups or molecules. Similarly, a capture agent may be synthesized to bind to non-canonical or non-biological epitopes on proteins, thereby increasing their versatility. In certain embodiments, the capture agent may be modified by modifying the synthesis blocks of the target-binding moieties before the coupling reaction.

Methods of Making/Screening Capture Agents

Provided herein in certain embodiments are methods of screening target-binding moieties and/or making capture agents that comprise these target-binding moieties. Methods for screening target-binding moieties and/or making capture agents that comprise these target-binding moieties can also be found in International Publication Nos. WO 2012/106671, WO 2013/033561, WO 2013/009869 and WO 2014/074907, each of which is incorporated by reference, herein, in their entireties.

In certain embodiments, two separately-identified ligands that bind to two different regions of the same protein (the target) are chemically linked together to form a biligand. By optimizing a linker of the two ligands, the biligand formed by the ligands and linker can exhibit a binding affinity that is far superior to either of the individual ligands. This enhanced binding effect is called binding cooperativity. For an ideal cooperative binder, the thermodynamic binding energies of the individual ligands to the target will sum to yield the binding energy of the linked biligand. This means that the binding affinity constant ($K_D$) of the linked biligand will be the product of the binding affinity of the individual ligands (i.e. $K_D=K_{D1}\times K_{D2}$, where the subscripts 1 and 2 refer to the two ligands). In practice, full cooperative binding is rarely, if ever, achieved. Thus, a comparison of the properties of a linked biligand against those of a fully cooperative binder provides a measurement of how optimally the two ligands were linked.

If the protein target has a known and well-defined tertiary (folded) structure, then key aspects of this targeting method involve strategies for identifying ligands that bind to preferred regions of the protein, followed by approaches for identifying an optimized linker. If the protein does not have a well-defined tertiary structure, the disclosure describes strategies designed to still achieve a significant measure of cooperative binding from a biligand.

Figure 7:
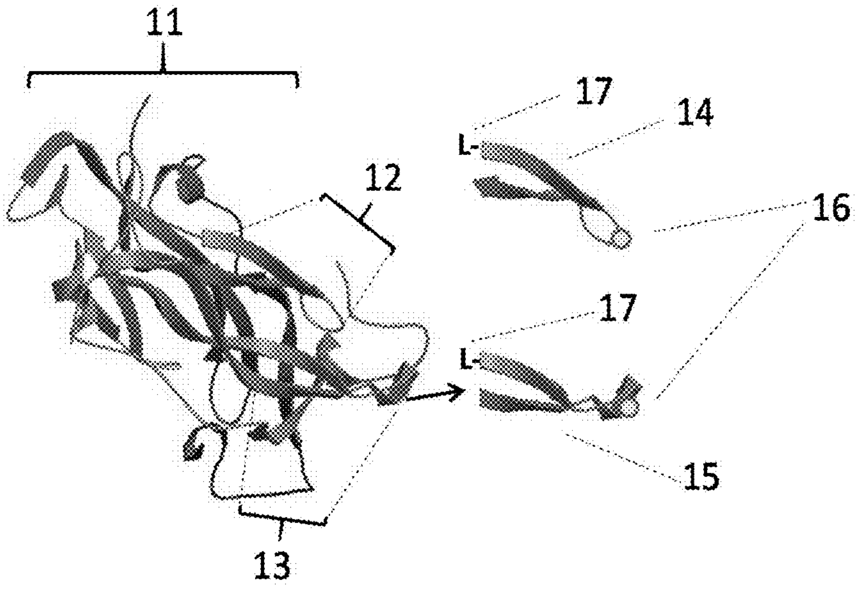
FIG. 7: Starting point for developing a set of PCC binders against a protein target. The initial goal is to identify one or more PCCs that bind to one epitope on the protein target (12), and one or more different PCCs binding to a second epitope (13). Additional PCCs that bind to a third, fourth, etc., epitope may be useful as well. The epitope targeted PCC method teaches that this may be accomplished by screening peptide libraries against synthetic epitopes (SynEps) (14, 15). A SynEp is a polypeptide that has the sequence of the naturally occurring target epitope, except that one position contains an artificial amino acid that presents an azide or acetylene chemical group (16), called a click handle. The SynEp is further modified to contain an assay handle, such as a biotin group, at the N- or C-terminus (17). The screening procedure has been described previously (Das, S. et al., A General Synthetic Approach for Designing Epitope Targeted Macrocyclic Peptide Ligands. Angew.

FIG. 7 describes the starting point for developing a set of PCC binders against a protein target (11). The initial goal is to identify one or more PCCs that bind to one epitope on the protein target (12), and one or more different PCCs binding to a second epitope (13). Additional PCCs that bind to a third, fourth, etc., epitope may be useful as well. The epitope targeted PCC method teaches that this may be accomplished by screening peptide libraries against synthetic epitopes (SynEps) such as those shown in FIG. 7 (14, 15). A SynEp is a polypeptide that has the sequence of the naturally occurring target epitope, except that one position contains an artificial amino acid that presents an azide or acetylene chemical group (16), called a click handle. The SynEp is further modified to contain an assay handle, such as a biotin group, at the N- or C-terminus (17). The screening procedure can be done using any procedure disclosed herein or known in the art. By screening, one identifies at least one unique peptide binder to each of at least two epitopes on the target. Those peptide binders are validated via carrying out binding assays against the full protein target (11) as well as against the SynEps. For those binding assays, the SynEps are prepared with the naturally occurring residue in place of the click handle (16).

Ideally, the different regions of the target protein to which the different ligands bind will be relatively close together (a few nanometers or less) in the tertiary protein structure. For even a single SynEp, a screen can produce PCCs that bind to two different sites. In FIG. 8, the region representing the epitope of interest (12) is highlighted against a dimmer background of the full protein (11). The amino acid residue that was substituted for a click handle in the SynEp structure is indicated by a star (22). During the SynEp screening steps, PCCs that bind to the N-terminal side of the epitope (23) or the C-terminal side (24) may both be identified.

Once the epitope targeted PCCs are identified, there are several methods for selecting a linker.

In a first embodiment, if the folded structure of the protein is known, and if the PCCs bind to that folded structure, then one can use that information, plus knowledge of which PCCs bind to which epitopes, to estimate an optimal linker length. This is illustrated in FIG. 9. This figure shows one PCC (31) that binds to the N-side of one epitope (12) and a second PCC (32) binding to the C-side of a second epitope (13). Analysis of this binding arrangement, together with the structure of the protein from, for example, the Protein Database, permits an estimate of the length of an optimized linker (33). Such an estimate can narrow down the choice of candidate linkers to a very small number. One example might be to use such a length estimate to select one or two length-matched polyethylene glycol oligomers for testing. The best linker (34) is the one that brings the biligand affinity closest to that a fully cooperative binder.

In a second embodiment, if the folded structure of the protein is not known, or if the protein simply does not have a well-defined folded structure, then one uses as much information as is available to determine the composition of a library of candidate linker molecules. That library is then screened to identify a best linker.

In a third embodiment, if the folded structure of the protein is not known or if the protein simply does not have a well-defined folded structure, then, using what knowledge about the protein does exist, simply select a linker to append the two PCCs. Even if an optimized, fully cooperative binder is not identified in this way, the linked biligand will almost certainly outperform either of the two monoligands because of cooperativity effects.

In Vitro

For detection of IL-17F in solution, a capture agent of the invention can be detectably labeled, then contacted with the solution, and thereafter formation of a complex between the capture agent and the IL-17F target can be detected. As an example, a fluorescently labeled capture agent can be used for in vitro IL-17F detection assays, wherein the capture agent is added to a solution to be tested for IL-17F under conditions allowing binding to occur. The complex between the fluorescently labeled capture agent and the IL-17F target can be detected and quantified by, for example, measuring the increased fluorescence polarization arising from the complex-bound peptide relative to that of the free peptide.

Alternatively, a sandwich-type "ELISA" assay can be used, wherein a capture agent is immobilized on a solid support such as a plastic tube or well, then the solution suspected of containing IL-17F is contacted with the immobilized binding moiety, non-binding materials are washed away, and complexed polypeptide is detected using a suitable detection reagent for recognizing IL-17F.

For detection or purification of soluble IL-17F from a solution, capture agents of the invention can be immobilized on a solid substrate such as a chromatographic support or other matrix material, then the immobilized binder can be loaded or contacted with the solution under conditions suitable for formation of a capture agent/IL-17F complex. The non-binding portion of the solution can be removed and the complex can be detected, for example, using an anti-IL-17F antibody, or an anti-binding polypeptide antibody, or the IL-17F can be released from the binding moiety at appropriate elution conditions.

In Vivo Diagnostic Imaging

A particularly preferred use for the capture agents of the invention is for creating visually readable images of IL-17F or IL-17F-expressing cells in a biological fluid, such as, for example, in human serum. The IL-17F capture agents disclosed herein can be converted to imaging reagents by conjugating the capture agents with a label appropriate for diagnostic detection. Preferably, a capture agent exhibiting much greater specificity for IL-17F than for other serum proteins is conjugated or linked to a label appropriate for the detection methodology to be employed. For example, the capture agent can be conjugated with or without a linker to a paramagnetic chelate suitable for Magnetic Resonance Imaging (MRI), with a radiolabel suitable for x-ray, Positron Emission Tomography (PET), Single Photon Emission Computed Tomography (SPECT) or scintigraphic imaging (including a chelator for a radioactive metal), with an ultrasound contrast agent (e.g., a stabilized microbubble, a microballoon, a microsphere or what has been referred to as a gas filled "liposome") suitable for ultrasound detection, or with an optical imaging dye.

In another embodiment, rather than directly labeling a capture agent with a detectable label or radiotherapeutic construct, one or more peptides or constructs of the invention can be conjugated with for example, avidin, biotin, or an antibody or antibody fragment that will bind the detectable label or radiotherapeutic.

A. Magnetic Resonance Imaging

The IL-17F capture agents described herein can advantageously be conjugated with a paramagnetic metal chelate in order to form a contrast agent for use in MRI.

Preferred paramagnetic metal ions have atomic numbers 21-29, 42, 44, or 57-83. This includes ions of the transition metal or lanthanide series which have one, and more preferably five or more, unpaired electrons and a magnetic moment of at least 1.7 Bohr magneton. Preferred paramagnetic metals include, but are not limited to, chromium (III), manganese (H), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III), chromium (III), iron (III), and gadolinium (III). The trivalent cation, Gd3+, is particularly preferred for MRI contrast agents, due to its high relaxivity and low toxicity, with the further advantage that it exists in only one biologically accessible oxidation state, which minimizes undesired metabolysis of the metal by a patient. Another useful metal is Cr3+, which is relatively inexpensive. Gd(III) chelates have been used for clinical and radiologic MR applications since 1988, and approximately 30% of MRI exams currently employ a gadolinium-based contrast agent.

The paramagnetic metal chelator is a molecule having one or more polar groups that act as a ligand for, and complex with, a paramagnetic metal. Suitable chelators are known in the art and include acids with methylene phosphonic acid groups, methylene carbohydroxamine acid groups, carboxyethylidene groups, or carboxymethylene groups. Examples of chelators include, but are not limited to, diethylenetriaminepentaacetic acid (DTPA), 1,4,7,10-tetraazacyclo-tetradecane-1,4,7,10-tetraacetic acid (DOTA), 1-substituted 1,4,7-tricarboxymethyl-1,4,7,10-teraazacyclododecane (DO3A), ethylenediaminetetraacetic acid (EDTA), and 1,4,8,11-tetra-azacyclotetradecane-1,4,8,11-tetraacetic acid (TETA). Additional chelating ligands are ethylene bis-(2-hydroxy-phenylglycine) (EHPG), and derivatives thereof, including 5-CI-EHPG, 5-Br-EHPG, 5-Me-EHPG, 5-t-Bu-EHPG, and 5-sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-2 (hydroxybenzyl)-ethylene-diaminediacetic acid (HBED) and derivatives thereof; the class of macrocyclic compounds which contain at least 3 carbon atoms, more preferably at least 6, and at least two heteroatoms (0 and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N"-triacetic acid, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4,8,11-tetraazacyclotetradecane-1,4,8,11-(methyl tetraacetic acid); derivatives of 1,3-propylene-diaminetetraacetic acid (PDTA) and triethylenetetraaminehexaacetic acid (TTNA); derivatives of 1,5,10-N,N',N"-tris(2,3-dihydroxybenzoyl)-tricatecholate (LICAM); and 1,3,5-N,M,N"-tris(2,3-dihydroxybenzoyDatninomethylbenzene (MECAM). A preferred chelator for use in the present invention is DTPA, and the use of DO3A is particularly preferred. Examples of representative chelators and chelating groups contemplated by the present invention are described in WO 98/18496, WO 86/06605, WO 91/03200, WO 95/28179, WO 96/23526, WO 97/36619, PCT/US98/01473, PCT/US98/20182, and U.S. Pat. Nos. 4,899,755, 5,474,756, 5,846,519 and 6,143,274, all of which are hereby incorporated by reference.

In accordance with the present invention, the chelator of the MRI contrast agent is coupled to the IL-17F capture agent. The positioning of the chelate should be selected so as not to interfere with the binding affinity or specificity of the IL-17F capture agent. The chelate also can be attached anywhere on the capture agent.

In general, the IL-17F capture agent can be bound directly or covalently to the metal chelator (or other detectable label), or it can be coupled or conjugated to the metal chelator using a linker, which can be, without limitation, amide, urea, acetal, ketal, double ester, carbonyl, carbamate, thiourea, sulfone, thioester, ester, ether, disulfide, lactone, imine, phosphoryl, or phosphodiester linkages; substituted or unsubstituted saturated or unsaturated alkyl chains; linear, branched, or cyclic amino acid chains of a single amino acid or different amino acids (e.g., extensions of the N- or C-terminus of the IL-17F binding moiety); derivatized or underivatized polyethylene glycols (PEGs), polyoxyethylene, or polyvinylpyridine chains; substituted or unsubstituted polyamide chains; derivatized or underivatized polyamine, polyester, polyethylenimine, polyacrylate, poly (vinyl alcohol), polyglycerol, or oligosaccharide (e.g., dextran) chains; alternating block copolymers; malonic, succinic, glutaric, adipic and pimelic acids; caproic acid; simple diamines and dialcohols; any of the other linkers disclosed herein; or any other simple polymeric linkers known in the art (see, for example, WO 98/18497 and WO 98/18496). Preferably the molecular weight of the linker can be tightly controlled. The molecular weights can range in size from less than 100 to greater than 1000. Preferably the molecular weight of the linker is less than 100. In addition, it can be desirable to utilize a linker that is biodegradable in vivo to provide efficient routes of excretion for the imaging reagents of the present invention. Depending on their location within the linker, such biodegradable functionalities can include ester, double ester, amide, phosphoester, ether, acetal, and ketal functionalities.

In general, known methods can be used to couple the metal chelate and the IL-17F capture agent using such linkers (WO 95/28967, WO 98/18496, WO 98/18497 and discussion therein). The IL-17F binding moiety can be linked through an N- or C-terminus via an amide bond, for example, to a metal coordinating backbone nitrogen of a metal chelate or to an acetate arm of the metal chelate itself. The present disclosure contemplates linking of the chelate on any position, provided the metal chelate retains the ability to bind the metal tightly in order to minimize toxicity.

MRI contrast reagents prepared according to the disclosures herein can be used in the same manner as conventional MRI contrast reagents. Certain MR techniques and pulse sequences can be preferred to enhance the contrast of the site to the background blood and tissues. These techniques include (but are not limited to), for example, black blood angiography sequences that seek to make blood dark, such as fast spin echo sequences (Alexander, A. et al., 1998. Magn. Reson. Med., 40: 298-310) and flow-spoiled gradient echo sequences (Edelman, R. et al., 1990. Radiology, 177: 45-50). These methods also include flow independent techniques that enhance the difference in contrast, such as inversion-recovery prepared or saturation-recovery prepared sequences that will increase the contrast between IL-17F-expressing tissue and background tissues. Finally, magnetization transfer preparations also can improve contrast with these agents (Goodrich, K. et al., 1996. Invest. Radia, 31: 323-32).

The labeled reagent is administered to the patient in the form of an injectable composition. The method of administering the MRI contrast agent is preferably parenterally, meaning intravenously, intraarterially, intrathecally, interstitially, or intracavitarilly. For imaging IL-17F-expressing tissues, such as tumors, intravenous or intraarterial administration is preferred. For MRI, it is contemplated that the subject will receive a dosage of contrast agent sufficient to enhance the MR signal at the site IL-17F expression by at least 10%. After injection with the IL-17F capture agent containing MRI reagent, the patient is scanned in the MRI machine to determine the location of any sites of IL-17F expression. In therapeutic settings, upon identification of a site of IL-17F expression (e.g., fluid or tissue), an anti-cancer agent (e.g., inhibitors of IL-17F) can be immediately administered, if necessary, and the patient can be subsequently scanned to visualize viral load.

B. Nuclear Imaging (Radionuclide Imaging) and Radiotherapy

The IL-17F capture agents of the invention can be conjugated with a radionuclide reporter appropriate for scintigraphy, SPECT, or PET imaging and/or with a radionuclide appropriate for radiotherapy. Constructs in which the IL-17F capture agents are conjugated with both a chelator for a radionuclide useful for diagnostic imaging and a chelator useful for radiotherapy are within the scope of the invention.

For use as a PET agent a disclosed capture agent may be complexed with one of the various positron emitting metal ions, such as $^{51}$Mn, $^{52}$Fe, $^{60}$Cu, $^{68}$Ga, $^{72}$As, $^{94m}$Tc, or $^{110}$In. The binding moieties of the invention can also be labeled by halogenation using radionuclides such as $^{18}$F, $^{124}$I, $^{125}$I, $^{131}$I, $^{123}$I, $^{77}$Br, and $^{76}$Br. Preferred metal radionuclides for scintigraphy or radiotherapy include $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117}$mSn, $^{149}$Pm, $^{161}$Tb, $^{177}$Lu, $^{198}$Au and $^{199}$Au. The choice of metal will be determined based on the desired therapeutic or diagnostic application. For example, for diagnostic purposes the preferred radionuclides include $^{64}$Cu, $^{67}$Ga, $^{68}$Ga, $^{99}$mTc, and $^{111}$In. For therapeutic purposes, the preferred radionuclides include $^{64}$Cu, $^{90}$Y, $^{105}$Rh, $^{111}$In, $^{117}$mSn, $^{149}$Pm, $^{153}$Sm, $^{161}$Tb, $^{166}$Tb, $^{166}$Dy, $^{166}$Ho, $^{175}$Yb, $^{177}$Ln, $^{186/188}$Re, and $^{199}$Au. $^{99m}$Tc is useful for diagnostic applications because of its low cost, availability, imaging properties, and high specific activity. The nuclear and radioactive properties of 99mTc make this isotope an ideal scintigraphic imaging agent. This isotope has a single photon energy of 140 keV and a radioactive half-life of about 6 hours, and is readily available from a $^{99}$Mo-$^{99}$mTc generator. $^{18}$F, 4-[$^{18}$F]fluorobenzaldehyde ($^{18}$FB), Al[$^{18}$F]-NOTA, $^{68}$Ga-DOTA, and $^{68}$Ga-NOTA are typical radionuclides for conjugation to IL-17F capture agents for diagnostic imaging.

The metal radionuclides may be chelated by, for example, linear, macrocyclic, terpyridine, and $N_3S$, $N_2S_2$, or $N_4$ chelants (see also, U.S. Pat. Nos. 5,367,080, 5,364,613, 5,021,556, 5,075,099, 5,886,142), and other chelators known in the art including, but not limited to, HYNIC, DTPA, EDTA, DOTA, DO3A, TETA, NOTA and bisamino bisthiol (BAT) chelators (see also U.S. Pat. No. 5,720,934). For example, N.sub.4 chelators are described in U.S. Pat. Nos. 6,143,274; 6,093,382; 5,608,110; 5,665,329; 5,656,254; and 5,688,487. Certain N.sub.35 chelators are described in PCT/CA94/00395, PCT/CA94/00479, PCT/CA95/00249 and in U.S. Pat. Nos. 5,662,885; 5,976,495; and 5,780,006. The chelator also can include derivatives of the chelating ligand mercapto-acetyl-acetyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in, for example, Liu, S, and Edwards, D., 1999. Chem. Rev., 99:2235-2268, and references therein.

The chelator also can include complexes containing ligand atoms that are not donated to the metal in a tetradentate array. These include the boronic acid adducts of technetium and rhenium dioximes, such as are described in U.S. Pat. Nos. 5,183,653; 5,387,409; and 5,118,797, the disclosures of which are incorporated by reference herein, in their entirety.

The chelators can be covalently linked directly to the IL-17F capture agent via a linker, as described previously, and then directly labeled with the radioactive metal of choice (see, WO 98/52618, U.S. Pat. Nos. 5,879,658, and 5,849,261).

IL-17F capture agents comprising $^{18}$F, 4-[$^{18}$F]fluorobenzaldehyde ($^{18}$FB), Al[$^{18}$F]-NOTA, $^{68}$Ga-DOTA, and $^{68}$Ga-NOTA are of preferred interest for diagnostic imaging. Complexes of radioactive technetium are also useful for diagnostic imaging, and complexes of radioactive rhenium are particularly useful for radiotherapy. In forming a complex of radioactive technetium with the reagents of this invention, the technetium complex, preferably a salt of $^{99m}$Tc pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with $^{99m}$Tc. Alternatively, the complex can be formed by reacting a peptide of this invention conjugated with an appropriate chelator with a pre-formed labile complex of technetium and another compound known as a transfer ligand. This process is known as ligand exchange and is well known to those skilled in the art. The labile complex can be formed using such transfer ligands as tartrate, citrate, gluconate or mannitol, for example. Among the $^{99m}$Tc pertechnetate salts useful with the present invention are included the alkali metal salts such as the sodium salt, or ammonium salts or lower alkyl ammonium salts.

Preparation of the complexes of the present invention where the metal is radioactive rhenium can be accomplished using rhenium starting materials in the +5 or +7 oxidation state. Examples of compounds in which rhenium is in the Re(VII) state are $NH_4ReO_4$ or $KReO_4$. Re(V) is available as, for example, $[ReOCl_4](NBu_4)$, $[ReOCl_4](AsPh_4)$, $ReOCl_3(PPh_3)_2$ and as $ReO_2(pyridine)^{4+}$, where Ph is phenyl and Bu is n-butyl. Other rhenium reagents capable of forming a rhenium complex also can be used.

Radioactively labeled PET, SPECT, or scintigraphic imaging agents provided by the present invention are encompassed having a suitable amount of radioactivity. Generally, the unit dose to be administered has a radioactivity of about 0.01 mCi to about 100 mCi, preferably 1 mCi to 20 mCi. The solution to be injected at unit dosage is from about 0.01 mL to about 10 mL. It is generally preferred to form radioactive complexes in solutions containing radioactivity at concentrations of from about 0.01 mCi to 100 mCi per mL.

Typical doses of a radionuclide-labeled IL-17F capture agent according to the invention provide 10-20 mCi. After injection of the radionuclide-labeled IL-17F capture agents into the patient, a gamma camera calibrated for the gamma ray energy of the nuclide incorporated in the imaging agent is used to image areas of uptake of the agent and quantify the amount of radioactivity present in the site. Imaging of the site in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos.

Proper dose schedules for the radiotherapeutic compounds of the present invention are known to those skilled in the art. The compounds can be administered using many methods including, but not limited to, a single or multiple IV or IP injections, using a quantity of radioactivity that is sufficient to cause damage or ablation of the targeted IL-17F-expressing tissue, but not so much that substantive damage is caused to non-target (normal tissue). The quantity and dose required is different for different constructs, depending on the energy and half-life of the isotope used, the degree of uptake and clearance of the agent from the body and the mass of the IL-17F-expressing tissue. In general, doses can range from a single dose of about 30-50 mCi to a cumulative dose of up to about 3 Ci.

The radiotherapeutic compositions of the invention can include physiologically acceptable buffers, and can require radiation stabilizers to prevent radiolytic damage to the compound prior to injection. Radiation stabilizers are known to those skilled in the art, and can include, for example, para-aminobenzoic acid, ascorbic acid, gentistic acid and the like.

A single, or multi-vial kit that contains all of the components needed to prepare the complexes of this invention, other than the radionuclide, is an integral part of this invention.

A single-vial kit preferably contains a chelating ligand, a source of stannous salt, or other pharmaceutically acceptable reducing agent, and is appropriately buffered with pharmaceutically acceptable acid or base to adjust the pH to a value of about 3 to about 9. The quantity and type of reducing agent used would depend on the nature of the exchange complex to be formed. The proper conditions are well known to those that are skilled in the art. It is preferred that the kit contents be in lyophilized form. Such a single vial kit can optionally contain labile or exchange ligands such as glucoheptonate, gluconate, mannitol, malate, citric or tartaric acid and can also contain reaction modifiers such as diethylenetriamine-pentaacetic acid (DPTA), ethylenediamine tetraacetic acid (EDTA), or alpha, beta, or gamma cyclodextrin that serve to improve the radiochemical purity and stability of the final product. The kit also can contain stabilizers, bulking agents such as mannitol, that are designed to aid in the freeze-drying process, and other additives known to those skilled in the art.

A multi-vial kit preferably contains the same general components but employs more than one vial in reconstituting the radiopharmaceutical. For example, one vial can contain all of the ingredients that are required to form a labile Tc(V) complex on addition of pertechnetate (e.g., the stannous source or other reducing agent). Pertechnetate is added to this vial, and after waiting an appropriate period of time, the contents of this vial are added to a second vial that contains the ligand, as well as buffers appropriate to adjust the pH to its optimal value. After a reaction time of about 5 to 60 minutes, the complexes of the present invention are formed. It is advantageous that the contents of both vials of this multi-vial kit be lyophilized. As above, reaction modifiers, exchange ligands, stabilizers, bulking agents, etc. can be present in either or both vials.

Also provided herein is a method to incorporate an 18F radiolabeled prosthetic group onto an IL-17F capture agent. In one embodiment, 4-[$^{18}$F]fluorobenzaldehyde ($^{18}$FB) is conjugated onto a capture agent bearing an aminooxy moiety, resulting in oxime formation. In another embodiment, [$^{18}$F]fluorobenzaldehyde is conjugated onto a capture agent bearing an acyl hydrazide moiety, resulting in a hydrazone adduct. 4-Fluorobenzaldehyde, can be prepared in $^{18}$F form by displacement of a leaving group, using $^{18}$F ion, by known methods.

$^{18}$F-labeled capture agents can also be prepared from capture agents possessing thiosemicarbazide moieties under conditions that promote formation of a thiosemicarbozone, or by use of a $^{18}$F-labeled aldehyde bisulfite addition complex.

The above methods are particularly amenable to the labeling of capture agents, e.g., the capture agents described herein, which can be modified during synthesis to contain a nucleophilic hydroxylamine, thiosemicarbazide or hydrazine (or acyl hydrazide) moiety that can be used to react with the labeled aldehyde. The methods can be used for any capture agent that can accommodate a suitable nucleophilic moiety. Typically the nucleophilic moiety is appended to the N-terminus of the peptide, but the skilled artisan will recognize that the nucleophile also can be linked to an amino acid side chain or to the peptide C-terminus. Methods of synthesizing a radiolabeled peptide sequence are provided in which 4-[$^{18}$F]fluorobenzaldehyde is reacted with a peptide sequence comprising either a hydroxylamine, a thiosemicarbazide or a hydrazine (or acyl hydrazide) group, thereby forming the corresponding oximes, thiosemicarbazones or hydrazones, respectively. The 4-[$^{18}$F]fluorobenzaldehyde typically is generated in situ by the acid-catalyzed decomposition of the addition complex of 4-[$^{18}$F]fluorobenzaldehyde and sodium bisulfite. The use of the bisulfite addition complex enhances the speed of purification since, unlike the aldehyde, the complex can be concentrated to dryness. Formation of the complex is also reversible under acidic and basic conditions. In particular, when the complex is contacted with a peptide containing a hydroxylamine, a thiosemicarbazide or a hydrazine (or acyl hydrazide) group in acidic medium, the reactive free 4-[$^{18}$F]fluorobenzaldehyde is consumed as it is formed in situ, resulting in the corresponding $^{18}$F radiolabeled peptide sequence.

In the instances when the oxime, thiosemicarbazone or hydrazone linkages present in vivo instability, an additional reduction step may be employed to reduce the double bond connecting the peptide to the $^{18}$F bearing substrate. The corresponding reduced peptide linkage would enhance the stability. One of skill in the art would appreciate the variety of methods available to carry out such a reduction step. Reductive amination steps as described in Wilson et al., Journal of Labeled Compounds and Radiopharmaceuticals, XXVIII (10), 1189-1199, 1990 may also be used to form a Schiffs base involving a peptide and 4-[$^{18}$F]fluorobenzaldehyde and directly reducing the Schiffs base using reducing agents such as sodium cyanoborohydride.

The 4-[$^{18}$F]fluorobenzaldehyde may be prepared as described in Wilson et al., Journal of Labeled Compounds and Radiopharmaceuticals, XXVIII (10), 1189-1199, 1990; Iwata et al., Applied radiation and isotopes, 52, 87-92, 2000; Poethko et al., The Journal of Nuclear Medicine, 45, 892-902, 2004; and Schottelius et al., Clinical Cancer Research, 10, 3593-3606, 2004. The Na18F in water may be added to a mixture of kryptofix and K.sub.2CO.sub.3. Anhydrous acetonitrile may be added and the solution is evaporated in a heating block under a stream of argon. Additional portions of acetonitrile may be added and evaporated to completely dry the sample. The 4-trimethylammoniumbenzaldehyde triflate may be dissolved in DMSO and added to the dried F-18. The solution may then be heated in the heating block. The solution may be cooled briefly, diluted with water and filtered through a Waters®. Oasis HLB LP extraction cartridge. The cartridge may be washed with 9:1 water:acetonitrile and water to remove unbound $^{18}$F and unreacted 4-trimethylammoniumbenzaldehyde triflate. The 4-[$^{18}$F]fluorobenzaldehyde may then be eluted from the cartridge with methanol in fractions.

Therapeutic Applications

Provided herein in certain embodiments are methods of using the IL-17F capture agents disclosed herein to identify, detect, quantify, and/or separate IL-17F in a biological sample. In certain embodiments, these methods utilize an immunoassay, with the capture agent replacing an antibody or its equivalent. In certain embodiments, the immunoassay may be a Western blot, pull-down assay, dot blot, or ELISA.

A biological sample for use in the methods provided herein may be selected from the group consisting of organs, tissue, bodily fluids, and cells. Where the biological sample is a bodily fluid, the fluid may be selected from the group consisting of blood, serum, plasma, urine, sputum, saliva, stool, spinal fluid, cerebral spinal fluid, lymph fluid, skin secretions, respiratory secretions, intestinal secretions, genitourinary tract secretions, tears, and milk. The organs include, e.g., the adrenal glands, bladder, bones, brain, breasts, cervix, esophagus, eyes, gall bladder, genitals, heart, kidneys, large intestine, liver, lungs, lymph nodes, ovaries, pancreas, pituitary gland, prostate, salivary glands, skeletal muscles, skin, small intestine, spinal cord, spleen, stomach, thymus gland, trachea, thyroid, testes, ureters, and urethra. Tissues include, e.g., epithelial, connective, nervous, and muscle tissues.

Provided herein in certain embodiments are methods of using the IL-17F capture agents disclosed herein to diagnose and/or classify (e.g., stage) a condition associated with IL-17F expression. In certain of these embodiments, the methods comprise (a) obtaining a biological sample from a subject; (b) measuring the presence or absence of IL-17F in the sample with the IL-17F capture agent; (c) comparing the levels of IL-17F to a predetermined control range for IL-17F; and (d) diagnosing a condition associated with IL-17F expression based on the difference between IL-17F levels in the biological sample and the predetermined control.

In other embodiments, the IL-17F capture agents disclosed herein are used as a mutant specific targeted therapeutic. In certain aspects of this embodiment, the IL-17F capture agent is administered alone without delivering DNA, a radiopharmaceutical or another active agent.

The IL-17F capture agents of the invention also can be used to target genetic material to IL-17F expressing cells. The genetic material can include nucleic acids, such as RNA or DNA, of either natural or synthetic origin, including recombinant RNA and DNA and antisense RNA and DNA. Types of genetic material that can be used include, for example, genes carried on expression vectors such as plasmids, phagemids, cosmids, yeast artificial chromosomes (YACs) and defective or "helper" viruses, antigene nucleic acids, both single and double stranded RNA and DNA and analogs thereof, such as phosphorothioate and phosphorodithioate oligodeoxynucleotides. Additionally, the genetic material can be combined, for example, with lipids, proteins or other polymers. Delivery vehicles for genetic material can include, for example, a virus particle, a retroviral or other gene therapy vector, a liposome, a complex of lipids (especially cationic lipids) and genetic material, a complex of dextran derivatives and genetic material, etc.

In an embodiment the capture agents of the invention are utilized in gene therapy. In this embodiment, genetic material, or one or more delivery vehicles containing genetic material can be conjugated to one or more IL-17F capture agents of this disclosure and administered to a patient.

Therapeutic agents and the IL-17F capture agents disclosed herein can be linked or fused in known ways, optionally using the same type of linkers discussed elsewhere in this application. Preferred linkers will be substituted or unsubstituted alkyl chains, amino acid chains, polyethylene glycol chains, and other simple polymeric linkers known in the art. More preferably, if the therapeutic agent is itself a protein, for which the encoding DNA sequence is known, the therapeutic protein and IL-17F binding polypeptide can be coexpressed from the same synthetic gene, created using recombinant DNA techniques, as described above. The coding sequence for the IL-17F binding polypeptide can be fused in frame with that of the therapeutic protein, such that the peptide is expressed at the amino- or carboxy-terminus of the therapeutic protein, or at a place between the termini, if it is determined that such placement would not destroy the required biological function of either the therapeutic protein or the IL-17F binding polypeptide. A particular advantage of this general approach is that concatamerization of multiple, tandemly arranged IL-17F capture agents is possible, thereby increasing the number and concentration of IL-17F binding sites associated with each therapeutic protein. In this manner, IL-17F binding avidity is increased, which would be expected to improve the efficacy of the recombinant therapeutic fusion protein.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLES

Example 1. IL-17F Epitope Design

Figures 1A, 1B, 1C:
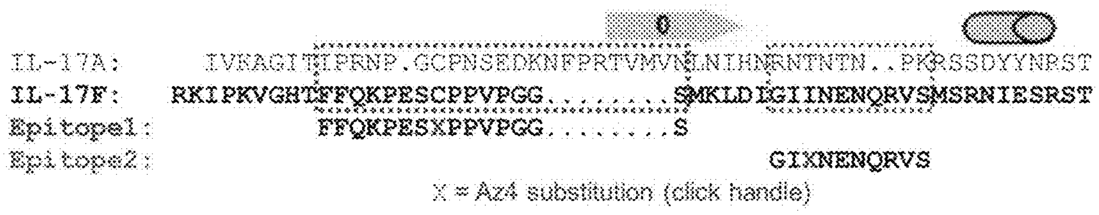
FIGS. 1A-1C: Epitopes derived from the IL-17F protein.

The primary sequences of IL-17F and IL-17A were examined to understand where there are regions of identity or similarity, and where there are differences. To create macrocyclic peptide ligands that can effectively discriminate IL-17F from IL-17A, attention was placed on those sequences that are unique to the two proteins. Sequence differences that discriminate IL-17F from IL-17A were found to occur in the N-terminal region of the mature proteins. In IL-17F, this region of uniqueness corresponds to Arg-31 to Thr-79 (FIG. 1A).

Two polypeptide epitopes were chemically synthesized and exploited as the targets for generating specific macrocyclic peptide ligands against IL-17F. Epitopes were designed with a biotin-$PEG_3$ assay handle and a strategically substituted azide click handle (Az4=L-azidolysine). The site of click handle substitution in each epitope was determined by examining the protein structure and identifying an amino acid (a) whose side chain is surface-exposed and does not interact with other atoms in the protein, and (b) that is chemically similar to Az4. IL-17F Epitope1 (Phe-40 to Ser-54) is located very close to the N-terminus of IL-17F, and is substituted with Az4 at a central location (Cys-48). IL-17F Epitope2 (Gly-60 to Ser-69) is found after Epitope1 in the primary sequence, and is substituted with Az4 at Ile-62. The sequences of Epitope1 and Epitope2 are shown in FIGS. 1B and C.

Example 2. Screening for Macrocycle Anchors Against IL-17F Epitope1

Screens were performed using a triazole-cyclized OBOC library of the form $H_2N$-Pra-Cy(XXXXX)-Met-TG (SEQ ID NO:34), where TG=TentaGel® S $NH_2$ resin (S 30 902, Rapp Polymere), X=one of seventeen L-amino acids (lacking Cys, Met, and Ile), Pra=L-propargylglycine, and Cy( )=triazole cyclization via flanking Pra and Az4 residues. Macrocycles were identified against the IL-17F Epitope1 fragment using a four-step screening process: 1) a pre-clear to eliminate non-specific binders, 2) a product screen to identify hits resulting from epitope-templated in situ click chemistry, 3) a target screen against His-tagged IL-17F protein, and 4) another target screen against His-tagged IL-17F protein in 2% (v/v) human serum to identify peptides whose binding to IL-17F is unperturbed by serum proteins.

Pre-Clear.

Swelled library beads (500 mg) were blocked overnight with Blocking Buffer (25 mM Tris-HCl, 150 mM NaCl, 1% (w/v) BSA, and 0.05% (v/v) Tween-20, pH 7.6) at 4° C., then washed with Blocking Buffer three times. A 1:10,000 dilution of Streptavidin-Alkaline Phosphatase (V559C, Promega) in 5 mL Blocking Buffer was added to the beads and incubated with gentle shaking at room temperature for 1 h. The beads were subsequently washed with 3×3 mL TBS (25 mM Tris-HCl, 150 mM NaCl, pH 7.6) (1 min ea), 3×3 mL 0.1 M glycine pH 2.8 wash buffer, 3×3 mL TBS, then 3×3 mL Alkaline Phosphatase buffer (100 mM Tris-HCl, 150 mM NaCl, 1 mM $MgCl_2$, pH 9) (5 min ea). Binding was visualized by incubating the beads in the presence of 5-bromo-4-chloro-3-indolyl phosphate/nitro blue tetrazolium (BCIP/NBT) substrate (S3771, Promega) for 25 min. Purple beads indicated background binders and were removed by pipet and discarded. The remaining clear beads were collected and stripped with 7.5 M guanidine hydrochloride pH 2.0 for 30 min, washed ten times with water, and incubated in 1-methyl-2-pyrrolidinone (NMP) overnight to decolorize.

Product Screen with IL-17F Epitope1.

Beads remaining from the pre-clear were washed with water ten times and TBS three times. Beads were then incubated with 3 mL of 100 µM IL-17F Epitope1 fragment (Biotin-$PEG_3$-FFQKPES (SEQ ID NO:1)[Az4]PPVPGGS (SEQ ID NO:32)) in TBS for 1.5 h at room temperature to allow for an in situ click reaction to occur. The beads were washed with TBS ten times and then incubated with 7.5 M guanidine hydrochloride pH 2.0 for 1 h to remove all IL-17F epitope not attached covalently to the beads. These beads were washed with TBS ten times and re-blocked with Blocking Buffer for 2 h. A 1:10,000 dilution of Streptavidin-Alkaline Phosphatase in 5 mL Blocking Buffer was added for 1 h to detect the presence of IL-17F epitope clicked to beads. The beads were subsequently washed with 3×3 mL TBS (1 min ea), 3×3 mL 0.1 M glycine pH 2.8 wash buffer, 3×3 mL TBS, then 3×3 mL Alkaline Phosphatase (pH 9) buffer (5 min ea). After this, the beads were developed with BCIP/NBT for 25 min as outlined in the pre-clear. Purple epitope-conjugated hit beads were selected by pipet and saved. These hits (25 total: 5 dark purple, 20 medium to light purple) were treated with 7.5 M guanidine hydrochloride pH 2.0 for 30 min to remove attached streptavidin, washed ten times with water, and incubated in NMP overnight to decolorize.

Target Screen with His-Tagged IL-17F Protein.

Product hits were washed with water ten times and stored in TBS at 4° C. These 25 beads were transferred to a Corning® 8162 Costar® Spin-X® centrifuge tube filter (cellulose acetate membrane) and incubated with Blocking Buffer for 3 h at room temperature. The beads were rinsed three times with Blocking Buffer and then incubated with 150 nM of full-length His-tagged IL-17F protein (ab167911, Abcam) in Blocking Buffer (preparation: 0.5 µL His-tagged IL-17F protein in 200 µL Blocking Buffer) for 1 h at room temperature. The beads were washed three times with Blocking Buffer and then incubated with 500 µL, of 1:10,000 Anti-6× His Tag® antibody [HIS-1] (Alkaline Phosphatase-conjugated) (ab49746, Abcam) in Blocking Buffer for 1 h at room temperature. The beads were subsequently washed with 3×500 µL Blocking Buffer, 3×500 µL TBS, then 3×500 µL Alkaline Phosphatase (pH 9) buffer (centrifuging at 7000 rpm for 30 sec after each wash). After this, the beads were developed with BCIP/NBT for 10 min. Purple hit beads bound to IL-17F protein were selected by pipet and saved. 20 beads were purple indicating binding to both the IL-17 epitope and protein, while 5 were clear indicating no binding to IL-17F protein. The 20 target hits were treated with 7.5 M guanidine hydrochloride pH 2.0 for 30 min to remove bound proteins, washed ten times with water, and incubated in NMP overnight to decolorize.

Target Screen with His-Tagged IL-17F Protein in 2% (v/v) Human Serum.

Target hits were washed with water ten times. These 20 beads were incubated with Blocking Buffer for 7 h in a Corning® 8162 Costar® Spin-X® centrifuge tube filter (cellulose acetate membrane). The beads were rinsed three times with Blocking Buffer and then incubated with 150 nM of full-length His-tagged IL-17F protein (ab167911, Abcam) in Blocking Buffer containing 2% (v/v) human serum (HS-30, Omega Scientific) for 1 h at room temperature (preparation: 1.25 µL His-tagged IL-17F protein+10 µL filtered serum+490 µL Blocking Buffer). Note: Before the screen, particulate matter was removed from serum by centrifugation (7000 rpm, 30 sec) using a Corning® 8162 Costar® Spin-X® tube filter. The beads were washed three times with Blocking Buffer and then incubated with 500 µL of 1:10,000

Anti-6x His Tag® antibody [HIS-1] (Alkaline Phosphatase-conjugated) (ab49746, Abcam) in Blocking Buffer for 1 h at room temperature. The beads were subsequently washed with 3×500 μL Blocking Buffer, 3×500 μL. TBS, then 3×500 μL Alkaline Phosphatase (pH 9) buffer (centrifuging at 7000 rpm for 30 sec after each wash). After this, the beads were developed with BCIP/NBT for 10 min. Purple hit beads were selected by pipet and saved. The 2 hits whose binding to IL-17F protein was unperturbed by serum proteins were treated with 7.5 M guanidine hydrochloride pH 2.0 for 30 min to remove bound proteins, washed ten times with water, and incubated in NMP overnight to decolorize. The 2 hits were finally washed with water ten times to prepare for sequencing analysis.

Sequencing was performed via Edman degradation on an Applied Biosystems Procise® cLC 2-cartridge system in the Protein/Peptide Micro Analytical Laboratory at Caltech. The Edman sequencer was unable to distinguish between 1) residues K (lysine) and L (leucine), and 2) residues Q (glutamine) and T (threonine). Sequencing results are shown in Table 1 including the K/L and Q/T variants.

TABLE 1

Sequences of macrocyclic peptide hits identified against IL-17F Epitope1

| | ×2 | ×3 | ×4 | ×5 | ×6 |
|---|---|---|---|---|---|
| hit1 | F | Y | K | T | H |
| | F | Y | K | Q | H |
| | F | Y | L | T | H |
| | F | Y | L | Q | H |
| hit2 | R | R | A | T | S |
| | R | R | A | Q | S |

These candidate peptides were re-synthesized on a cleavable resin, purified by reversed phase HPLC using a C18 column (Phenomenex Luna, 5 μm, 250×10 mm), and tested for affinity and specificity against the IL-17F protein by ELISA.

Synthesis Data for IL-17F Epitope1 Hits

Cy(FYKTH) (SEQ ID NO:5)-PEG$_3$-biotin. MALDI-MS (m/z): calcd. for $C_{65}H_{97}N_{17}O_{14}S$ (M+H) 1372.71; found 1374.24.

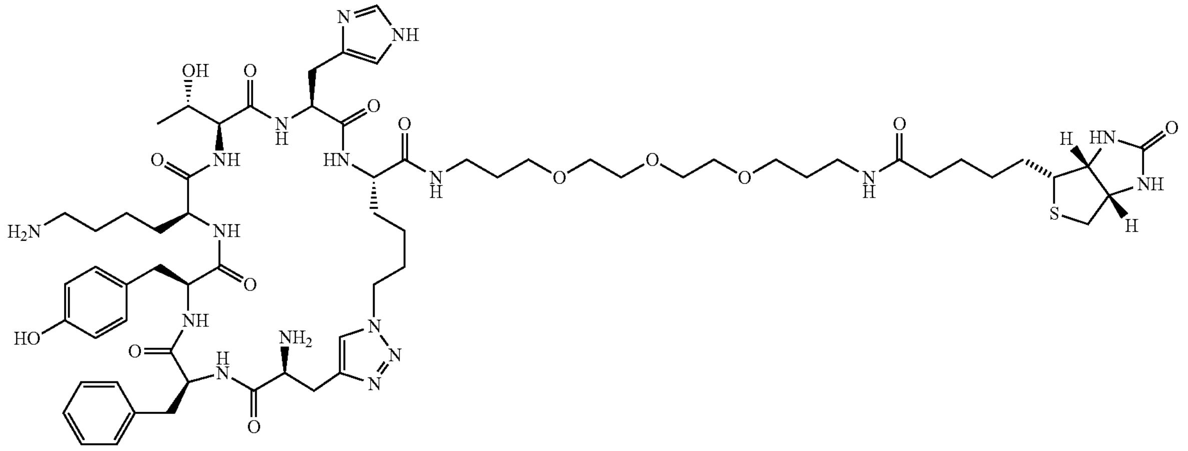

Cy(FYKQH) (SEQ ID NO:6)-PEG$_3$-biotin. MALDI-MS (m/z): calcd. for $C_{66}H_{98}N_{18}O_{14}S$ (M+H) 1399.72; found 1401.36.

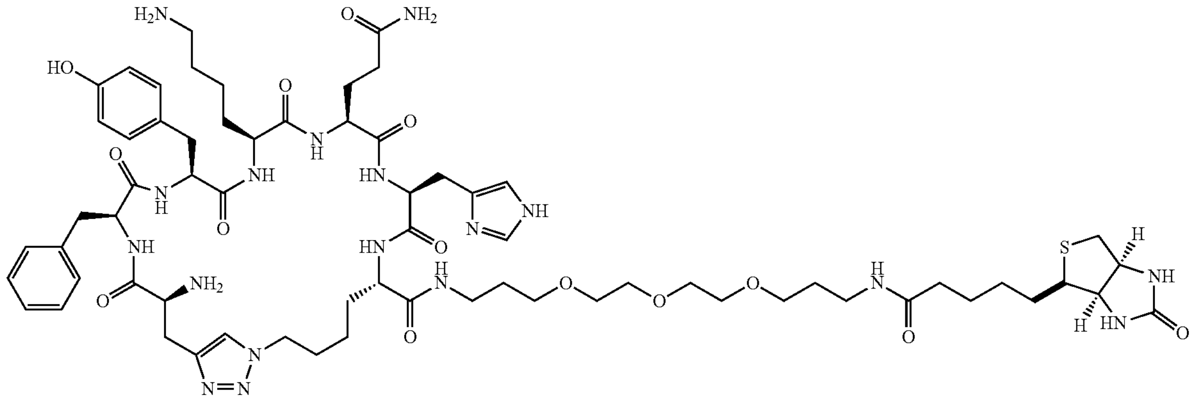

Cy(FYLTH) (SEQ ID NO:7)-PEG$_3$-biotin. MALDI-MS (m/z): calcd. for $C_{65}H96N_{16}O_{14}S$ (M+H) 1357.70; found 1360.15.
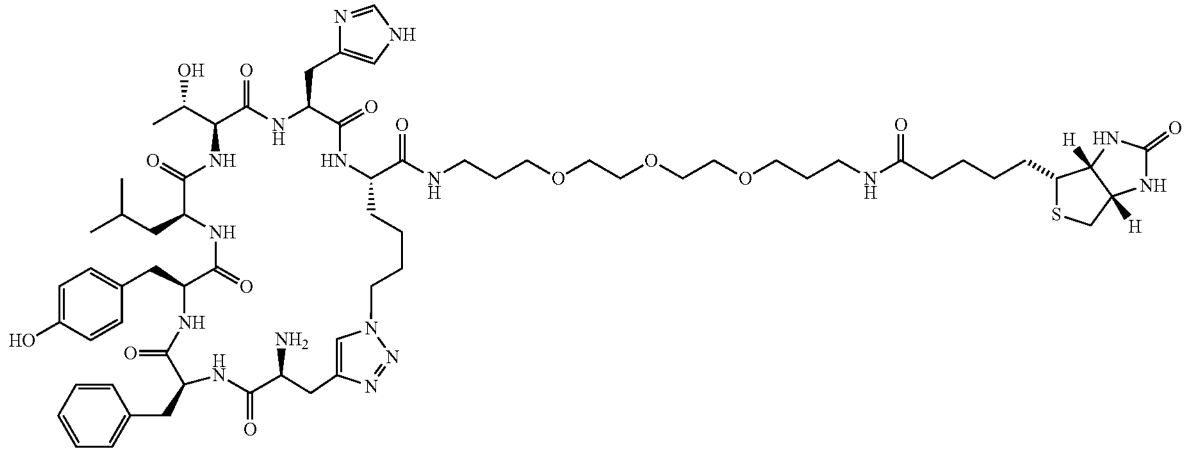
Cy(FYLQH) (SEQ ID NO:8)-PEG$_3$-biotin. MALDI-MS (m/z): calcd. for $C_{66}H_{97}N_{17}O_{14}S$ (M+H) 1384.71; found 1386.24.
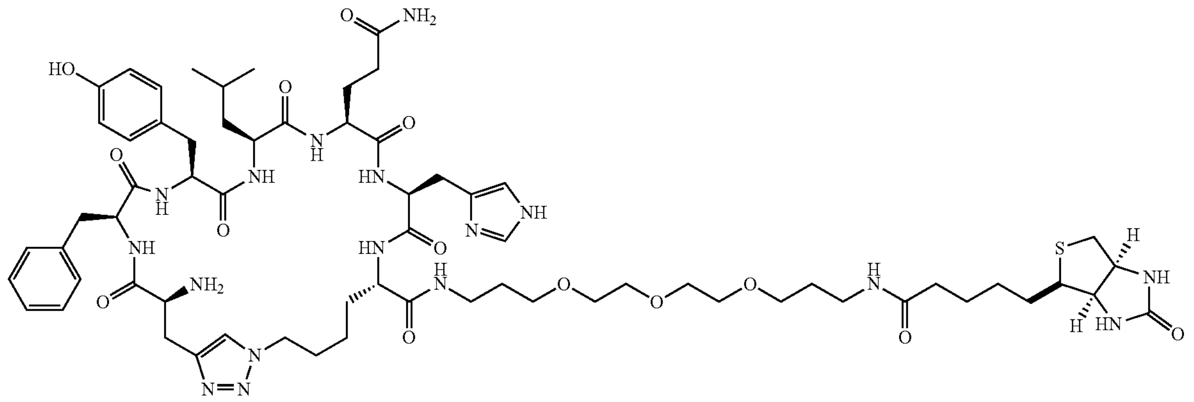
Cy(RRATS) (SEQ ID NO:9)-PEG$_3$-biotin. MALDI-MS (m/z): calcd. for $C_{53}H_{94}N_{20}O_{14}S$ (M+H) 1269.70; found 1269.91 (FIG. 2C).
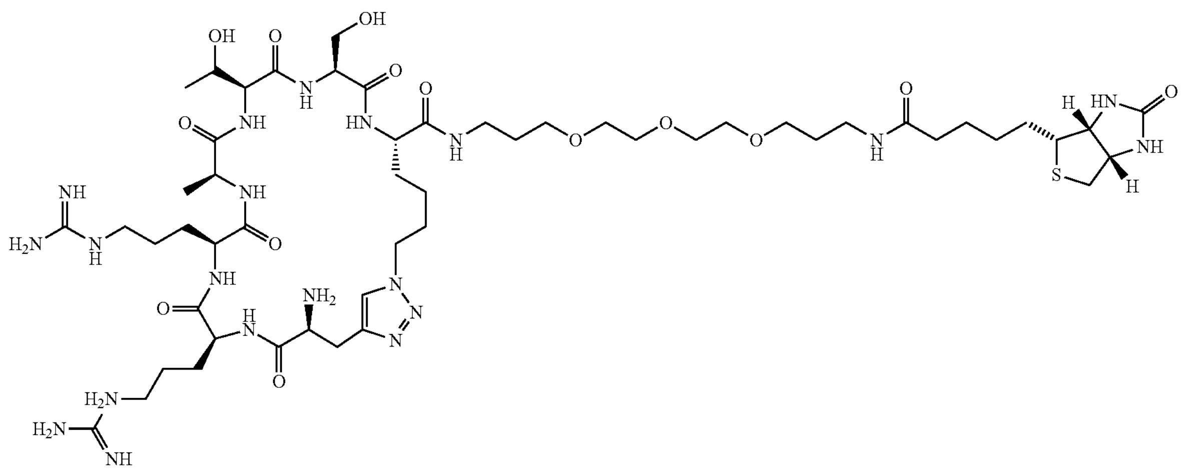

Cy(RRAQS) (SEQ ID NO:10)-$PEG_3$-biotin. MALDI-MS (m/z): calcd. for $C_{54}H_{95}N_{21}O_{14}S$ (M+H) 1295.71; found 1296.19 (FIG. 2D).

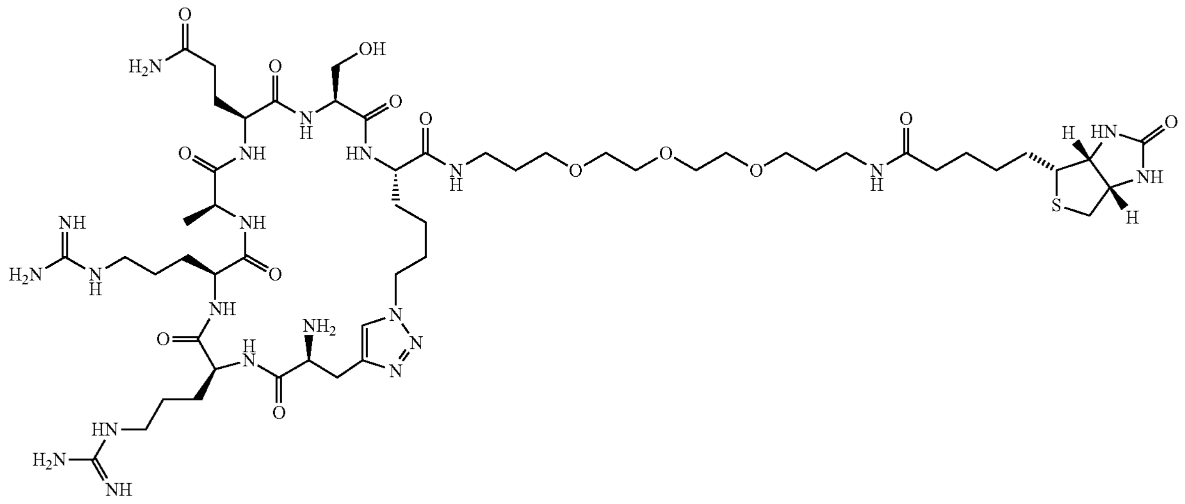

Example 3. In Vitro Assays with IL-17F Epitope1 Targeted Ligands

Sandwich ELISA.

A black 96-well NeutrAvidin Coated High Binding Capacity plate (15510, Pierce) was coated with 2 μM macrocyclic peptide ligand in TBS (25 mM Tris-HCl, 150 mM NaCl, pH 7.6) for 2 h at room temperature. Biotinylated monoclonal anti-IL17F (TA319597, Origene) was coated at 4 μg/mL in TBS as a control. The plate was aspirated and then washed with TBS (5×) and Wash Buffer (0.05% (v/v) Tween-20 in PBS, 1×). Full-length His-tagged IL-17F protein (ab167911, Abcam) was serially diluted in Wash Buffer (from 800 to 0 nM) and incubated in the designated microwells for 90 min at room temperature. Microwells were aspirated and subsequently washed with Wash Buffer (10×). To detect the bound IL-17F protein, Alkaline Phosphatase (AP)-conjugated Anti-6× His Tag® antibody [HIS-1] (ab49746, Abcam) was prepared at 1:10,000 dilution and added to the microwells for 1 h at room temperature. The plate was aspirated and washed with Wash Buffer (5×). AttoPhos® AP Fluorescent Substrate System (S1000, Promega) was employed to develop the microwells. Using an excitation wavelength of 430 nm, fluorescent emission at 535 nm was recorded by Beckman Coulter DTX880 photometer. Titration curves were fit using a four-parameter regression curve fitting program (Origin 8.5) to determine $EC_{50}$ values.

Figure 2A:
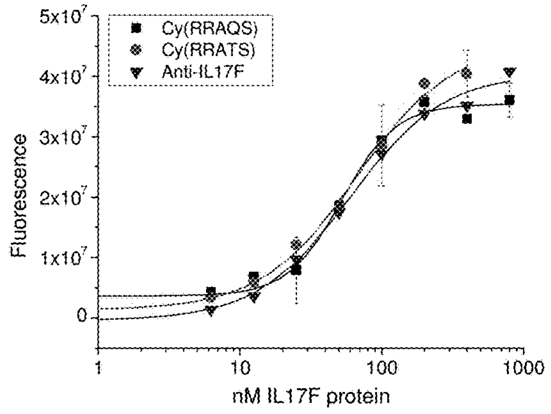
FIGS. 2A-2D: In vitro characterization of macrocycles developed against IL-17F Epitope1.

Results are shown in FIG. 2A. The binding affinity of $PEG_3$-biotin-modified Cy(RRATS) (SEQ ID NO:9) and Cy(RRAQS) (SEQ ID NO:10) was tested in an ELISA format. For these assays, a dilution series of full-length His-tagged IL-17F protein was captured using the macrocyclic peptide ligands immobilized on a NeutrAvidin-coated plate. Cy (RRATS) (SEQ ID NO:9) and Cy(RRAQS) (SEQ ID NO:10) exhibited $EC_{50}$ values of 66±9 nM and 52±5 nM, respectively, for human IL-17F protein. A similarly assayed biotinylated monoclonal anti-IL17F shows similar binding affinity.

Point ELISA (IL-17F Vs. IL-17A Selectivity Assay).

A black 96-well NeutrAvidin Coated High Binding Capacity plate (15510, Pierce) was coated with 2 μM macrocyclic peptide ligand in TBS (pH 7.6) for 2 h at room temperature. The plate was aspirated and then washed with TBS (5×) and Wash Buffer (0.05% (v/v) Tween-20 in PBS, 1×). Full-length His-tagged IL-17F (ab167911, Abcam) and IL-17A (ab166882, Abcam) proteins were prepared at 200 and 50 nM in Wash Buffer and incubated in the designated microwells for 90 min at room temperature. Microwells were aspirated and subsequently washed with Wash Buffer (10×). To detect the bound IL-17F and IL-17A proteins, Alkaline Phosphatase (AP)-conjugated Anti-6× His Tag® antibody [HIS-1] (ab49746, Abcam) was prepared at 1:10, 000 dilution and added to the microwells for 1 h at room temperature. The plate was aspirated and washed with Wash Buffer (5×). AttoPhos® AP Fluorescent Substrate System (S1000, Promega) was employed to develop the microwells. Using an excitation wavelength of 430 nm, fluorescent emission at 535 nm was recorded by Beckman Coulter DTX880 photometer.

Figure 2B:
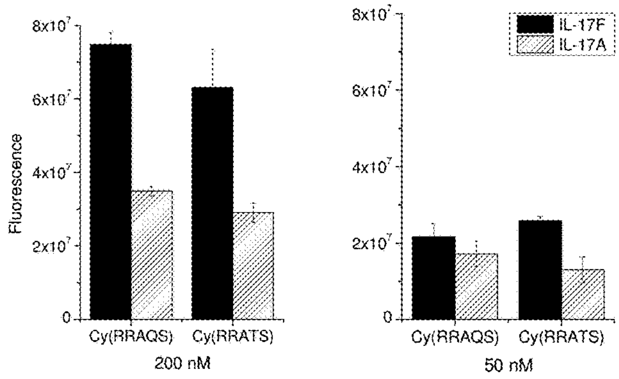
Figure 2C:
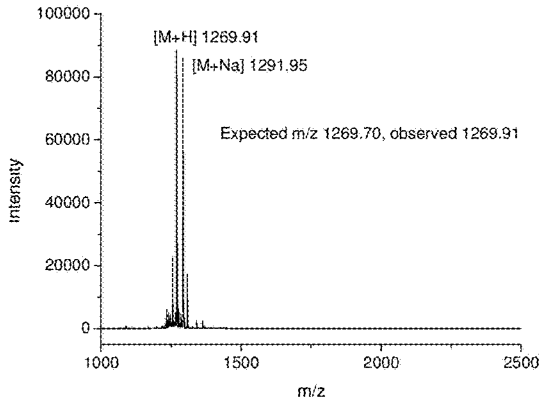
Figure 2D:
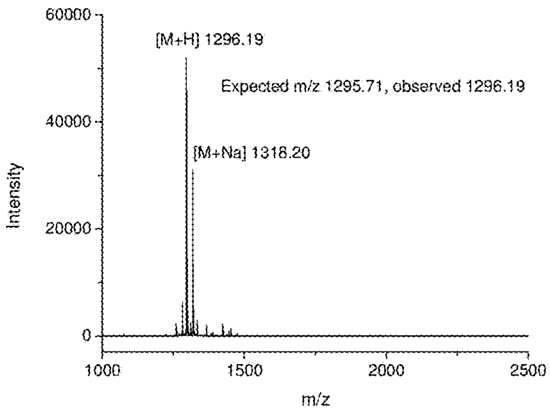

Results are shown in FIG. 2B. The selectivity of PEG3-biotin-modified Cy(RRATS) (SEQ ID NO:9) and Cy(R-RAQS) (SEQ ID NO:10) was tested in an ELISA format. For these assays, the full-length His-tagged IL-17F and IL-17A proteins were captured using the macrocyclic peptide ligands immobilized on a NeutrAvidin-coated plate. Both Cy(RRATS) (SEQ ID NO:9) and Cy(RRAQS) (SEQ ID NO:10) exhibited 2:1 selectivity for IL-17F over the 200-50 nM concentration range. These results confirm the selective nature of the epitope-targeting strategy.

Assay to Determine Orientation of Macrocycle Binding to IL-17F Epitope1.

A black 96-well NeutrAvidin Coated High Binding Capacity plate (15510, Pierce) was coated with 2 μM macrocyclic peptide ligand in TBS (pH 7.6) for 2 h at room temperature. Biotinylated monoclonal anti-IL17F (TA319597, Origene) was coated at 4 μg/mL in TBS as a control. The plate was aspirated and then washed with TBS (5×) and Wash Buffer (0.05% (v/v) Tween-20 in PBS, 1×). Chemically synthesized His-tagged IL-17F epitopes were prepared at 2 μM in Wash Buffer and incubated in the designated microwells for 90 min at room temperature. Wash Buffer without epitope was added as a control. Microwells were aspirated and subsequently washed with Wash Buffer (10×). To detect the bound IL-17F epitopes, Alkaline Phosphatase (AP)-conjugated Anti-6× His Tag® antibody [HIS-1] (ab49746, Abcam) was prepared at 1:10,000 dilution and added to the microwells for 1 h at room temperature. The plate was aspirated and washed with Wash Buffer (5×). AttoPhos® AP Fluorescent Substrate System (S1000, Promega) was employed to develop the microwells. Using an excitation wavelength of 430 nm, fluorescent emission at 535 nm was recorded by Beckman Coulter DTX880 photometer. Data are shown after subtraction of the no-epitope background.

Figures 3A, 3B:
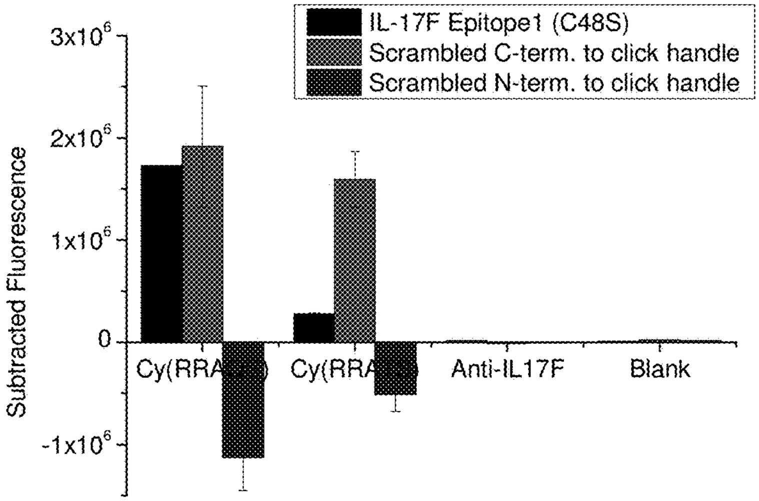
FIGS. 3A-3B: Orientation of macrocycle binding to IL-17F Epitope1.

Results are shown in FIG. 3. For this experiment, the IL-17F Epitope1 was re-synthesized with a $His_6$ assay handle and C48S substitution instead of a click handle. Two additional His-tagged IL-17F epitopes were synthesized to contain strategic scrambling of the sequences either N-terminal or C-terminal to C48S. Point ELISAs for the three His-tagged IL-17F epitopes were conducted against the immobilized macrocyclic peptide ligands. For $PEG_3$-biotin-modified Cy(RRATS) (SEQ ID NO:9) and Cy(RRAQS) (SEQ ID NO:10), positive ELISA signals were obtained for the His-tagged IL-17F Epitope1 (C48S) and the epitope scrambled C-terminal to click handle (black and red bars). Binding was destroyed when the epitope was scrambled N-terminal to the click handle (blue bars). Therefore, the macrocyclic peptide ligands show preferential binding to the sequence FFQKPES (SEQ ID NO:1) within IL-17F Epitope1 (C48S). On the other hand, biotinylated monoclonal anti-IL17F showed no appreciable binding to the His-tagged IL-17F epitopes as it was raised against a protein immunogen.

In summary, the results of FIGS. 2-3 confirm that the epitope-targeting strategy produced sub-100 nM affinity macrocyclic peptide ligands that selectively recognize IL-17F epitopes as well as the full-length protein.

Example 4. Screening for Macrocycle Anchor Against IL-17F Epitope2

Screens were similarly performed to target the IL-17F Epitope2 fragment (Biotin-$PEG_3$-GI[Az4]NENQRVS) (SEQ ID NO:33) using the triazole-cyclized OBOC library of the form H2N-Pra-Cy(XXXXX)-Met-TG (SEQ ID NO:34). Macrocycles were identified against the IL-17F Epitope2 fragment using the aforementioned four-step screening process: 1) a pre-clear to eliminate non-specific binders, 2) a product screen to identify hits resulting from epitope-templated in situ click chemistry, 3) a target screen against His-tagged IL-17F protein, and 4) additional target screens against His-tagged IL-17F protein in 1% to 5% (v/v) human serum to identify peptides whose binding to IL-17F is unperturbed by serum proteins.

Product Screen with IL-17F Epitope2.

The product screen was conducted with 3 mL of 100 μM IL-17F Epitope2 fragment (Biotin-$PEG_3$-GI[Az4]NENQRVS) (SEQ ID NO:33) in TBS for 1.5 h at room temperature to allow for an in situ click reaction to occur. The beads were washed with TBS ten times and then incubated with 7.5 M guanidine hydrochloride pH 2.0 for 1 h to remove all IL-17F epitope not attached covalently to the beads. These beads were washed with TBS ten times and re-blocked with Blocking Buffer for 2 h. A 1:10,000 dilution of Streptavidin-Alkaline Phosphatase in 5 mL Blocking Buffer was added for 1 h to detect the presence of IL-17F epitope clicked to beads. The beads were subsequently washed with 3×3 mL TBS (1 min ea), 3×3 mL 0.1 M glycine pH 2.8 wash buffer, 3×3 mL TBS, then 3×3 mL Alkaline Phosphatase (pH 9) buffer (5 min ea). After this, the beads were developed with BCIP/NBT for 25 min as outlined in the pre-clear. Purple epitope-conjugated hit beads were selected by pipet and saved. These hits (98 total: 50 dark purple, 48 medium to light purple) were treated with 7.5 M guanidine hydrochloride pH 2.0 for 30 min to remove attached streptavidin, washed ten times with water, and incubated in NMP overnight to decolorize.

Target Screen with His-Tagged IL-17F Protein.

Product hits were washed with water ten times and stored in TBS at 4° C. These 98 beads were transferred to a Corning® 8162 Costar® Spin-X® centrifuge tube filter (cellulose acetate membrane) and incubated with Blocking Buffer for 3 h at room temperature. The beads were rinsed three times with Blocking Buffer and then incubated with 150 nM of full-length His-tagged IL-17F protein (ab167911, Abcam) in Blocking Buffer (preparation: 0.5 μL His-tagged IL-17F protein in 200 μL Blocking Buffer) for 1 h at room temperature. The beads were washed three times with Blocking Buffer and then incubated with 500 μL of 1:10,000 Anti-6× His Tag® antibody [HIS-1] (Alkaline Phosphatase-conjugated) (ab49746, Abcam) in Blocking Buffer for 1 h at room temperature. The beads were subsequently washed with 3×500 μL Blocking Buffer, 3×500 μL TBS, then 3×500 μL Alkaline Phosphatase (pH 9) buffer (centrifuging at 7000 rpm for 30 sec after each wash). After this, the beads were developed with BOP/NBT for 10 min. Purple hit beads bound to IL-17F protein were selected by pipet and saved. 53 beads were purple indicating binding to both the IL-17 epitope and protein, while 40 were clear indicating no binding to IL-17F protein. The 53 target hits were treated with 7.5 M guanidine hydrochloride pH 2.0 for 30 min to remove bound proteins, washed ten times with water, and incubated in NMP overnight to decolorize.

Target Screen with His-Tagged IL-17F Protein in 1% (v/v) Human Serum.

Target hits were washed with water ten times. These 53 beads were incubated with Blocking Buffer for 7 h in a Corning® 8162 Costar® Spin-X® centrifuge tube filter (cellulose acetate membrane). The beads were rinsed three times with Blocking Buffer and then incubated with 150 nM of full-length His-tagged IL-17F protein (ab167911, Abcam) in Blocking Buffer containing 1% (v/v) human serum (HS-30, Omega Scientific) for 1 h at room temperature (preparation: 1.25 μL, His-tagged IL-17F protein+5 μL filtered serum+495 μL Blocking Buffer). Note: Before the screen, particulate matter was removed from serum by centrifugation (7000 rpm, 30 sec) using a Corning® 8162 Costar® Spin-X® tube filter. The beads were washed three times with Blocking Buffer and then incubated with 500 μL of 1:10,000 Anti-6× His Tag® antibody [HIS-1] (Alkaline Phosphatase-conjugated) (ab49746, Abcam) in Blocking Buffer for 1 h at room temperature. The beads were subsequently washed with 3×500 μL Blocking Buffer, 3×500 μL TBS, then 3×500 μL Alkaline Phosphatase (pH 9) buffer (centrifuging at 7000 rpm for 30 sec after each wash). After this, the beads were developed with BCIP/NBT for 10 min. Purple hit beads were selected by pipet and saved. The 23 hits whose binding to IL-17F protein was unperturbed by serum proteins were treated with 7.5 M guanidine hydrochloride pH 2.0 for 30 min to remove bound proteins, washed ten times with water, and incubated in NMP overnight to decolorize.

Target Screen with His-Tagged IL-17F Protein in 5% (v/v) Human Serum to Refine the Number of Hits.

The 23 beads were washed with water ten times and then incubated with Blocking Buffer for 7 h in a Corning® 8162 Costar® Spin-X® centrifuge tube filter (cellulose acetate membrane). The beads were rinsed three times with Blocking Buffer and then incubated with 150 nM of full-length His-tagged IL-17F protein (ab167911, Abcam) in Blocking Buffer containing 5% (v/v) human serum (HS-30, Omega Scientific) for 1 h at room temperature (preparation: 1.25 μL His-tagged IL-17F protein+25 μL filtered serum+475 μL Blocking Buffer). Note: Before the screen, particulate matter was removed from serum by centrifugation (7000 rpm, 30 sec) using a Corning® 8162 Costar® Spin-X® tube filter. The beads were washed three times with Blocking Buffer and then incubated with 500 μL of 1:10,000 Anti-6× His Tag® antibody [HIS-1] (Alkaline Phosphatase-conjugated) (ab49746, Abcam) in Blocking Buffer for 1 h at room temperature. The beads were subsequently washed with 3×500 μL, Blocking Buffer, 3×500 μL TBS, then 3×500 μL Alkaline Phosphatase (pH 9) buffer (centrifuging at 7000 rpm for 30 sec after each wash). After this, the beads were developed with BCIP/NBT for 10 min. Purple hit beads were selected by pipet and saved. The 6 hits whose binding to IL-17F protein was unperturbed by the increased background of serum proteins were treated with 7.5 M guanidine hydrochloride pH 2.0 for 30 min to remove bound proteins, washed ten times with water, and incubated in NMP overnight to decolorize. The 6 hits were finally washed with water ten times to prepare for sequencing analysis.

Sequencing was performed via Edman degradation. The Edman sequencer was unable to distinguish between 1) residues K (lysine) and L (leucine), and 2) residues Q (glutamine) and T (threonine). Sequencing results are shown in Table 2 including the K/L and Q/T variants.

TABLE 2

Sequences of macrocyclic peptide hits identified against IL-17F Epitope2

| | x2 | x3 | x4 | x5 | x6 |
|---|---|---|---|---|---|
| hit1 | K | Y | G | E | V |
| | L | Y | G | E | V |
| hit2 | V | H | K | S | G |
| | V | H | L | S | G |
| hit3 | Q | K | H | G | P |
| | T | K | H | G | P |
| | Q | L | H | G | P |
| | T | L | H | G | P |
| hit4 | Y | D | L | Q | R |
| | Y | D | L | T | R |
| | Y | D | K | Q | R |
| | Y | D | K | T | R |
| hit5 | K | K | G | W | P |
| | K | L | G | W | P |
| | L | K | G | W | P |
| | L | L | G | W | P |
| hit6 | R | S | Y | N | L |
| | R | S | Y | N | K |

These candidate peptides were re-synthesized on a cleavable resin, purified by reversed phase HPLC using a $C_{18}$ column, and tested against the IL-17F protein by ELISA.

Synthesis Data for IL-17F Epitope2 Hits

Cy(KYGEV) (SEQ ID NO:11)-PEG$_3$-biotin. MALDI-MS (m/z): calcd. for $C_{58}H_{93}N_{15}O_{15}S$ (M+H) 1272.67; found 1274.02.

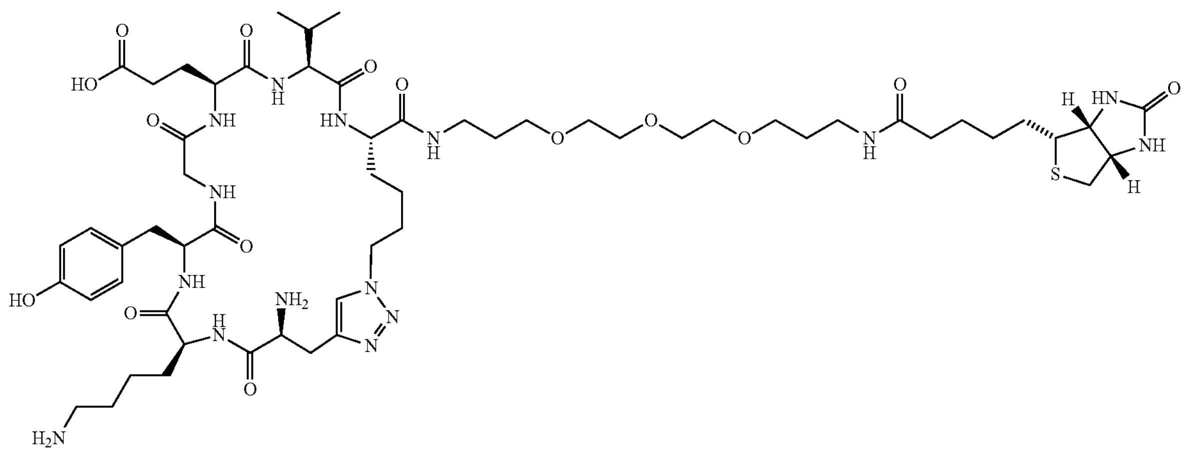

Cy(LYGEV) (SEQ ID NO:12)-PEG$_3$-biotin. MALDI-MS (m/z): calcd. for $C_{58}H_{92}N_{14}O_{15}S$ (M+H) 1257.66; found 1259.13.
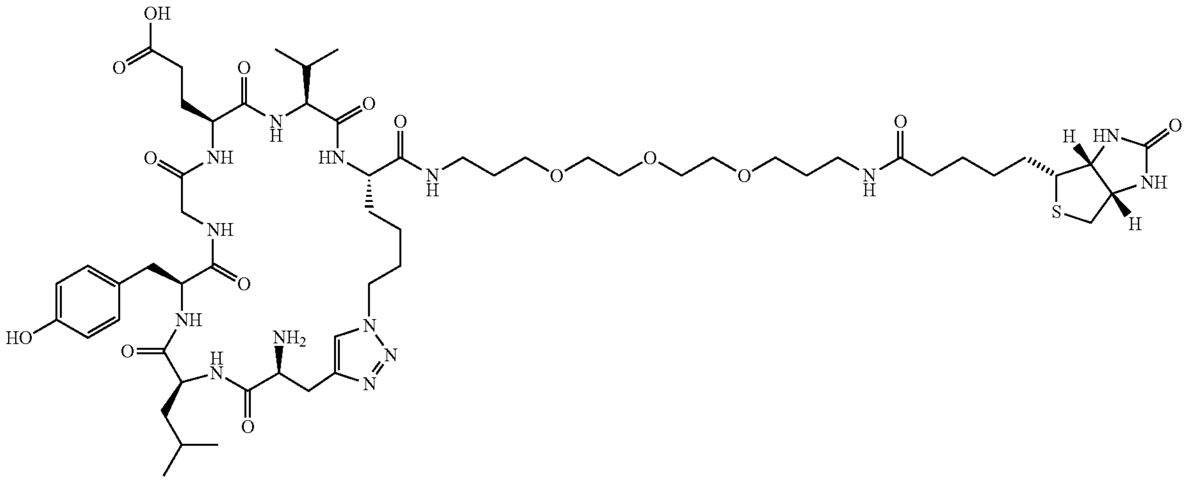
Cy(VHKSG) (SEQ ID NO:13)-PEG$_3$-biotin. MALDI-MS (m/z): calcd. for $C_{53}11_{89}N_{17}O_{13}S$ (M+H) 1204.65; found 1206.20.
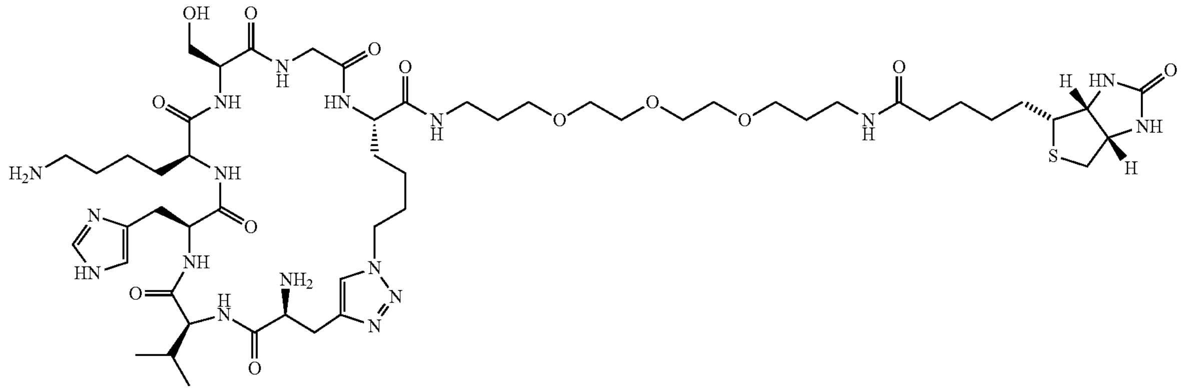
Cy(VHLSG) (SEQ ID NO:14)-PEG$_3$-biotin. MALDI-MS (m/z): calcd. for $C_{53}H_{88}N_{16}O_{13}S$ (M+H) 1189.64; found 1191.11.
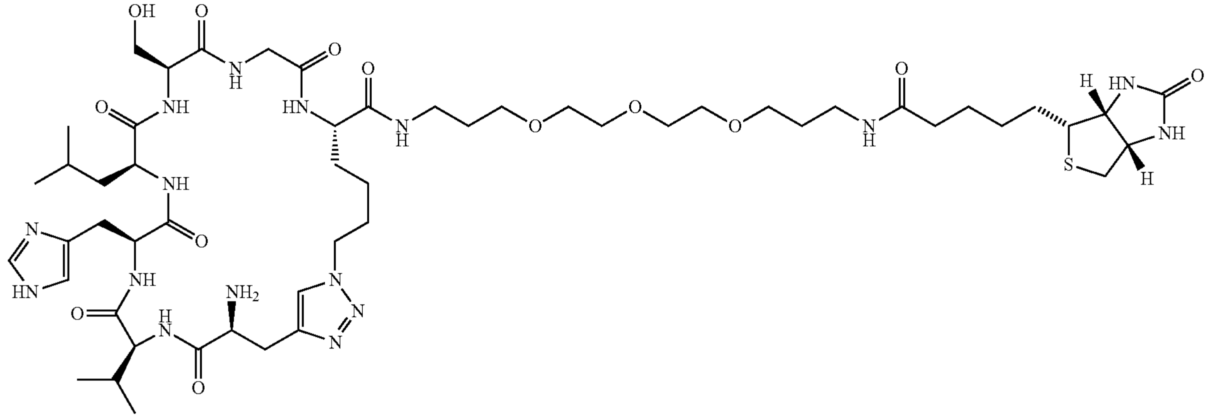

Cy(QKHGP) (SEQ ID NO:15)-PEG$_3$-biotin. MALDI-MS (m/z): calcd. for $C_{55}H_{90}N_{18}O_{13}S$ (M+H) 1243.67; found 1245.18.
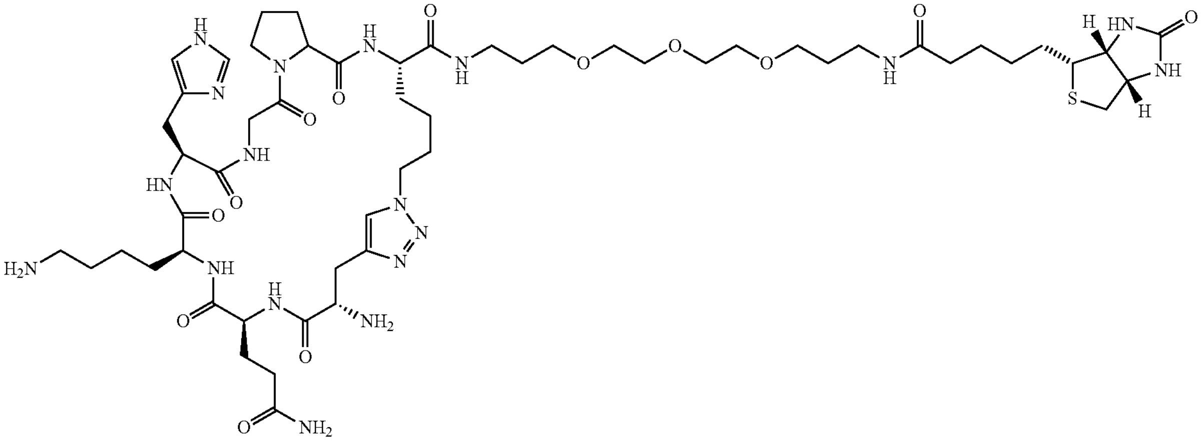
Cy(TKHGP) (SEQ ID NO:16)-PEG$_3$-biotin. MALDI-MS (m/z): calcd. for $C_{54}H_{89}N_{17}O_{13}S$ (M+H) 1216.65; found 1218.25.
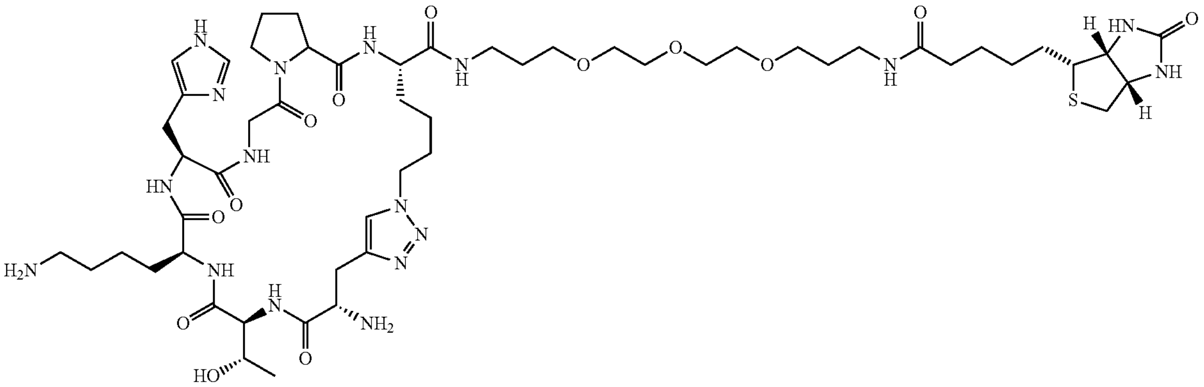
Cy(QLHGP) (SEQ ID NO:17)-PEG$_3$-biotin. MALDI-MS (m/z): calcd. for $C_{55}H_{89}N_{17}O_{13}S$ (M+H) 1228.65; found 1228.84.
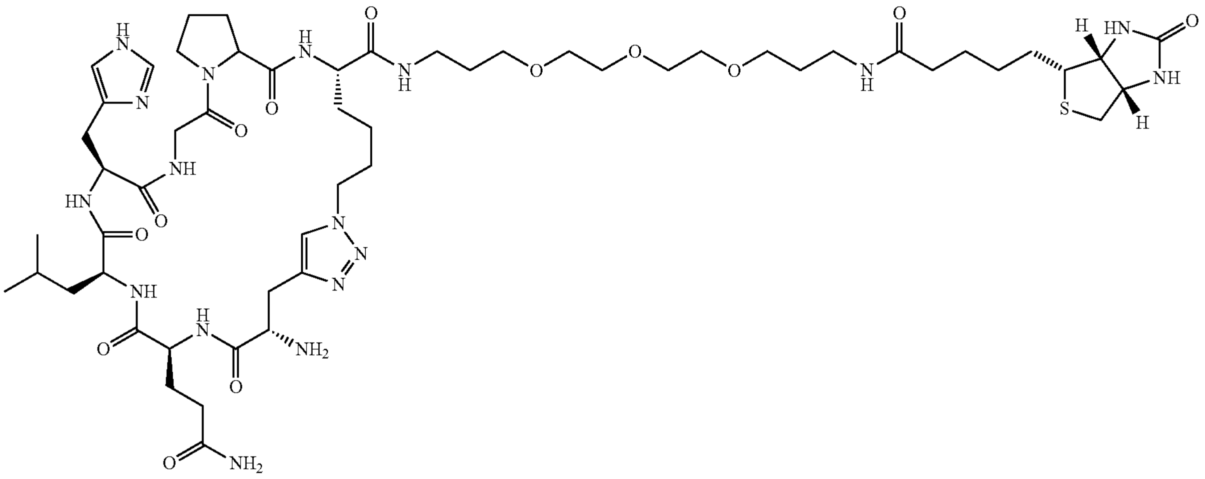

Cy(TLHGP) (SEQ ID NO:18)-PEG$_3$-biotin. MALDI-MS (m/z): calcd. for $C_{54}H_{88}N_{16}O_{13}S$ (M+H) 1201.64; found 1201.73.
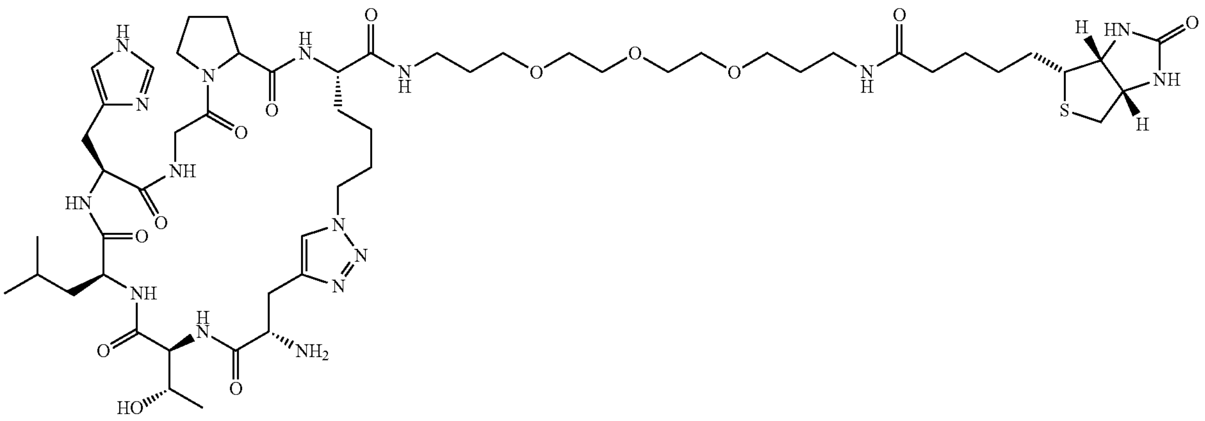
Cy(YDLQR) (SEQ ID NO:19)-PEG$_3$-biotin. MALDI-MS (m/z): calcd. for $C_{61}H_{98}N_{18}O_{16}S$ (M+H) 1371.71; found 1372.16.
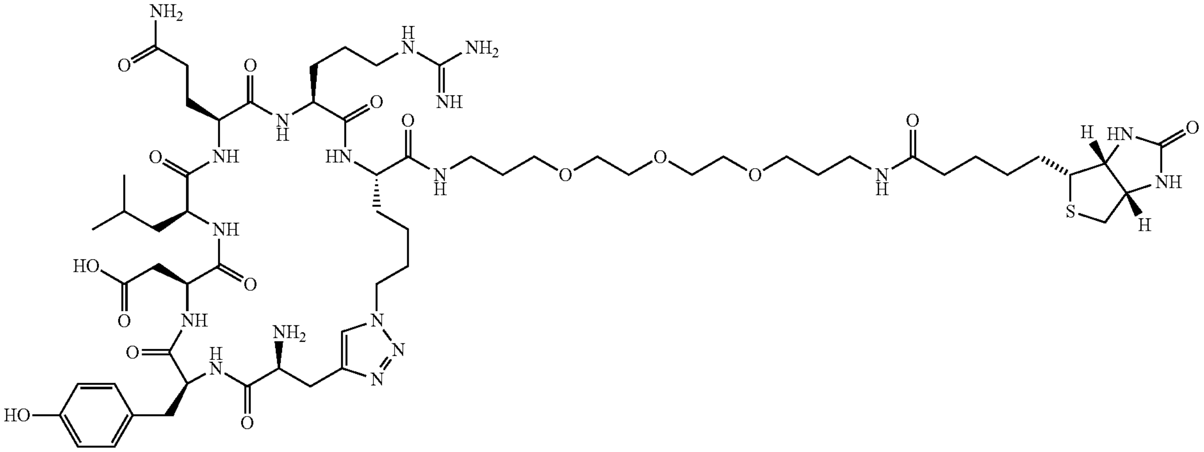
Cy(YDLTR) (SEQ ID NO:20)-PEG$_3$-biotin. MALDI-MS (m/z): calcd. for $C_{60}H_{97}N_{17}O_{16}S$ (M+H) 1344.70; found 1345.13.
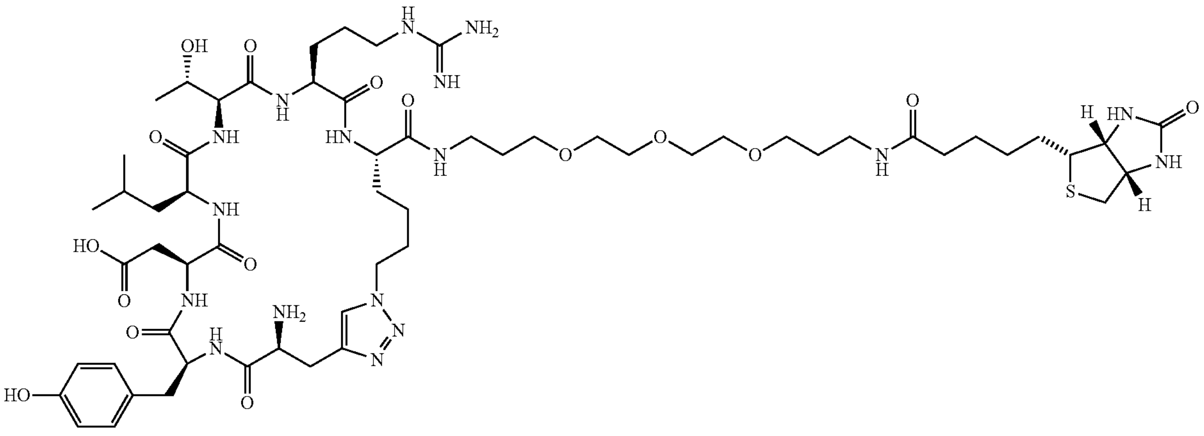

Cy(YDKQR) (SEQ ID NO:21)-PEG$_3$-biotin. MALDI-MS (m/z): calcd. for C61H99N19O16S (M+H) 1386.72; found 1387.00.
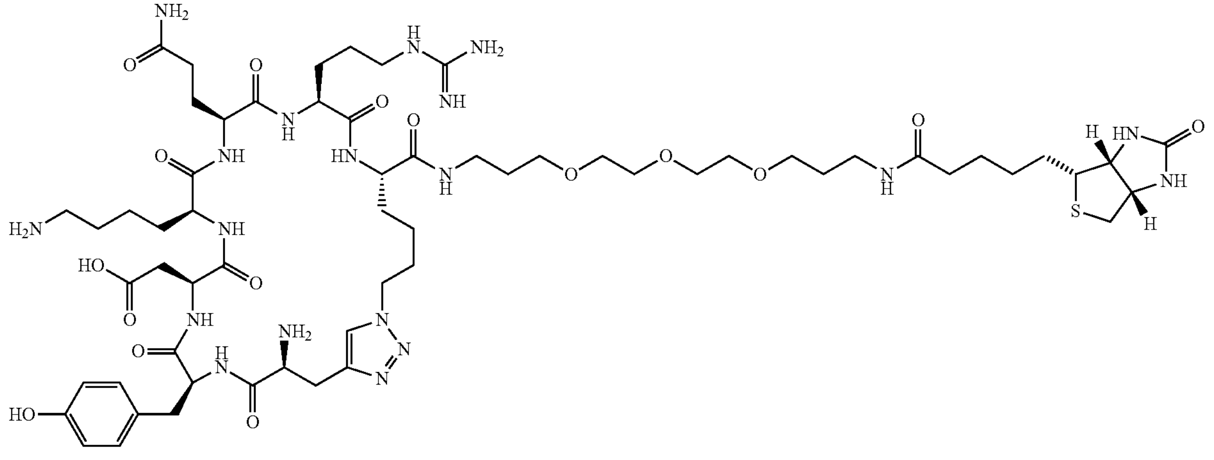
Cy(YDKTR) (SEQ ID NO:22)-PEG$_3$-biotin. MALDI-MS (m/z): calcd. for $C_{60}H_{98}N_{18}O_{16}S$ (M+H) 1359.71; found 1359.94.
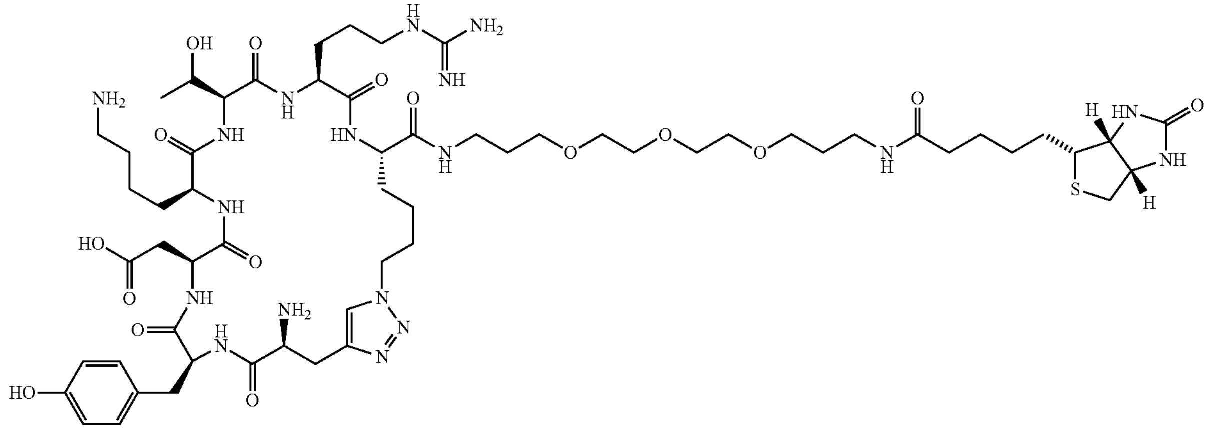
Biotin-PEG$_3$-Cy(KKGWP) (SEQ ID NO:23). MALDI-MS (m/z): calcd. for $C_{59}H_{91}N_{17}O_{13}S$ (M+H) 1278.67; found 1278.83.
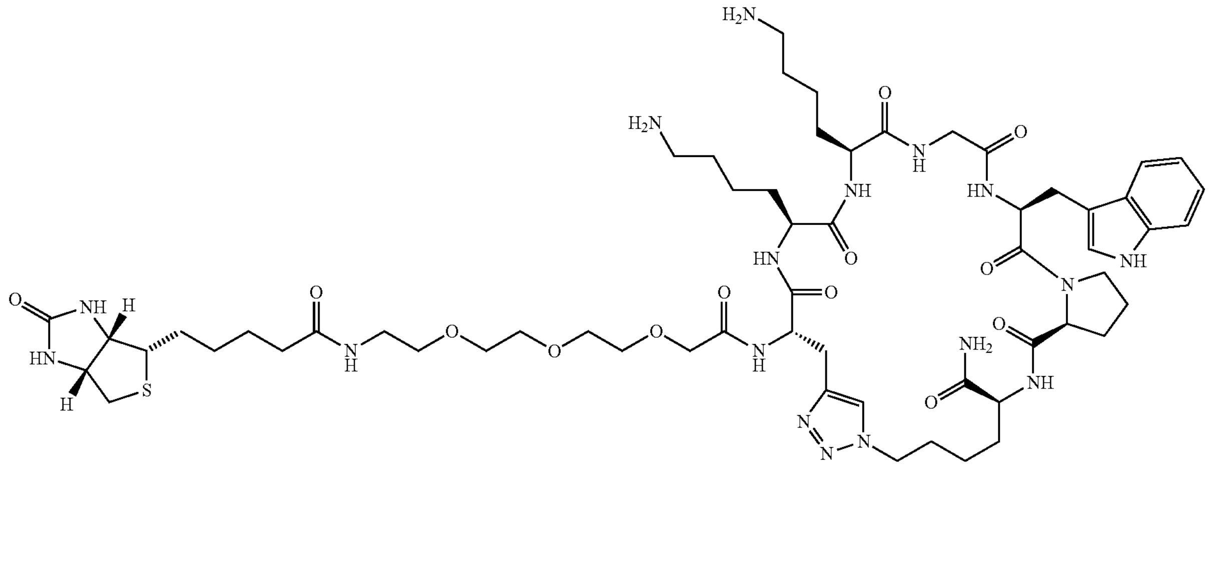 [SMILES: NCCCC[C@@H]1NC(=O)[C@H](CCCCN)NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC(=O)[C@@H]2CCCN2C(=O)[C@H](Cc2c[nH]c3ccccc23)NC(=O)CNC1=O]

Biotin-PEG$_3$-Cy(KLGWP) (SEQ ID NO:24). MALDI-MS (m/z): calcd. for $C_{59}H_{90}N_{16}O_{13}S$ (M+H) 1263.66; found 1263.92.
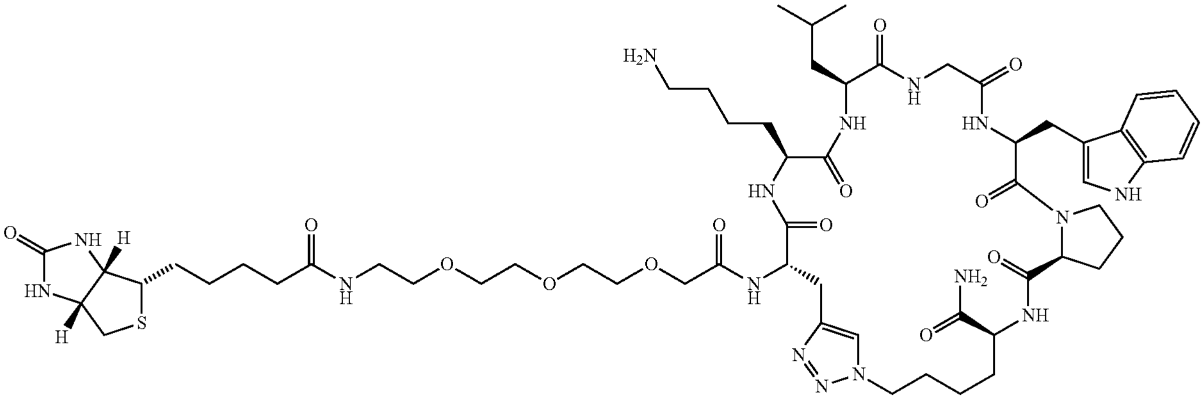 [SMILES: CC(C)C[C@@H]1NC(=O)[C@H](CCCCN)NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC(=O)[C@@H]2CCCN2C(=O)[C@H](Cc2c[nH]c3ccccc23)NC(=O)CNC1=O]
Biotin-PEG$_3$-Cy(LKGWP) (SEQ ID NO:25). MALDI-MS (m/z): calcd. for $C_{59}H_{90}N_{16}O_{13}S$ (M+H) 1263.66; found 1263.86.
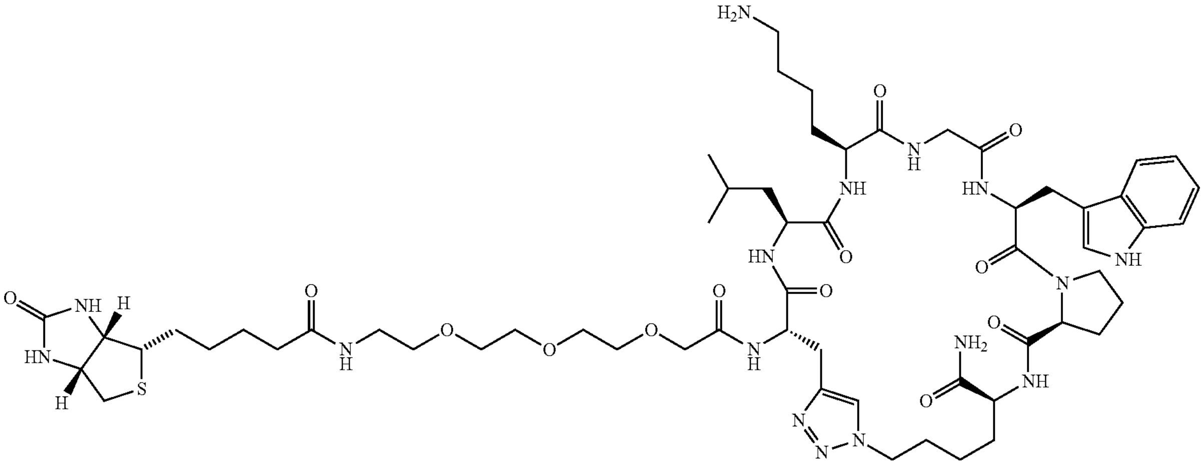 [SMILES: CC(C)C[C@@H]1NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC(=O)[C@@H]2CCCN2C(=O)[C@H](Cc2c[nH]c3ccccc23)NC(=O)CNC(=O)[C@H](CCCCN)NC1=O]
Biotin-PEG$_3$-Cy(LLGWP) (SEQ ID NO:26). MALDI-MS (m/z): calcd. for $C_{59}H_{89}N_{15}O_{13}S$ (M+H) 1248.65; found 1248.89.
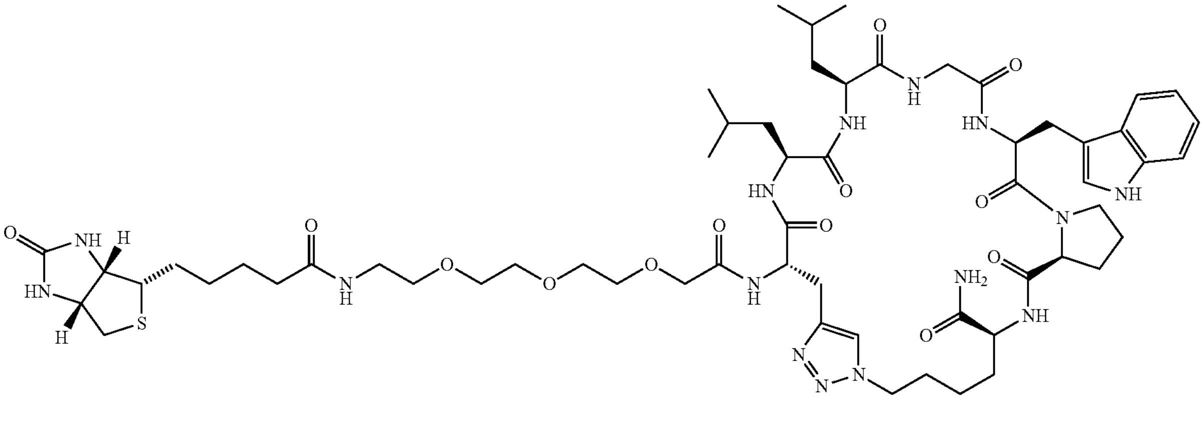 [SMILES: CC(C)C[C@@H]1NC(=O)[C@H](CC(C)C)NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC(=O)[C@@H]2CCCN2C(=O)[C@H](Cc2c[nH]c3ccccc23)NC(=O)CNC1=O]

Biotin-PEG$_3$-Cy(RSYNL) (SEQ ID NO:27). MALDI-MS (m/z): calcd. for $C_{57}H_{90}N_{18}O_{16}S$ (M+H) 1315.65; found 1315.95.

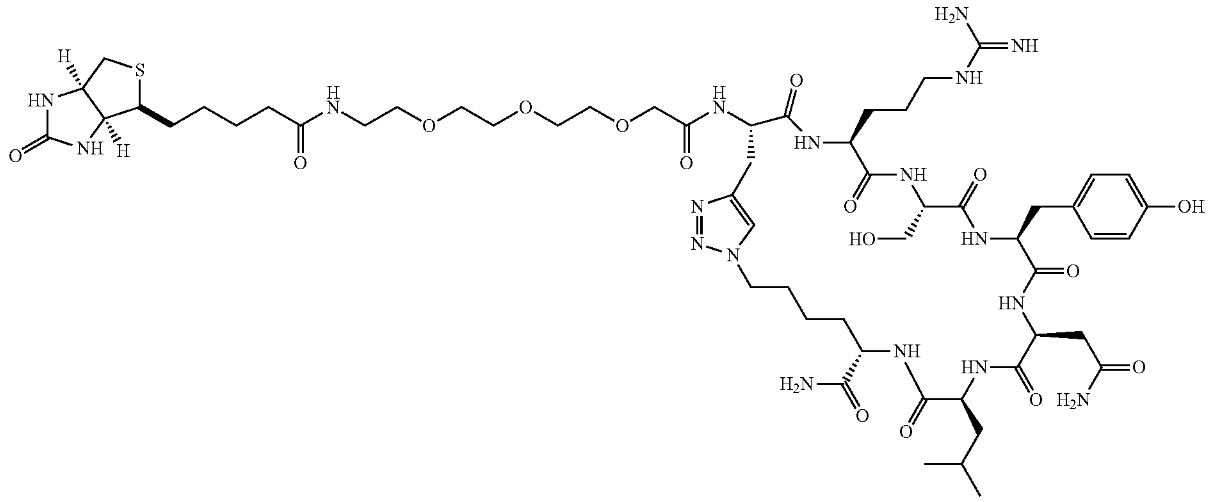 [SMILES: CC(C)C[C@@H]1NC(=O)[C@H](CC(N)=O)NC(=O)[C@H](Cc2ccc(O)cc2)NC(=O)[C@H](CO)NC(=O)[C@H](CCCNC(=N)N)NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC1=O]

Biotin-PEG$_3$-Cy(RSYNK) (SEQ ID NO:28). MALDI-MS (m/z): calcd. for $C_{57}H_{91}N_{19}O_{16}S$ (M+H) 1330.66; found 1331.06.

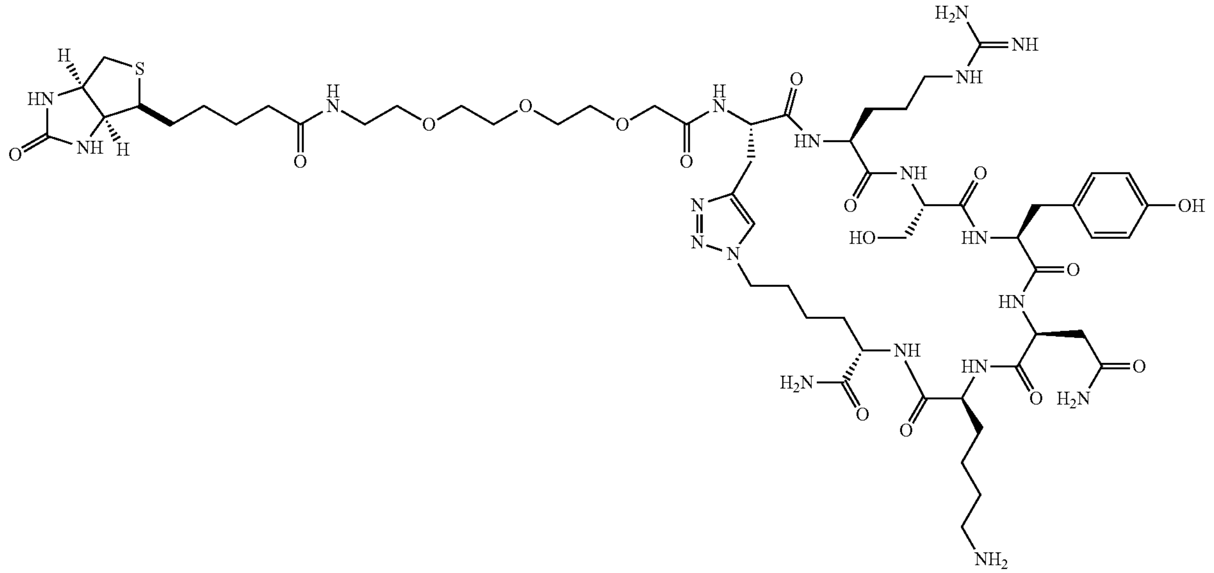 [SMILES: N=C(N)NCCC[C@@H]1NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC(=O)[C@H](CCCCN)NC(=O)[C@H](CC(N)=O)NC(=O)[C@H](Cc2ccc(O)cc2)NC(=O)[C@H](CO)NC1=O]

Example 5. In Vitro Assays with IL-17F Epitope2 Targeted Ligands

Sandwich ELISA.

These assays were performed using the same protocol that was used to evaluate the IL-17F Epitope1 targeted ligands.

Figure 4A:
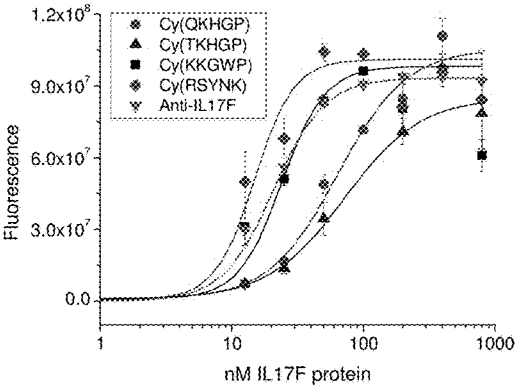
FIGS. 4A-4C: In vitro characterization of macrocycles developed against IL-17F Epitope2.

Results are shown in FIG. 4A. The binding affinity of PEG$_3$-biotin-modified Cy(QKHGP) (SEQ ID NO:15), Cy(TKHGP) (SEQ ID NO:16), Cy(KKGWP) (SEQ ID NO:23), and Cy(RSYNK) (SEQ ID NO:28) was tested in an ELISA format. For these assays, a dilution series of full-length His-tagged IL-17F protein was captured using the macrocyclic peptide ligands immobilized on a NeutrAvidin-coated plate. Cy(QKHGP) (SEQ ID NO:15) and Cy(T-KHGP) (SEQ ID NO:16) exhibited $EC_{50}$ values of 64±10 nM and 72±16 nM, respectively, for human IL-17F protein. Cy(KKGWP) (SEQ ID NO:23) and Cy(RSYNK) (SEQ ID NO:28) exhibited $EC_{50}$ values of 24±3 nM and 15±5 nM, respectively, for human IL-17F protein. Interestingly, Cy(RSYNK) (SEQ ID NO:28) exceeds the binding affinity of the similarly assayed biotinylated monoclonal anti-IL17F.

Point ELISA (IL-17F Vs. IL-17A Selectivity Assay).

A black 96-well NeutrAvidin Coated High Binding Capacity plate (15510, Pierce) was coated with 2 μM macrocyclic peptide ligand in TBS (pH 7.6) for 2 h at room temperature. Biotinylated monoclonal anti-IL17F (TA319597, Origene) was coated at 4 μg/mL in TBS as a control. The plate was aspirated and then washed with TBS (5×) and Wash Buffer (0.05% (v/v) Tween-20 in PBS, 1×). Full-length His-tagged IL-17F (ab167911, Abcam) and IL-17A (ab166882, Abcam) proteins were prepared at 100 nM in Wash Buffer and incubated in the designated microwells for 90 min at room temperature. Microwells were aspirated and subsequently washed with Wash Buffer (10×). To detect the bound IL-17F and IL-17A proteins, Alkaline Phosphatase (AP)-conjugated Anti-6× His Tag® antibody [HIS-1] (ab49746, Abcam) was prepared at 1:10,000 dilution and added to the microwells for 1 h at room temperature. The plate was aspirated and washed with Wash Buffer (5×). AttoPhos® AP Fluorescent Substrate System (S1000, Promega) was employed to develop the microwells. Using an excitation wavelength of 430 nm, fluorescent emission at 535 nm was recorded by Beckman Coulter DTX880 photometer.

Figure 4B:
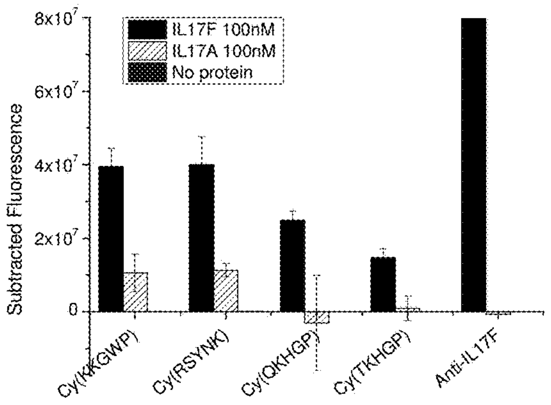
Figure 4C:
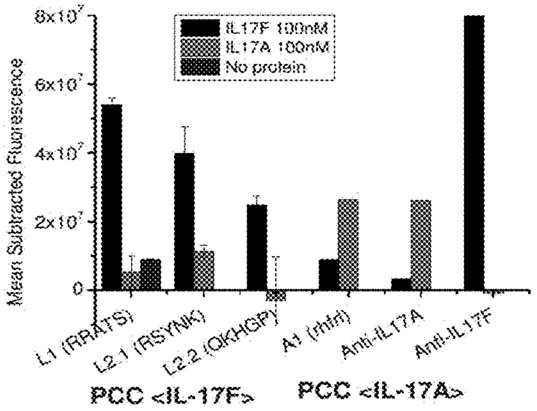

Results are shown in FIG. 4B. The selectivity of $PEG_3$-biotin-modified Cy(QKHGP) (SEQ ID NO:15), Cy(TKHGP) (SEQ ID NO:16), Cy(KKGWP) (SEQ ID NO:23), and Cy(RSYNK) (SEQ ID NO:28) was tested in an ELISA format. For these assays, the full-length His-tagged IL-17F and IL-17A proteins were captured using the macrocyclic peptide ligands immobilized on a NeutrAvidin-coated plate. Both Cy(KKGWP) (SEQ ID NO:23) and Cy(RSYNK) (SEQ ID NO:28) exhibited 4:1 selectivity for IL-17F at 100 nM. Other ligands, including Cy(QKHGP) (SEQ ID NO:15) and Cy(TKHGP) (SEQ ID NO:16), and biotinylated monoclonal anti-IL17F show even higher (almost absolute) selectivity for IL-17F. Again, these results confirm the selective nature of the epitope-targeting strategy.

Example 6. Designing a Linker to Covalently Join Two Macrocyclic Ligands

The tertiary structure of the IL-17F protein was subsequently exploited as a scaffold for developing a biligand PCC agent that exhibits true cooperative binding ($K_D$ range of <1 nM). Combinations of two macrocycles were covalently joined together to create a biligand PCC agent that displays high avidity for the two epitopes.

Figure 5A:
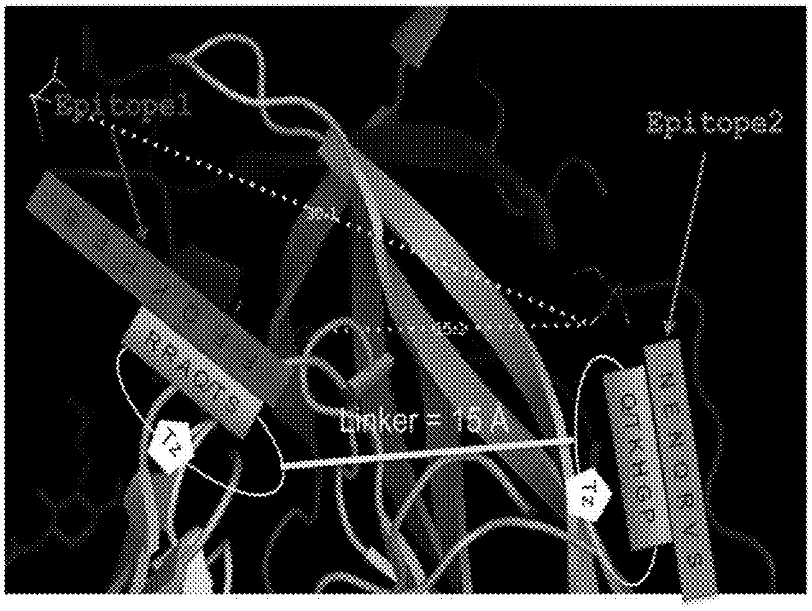
FIGS. 5A-5B: 3-D structural representations of the IL-17F homodimer. The sequences of IL-17F Epitopes1-2 and representative epitope-targeted macrocycles are overlaid (Tz=triazole). The distances (A) measured between the two epitopes are shown with dashed lines.
Figure 5B:
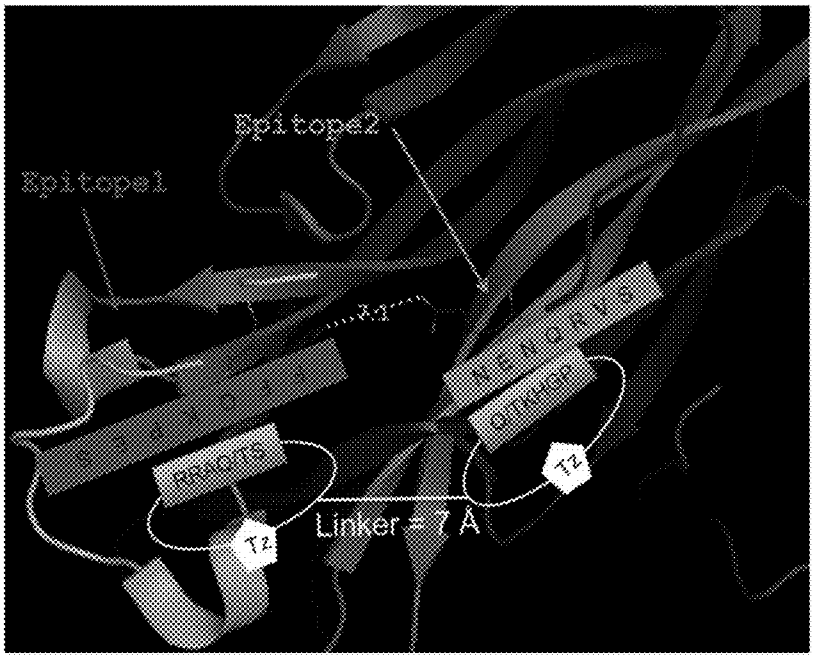
Figure 6A:
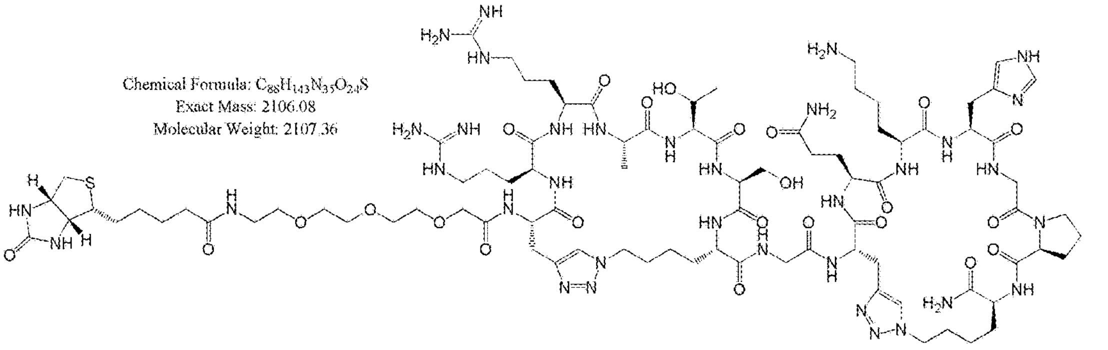
FIGS. 6A-6F: Structures of cooperative biligand candidates with linkers ranging from 4.4 to 26.4 Å to join the two macrocycles.
Figure 6B:
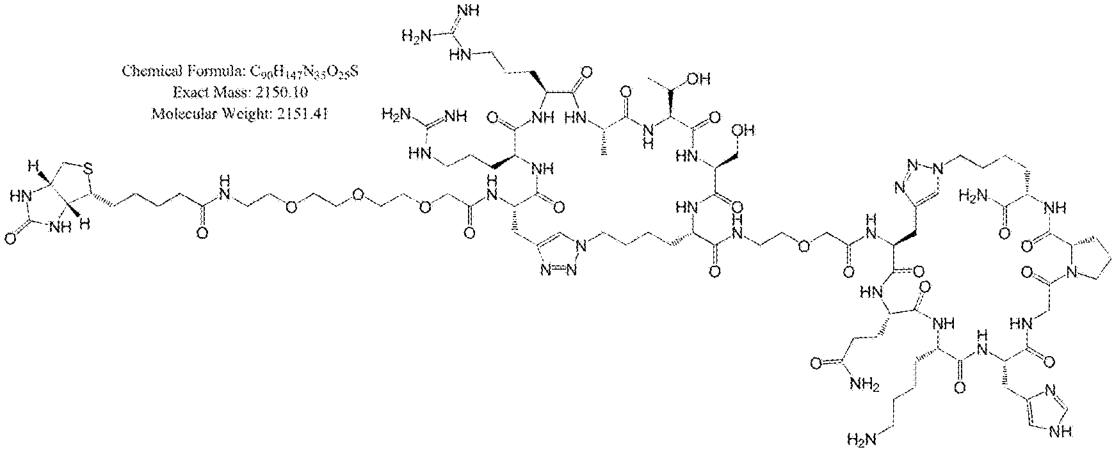
Figure 6C:
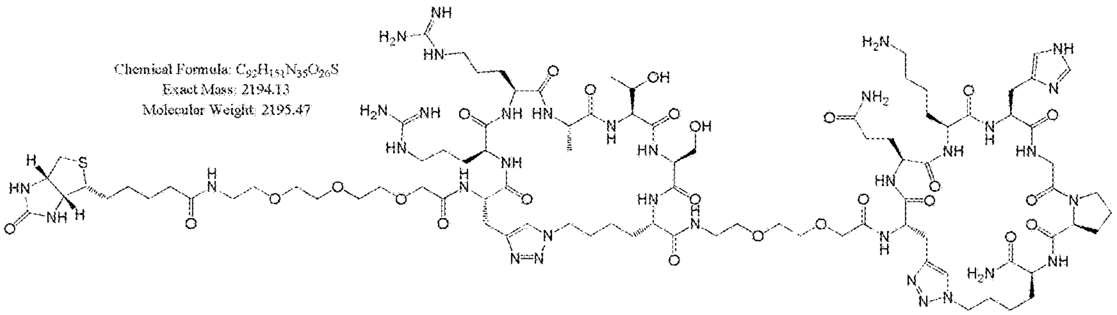
Figure 6D:
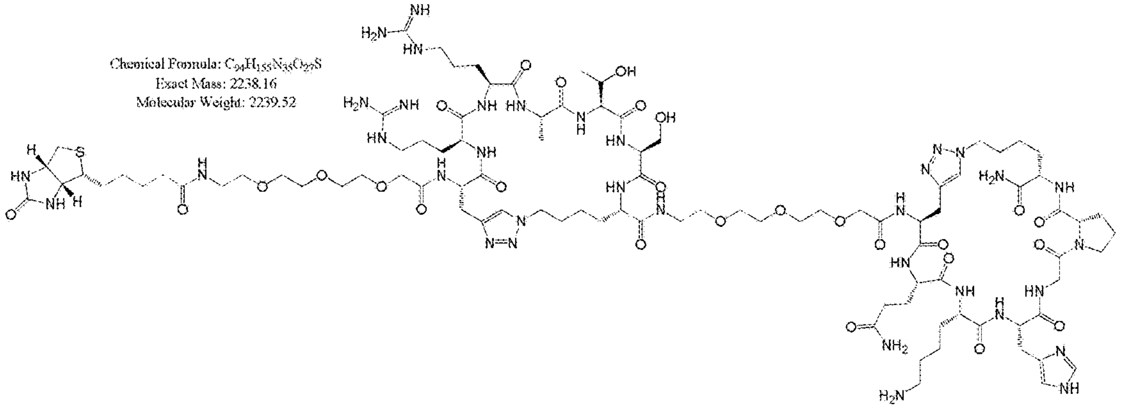
Figure 6E:
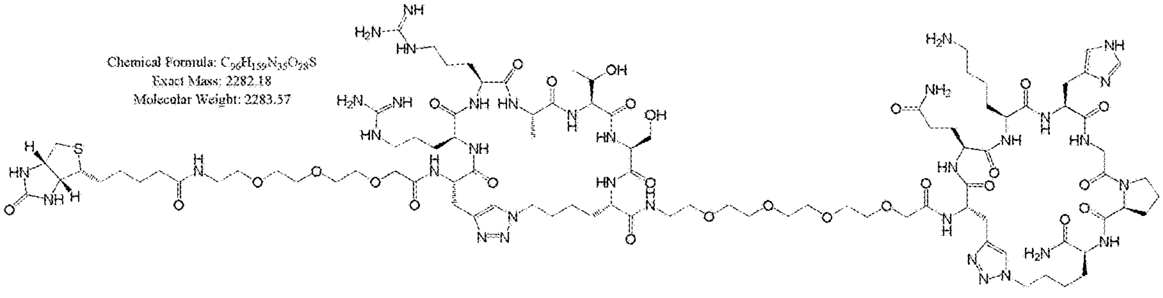
Figure 6F:
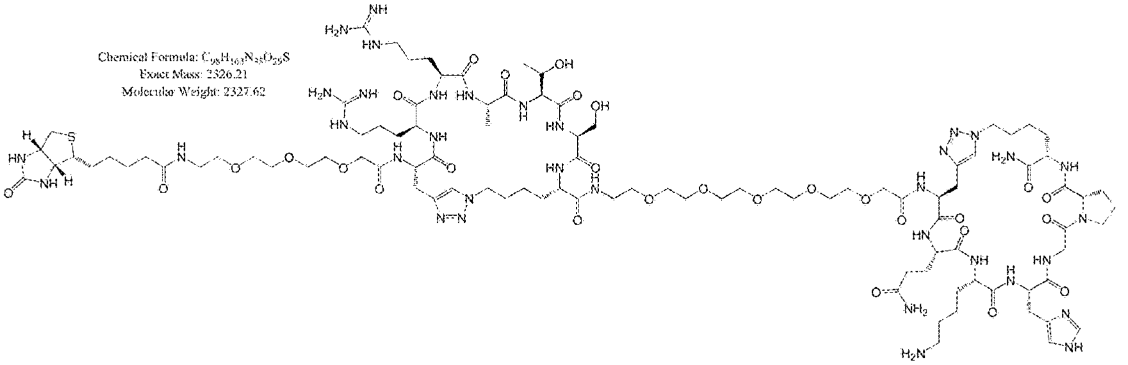

Important to this process is the design of suitable linker to bridge the distance between the two epitopes of the protein. The 3-D crystal structure of IL-17F (PDB ID: 1JPY) was analyzed in PyMOL (DeLano Scientific) to identify the distances between IL-17F Epitope1 and IL-17F Epitope2 (FIG. 5). In IL-17F Epitope1, focus was placed on the sequence FFQKPES (SEQ ID NO:1) because the macrocycles Cy(RRATS) (SEQ ID NO:9) and Cy(RRAQS) (SEQ ID NO:10) were determined to interact with this region preferentially (FIG. 3). The sequence NENQRVS (SEQ ID NO:3) within IL-17F Epitope2 was the assumed binding region for macrocycles Cy(QKHGP) (SEQ ID NO:15), Cy(TKHGP) (SEQ ID NO:16), Cy(KKGWP) (SEQ ID NO:23), and Cy(RSYNK) (SEQ ID NO:28) because of the N-terminal location of the click handle. Because IL-17F natively exists as a homodimer, distances were measured between the two epitopes within one and across both monomers. In the monomeric IL-17F protein, the sequence FFQKPES (SEQ ID NO:1) (in IL-17F Epitope1) and IL-17F Epitope2 are separated by ~15 Å. Thus, a chemical linker of ~15 Å would be useful for covalently joining one macrocycle targeted to IL-17F Epitope1 and one macrocycle targeted to IL-17F Epitope2. The resultant cooperative biligands would be useful for detection or treatment of IL-17F and the IL-17A/F heterodimer. In the homodimeric IL-17F protein, the sequence FFQKPES (SEQ ID NO:1) (in IL-17F Epitope1) from one monomer and IL-17F Epitope2 from the other monomer are separated by ~7 Å. Thus, a chemical linker of ~7 Å would be useful for covalently joining one macrocycle targeted to IL-17F Epitope1 and one macrocycle targeted to IL-17F Epitope2. The resultant cooperative biligands would be useful for detection or treatment of IL-17F.

Example 7. Synthesis of Cooperative Biligand Candidates

Cooperative biligand candidates were synthesized with a variable length linker covalently joining one macrocycle from IL-17F Epitope1 with one macrocycle from IL-17F Epitope2. The linker connecting the two macrocycles was a single PEGylated amino acid (Fmoc-NH-$PEG_x$-Propionic Acid; x=1 to 5) or glycine (Gly). A PEG linker was chosen because it is available in various lengths that would bridge the 7-15 Å distance between the two epitopes of the protein. PEG also is expected to display anti-biofouling properties.

Cooperative biligand candidates were first generated from Cy(RRATS) (SEQ ID NO:9) (targeted to IL-17F Epitope1) and Cy(QKHGP) (SEQ ID NO:15) (targeted to IL-17F Epitope2). Cy(QKHGP) (SEQ ID NO:15) was prioritized based on its high selectivity for IL-17F. Structures of the cooperative biligand candidates Biotin-$PEG_3$-Cy(RRATS) (SEQ ID NO:9)-$PEG_x$-Cy(QKHGP) (SEQ ID NO:15) are shown in FIG. 6. Cooperative biligand candidates were also generated from Cy(RRATS) (SEQ ID NO:9) (targeted to IL-17F Epitope1) and Cy(RSYNK) (SEQ ID NO:28) (targeted to IL-17F Epitope2). Cy(RSYNK) (SEQ ID NO:28) was prioritized based on its high affinity for IL-17F.

Example 8. Interleukin 17F (IL17F): Use the Crystal Structure and PCC Assay Data to Estimate the Distance Between the Two Ligands, and Select a Best Linker from that Information FIG. 10 shows sequence similarity of IL-17F and IL-17A. FIG. 11 shows the generation of ligands for IL-17F and IL-17A. Biligand PCCs were made for IL-17F that bound at two distinct epitopes while monoligand PCs were made for IL-17A. FIG. 12A provides the full structure of IL-17F (PDB: $1.11^3$Y). Two PCC-targeted epitopes L1 and L2 are shown to the left of the drawing. These are two epitopes that distinguish IL-17F from IL-17A. Note that these epitopes are not sequence-adjacent, but are proximal within the folded protein structure. FIG. 12B is an expanded view of the targeted region of the protein (from the crystal structure), and the binding locations and sequences of two epitope targeted PCC macrocyclic ligands are drawn. Each of the PCCs exhibit $K_D$ values in the range of 15-70 nM.

The PCCs Cy(RRATS) (SEQ ID NO:9) (targeted to IL-17F Epitope1) and Cy(RSYNK) (SEQ ID NO:28) (targeted to IL-17F Epitope2) were built with chemical handles for further elaboration. Cy(RSYNK) (SEQ ID NO:28) was prioritized based on its high affinity for IL-17F ($K_D$=15 nM). The distance between those chemical handles, when the PCCs are bound to IL-17F, is an estimated 15 Å. This predicts that an optimized linker connecting the two PCCs will have a length near 15 Å. In FIG. 12C that prediction is validated by testing polyethylene glycol (PEG) oligomer-based linkers of varying lengths. When the two PCCs are covalently linked to each other by using the PEG oligomer of length closest to 15 Å, the resultant biligand Cy(RSYNK) (SEQ ID NO:28)-$PEG_3$-Cy(RRATS) (SEQ ID NO:9) exhibits a $K_D$ value of 250 pM against IL-17F. This represents a >100-fold improvement in affinity relative to the individual PCC macrocyclic ligands. Shorter or longer linkers yield biligand affinities that, while improved over either of the monoligands, are about ~10-fold below that of the optimal linker.

Structures of the biligand candidates Biotin-$PEG_3$-Cy (RSYNK) (SEQ ID NO:28)-$PEG_x$-Cy(RRATS) (SEQ ID NO:9) (x=1 to 5) are shown in FIG. 13.

Example 9. Linkage of the Two Ligands Using Best Available Knowledge, Resulting in a Biligand with Improved Affinity Over the Individual Ligands Biligand binders to IL-17F with linkers that are shorter ($PEG_1$, $PEG_2$) or longer ($PEG_4$, $PEG_5$) than 15 Å exhibit $K_D$ values of 1-4 nM against IL-17F. These values represent a 5- to 25-fold improvement in affinity relative to the individual PCC macrocyclic ligands.

*Plasmodium falciparum* Histidine Rich Protein-2 (Pf.HRP-2) is an unstructured protein, but has many epitopes that repeat throughout the structure. A series of PCCs were developed against various Pf.HRP-2 epitopes. The sequence map of Pf.HRP-2 is provided in FIG. 14.

The cyclic peptide, Cy(YKYYR) (SEQ ID NO:29) was developed against the AHHAHHAAD (SEQ ID NO:35) epitope. Cy(YKYYR) (SEQ ID NO:29) exhibits a $EC_{50}$ of 220 nM. Because of the number of epitope repeats, a cooperative binder was sought by simply linking two Cy(YKYYR) (SEQ ID NO:29) PCCs together with about a 1.5 nm long linker. The resultant linked biligand exhibited an $EC_{50}$ of 20 nM (FIG. 15).

The cyclic PCC with variable sequence GWNVDL (SEQ ID NO:30) was developed against the C-terminal sequence of Pf.HRP-2 (AHHATDAHHAAAHHEAATHCL) (SEQ ID NO:36) ($EC_{50}$=50 nM). A linker between this PCC and cyclic YKYYR (SEQ ID NO:29) (see above; $EC_{50}$=220 nM) was developed by screening a 10,000 element library of variable length linker molecules. The resultant biligand exhibited an $EC_{50}$ of 540 pM, which is a 100-fold improvement over the better of the two ligand components (FIG. 16).

What is claimed is:

1. A stable, synthetic capture agent that specifically binds IL-17F, wherein the capture agent comprises a first ligand having binding affinity for a first epitope on an IL-17F, a second ligand having binding affinity for a second epitope on the IL-17F, and a linker covalently connecting the first ligand to the second ligand, wherein the first ligand specifically binds to the first epitope and the second ligand specifically binds to the second epitope, wherein the first epitope comprises the amino acid sequence FFQKPES (SEQ ID NO:1), wherein the first ligand comprises the amino acid sequence FYKTH (SEQ ID NO:5), FYKQH (SEQ ID NO:6), FYLTH (SEQ ID NO:7), FYLQH (SEQ ID NO:8), RRATS (SEQ ID NO:9), or RRAQS (SEQ ID NO:10), wherein the second epitope comprises the amino acid sequence NENQRVS (SEQ ID NO:3), wherein the second ligand comprises the amino acid sequence KYGEV (SEQ ID NO:11), LYGEV (SEQ ID NO:12), VHKSG (SEQ ID NO:13), VHLSG (SEQ ID NO:14), QKHGP (SEQ ID NO:15), TKHGP (SEQ ID NO:16), QLHGP (SEQ ID NO:17), TLHGP (SEQ ID NO:18), YDLQR (SEQ ID NO:19), YDLTR (SEQ ID NO:20), YDKQR (SEQ ID NO:21), YDKTR (SEQ ID NO:22), KKGWP (SEQ ID NO:23), KLGWP (SEQ ID NO:24), LKGWP (SEQ ID NO:25), LLGWP (SEQ ID NO:26), RSYNL (SEQ ID NO:27), and RSYNK (SEQ ID NO:28).

2. The capture agent of claim 1, wherein the capture agent is selective for IL-17F over IL-17A.

3. The capture agent of claim 1, wherein the first epitope comprises the amino acid sequence FFQKPESCPPVPGG (SEQ ID NO:2).

4. The capture agent of claim 1, wherein the second epitope comprises the amino acid sequence GIINENQRVS (SEQ ID NO:4).

5. The capture agent of claim 1, wherein the first ligand comprises the amino acid sequence RRATS (SEQ ID NO:9) or RRAQS (SEQ ID NO:10).

6. The capture agent of claim 1, wherein the first ligand comprises the sequence RRATS (SEQ ID NO:9).

7. The capture agent of claim 1, wherein the first ligand comprises the sequence RRAQS (SEQ ID NO:10).

8. The capture agent of claim 1, wherein the first ligand is cyclic.

9. The capture agent of claim 1, wherein the first ligand comprises a 1,4-substituted-1,2,3-triazole residue (Tz4) or a 1,5-substituted-1,2,3-triazole residue (Tz5).

10. The capture agent of claim 9, wherein the triazole residue is a 1,4-substituted-1,2,3-triazole (Tz4) residue.

11. The capture agent of claim 1, wherein the second ligand comprises the amino acid sequence TKHGP (SEQ ID NO:16), QKHGP (SEQ ID NO:15), KKGWP (SEQ ID NO:23), or RSYNK (SEQ ID NO:28).

12. The capture agent of claim 1, wherein the second ligand comprises the amino acid sequence TKHGP (SEQ ID NO:16).

13. The capture agent of claim 1, wherein the second ligand comprises the amino acid sequence QKHGP (SEQ ID NO:15).

14. The capture agent of claim 1, wherein the second ligand comprises the amino acid sequence KKGWP (SEQ ID NO:23).

15. The capture agent of claim 1, wherein the second ligand comprises the amino acid sequence RSYNK (SEQ ID NO:28).

16. The capture agent of claim 1, wherein the second ligand is cyclic.

17. The capture agent of claim 1, wherein the second ligand comprises a 1,4-substituted-1,2,3-triazole residue (Tz4) or a 1,5-substituted-1,2,3-triazole residue (Tz5).

18. The capture agent of claim 17, wherein the triazole residue is a 1,4-substituted-1,2,3-triazole residue (Tz4).

19. The capture agent of claim 1, wherein the linker is divalent.

20. The capture agent of claim 1, wherein the length of the linker corresponds to distance between the first epitope and the second epitope.

21. The capture agent of claim 20, wherein the length of the linker is from ~4.4 Å to ~26.4 Å, from ~8.8 Å to ~26.4 Å or from ~7 Å to ~15 Å.

22. The capture agent of claim 20, wherein the length of the linker is ~15 Å.

23. The capture agent of claim 1, wherein the linker comprises one or more repeat units of ethylene glycol.

24. The capture agent of claim 1, wherein the linker comprises a peptide.

25. The capture agent of claim 1, wherein the first ligand comprises the sequence RRATS (SEQ ID NO:9) and the second ligand comprises the sequence QKHGP (SEQ ID NO:15).

26. The capture agent of claim 1, wherein the first ligand comprises the sequence RRATS (SEQ ID NO:9) and the second ligand comprises the sequence RSYNK (SEQ ID NO:28).

27. The capture agent of claim 26, wherein the first and second ligands are cyclic and comprise a Tz4 residue.

28. The capture agent of claim 27, wherein the linker is glycine.

29. The capture agent of claim 27, wherein the linker is $PEG_1$.

30. The capture agent of claim 27, wherein the linker is $PEG_2$.

31. The capture agent of claim 27, wherein the linker is $PEG_3$.

32. The capture agent of claim 27, wherein the linker is $PEG_4$.

33. The capture agent of claim 27, wherein the linker is $PEG_5$.

34. The capture agent of claim 1, wherein the capture agent is labeled with a detectable moiety.

35. The capture agent of claim 34, wherein the detectable moiety is selected from the group consisting of biotin, copper-DOTA, biotin-PEG3, aminooxyacetate, $^{19}$FB, $^{18}$FB and FITC-$PEG_3$.

36. The capture agent of claim 34, wherein the detectable moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $^{11}$C and $^{76}$Br.

37. A stable, synthetic capture agent that specifically binds IL-17F having a structure selected from the group consisting of:

a.
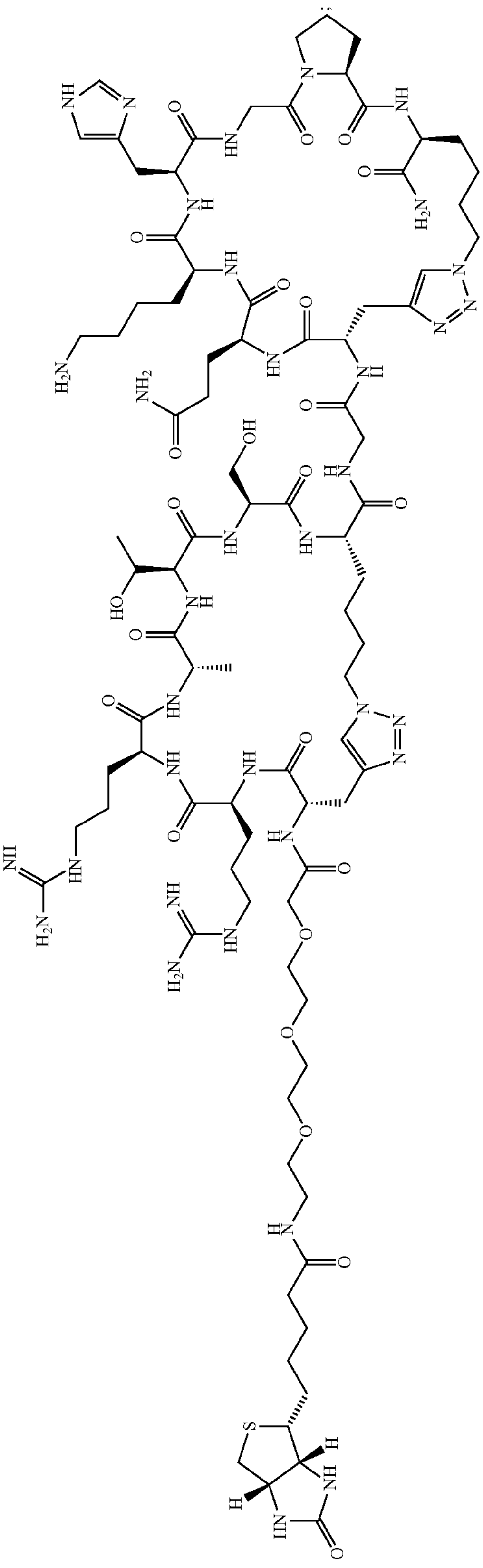
Chemical Formula: $C_{88}H_{143}N_{35}O_{24}S$
Exact Mass: 2106.08
Molecular Weight: 2107.36

-continued
b.
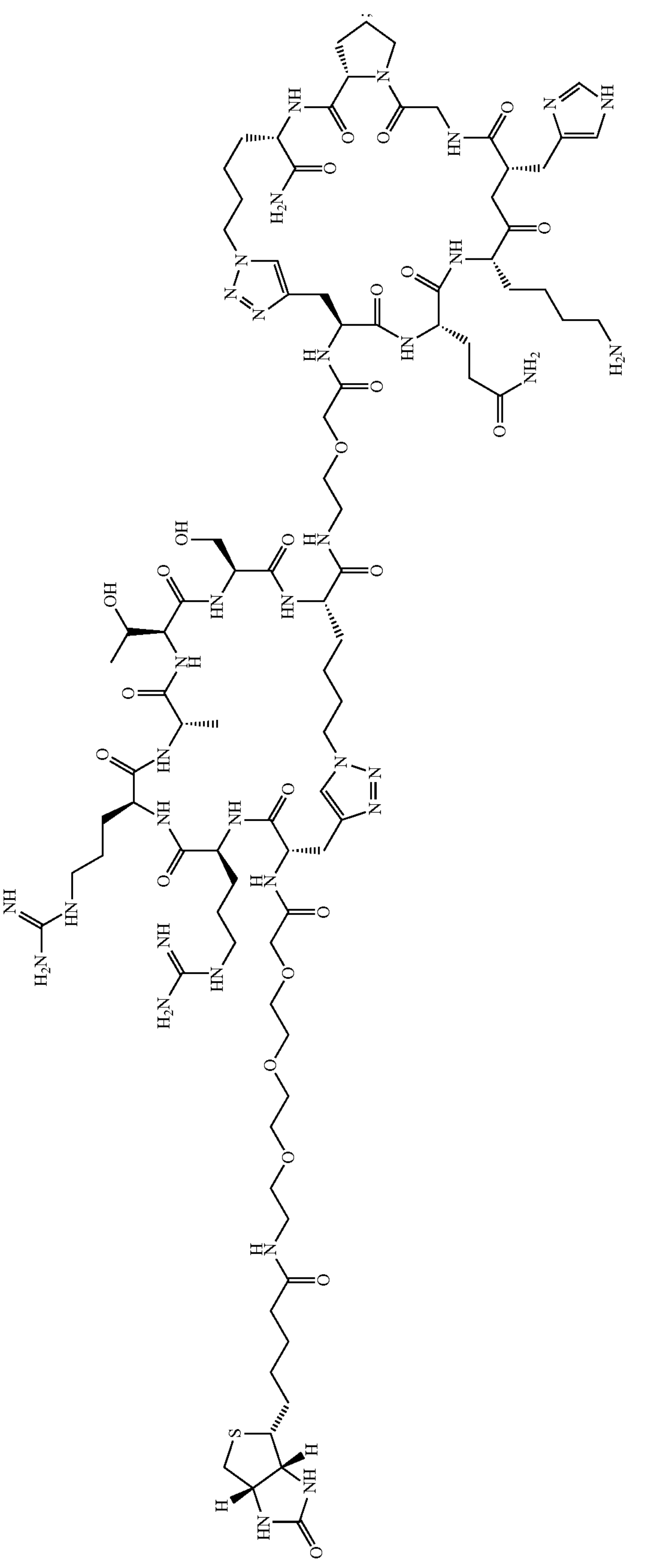
Chemical Formula: $C_{90}H_{147}N_{35}O_{25}S$
Exact Mass: 2150.10
Molecular Weight: 2151.41

-continued
c.
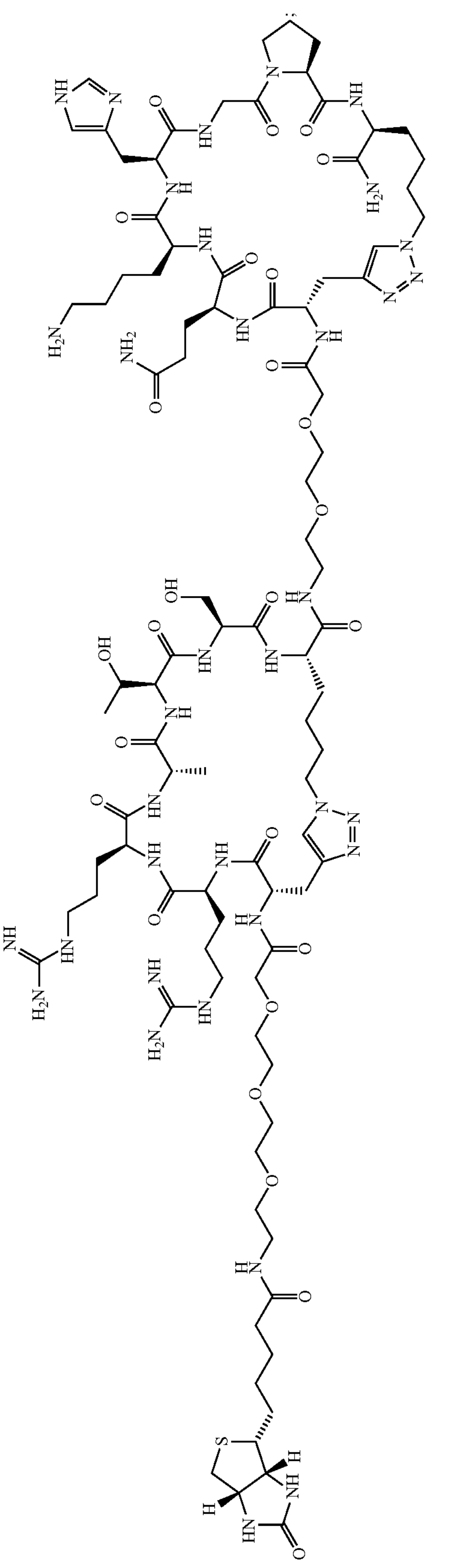
Chemical Formula: $C_{92}H_{151}N_{35}O_{26}S$
Exact Mass: 2194.13
Molecular Weight: 2195.47

-continued
d.
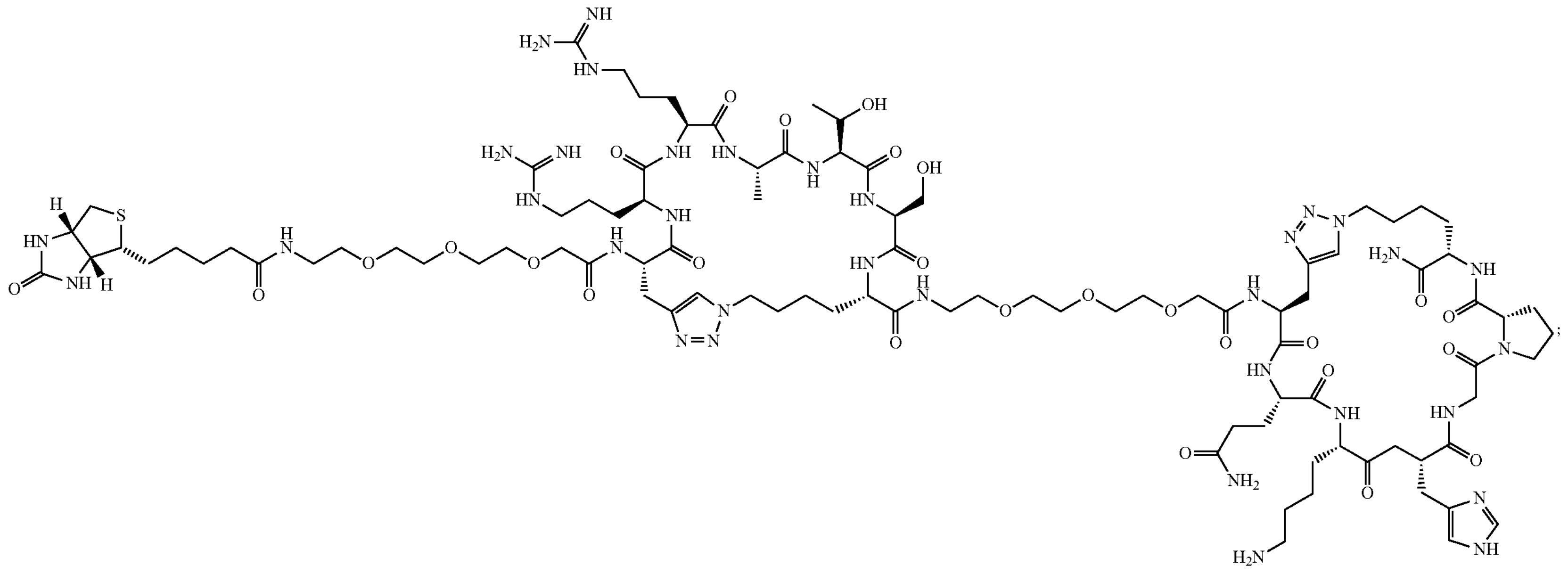
Chemical Formula: $C_{94}H_{155}N_{35}O_{27}S$
Exact Mass: 2238.16
Molecular Weight: 2239.52

-continued
e.
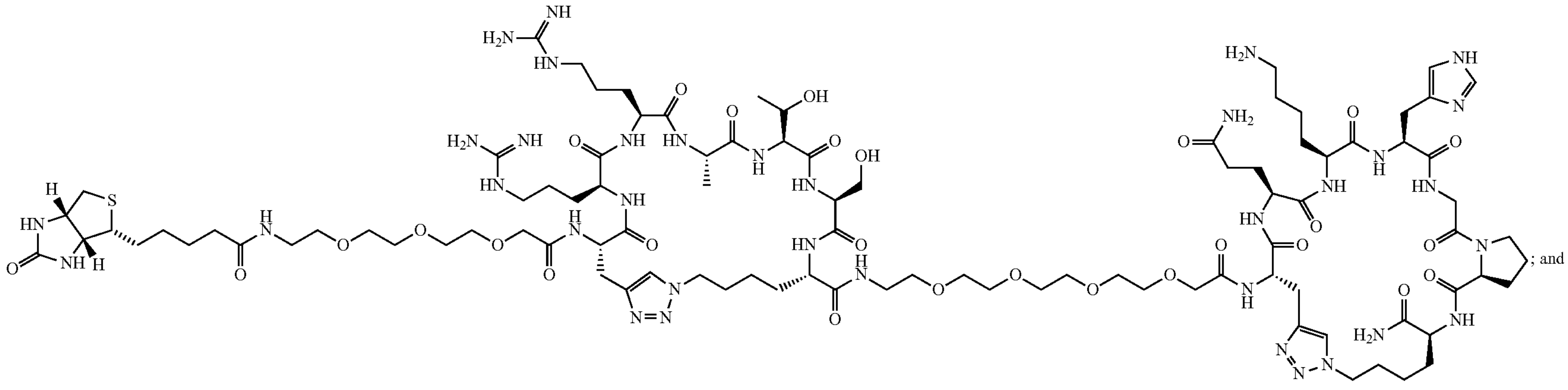
; and
Chemical Formula: $C_{96}H_{159}N_{35}O_{28}S$
Exact Mass: 2282.18
Molecular Weight: 2283.57

-continued
f
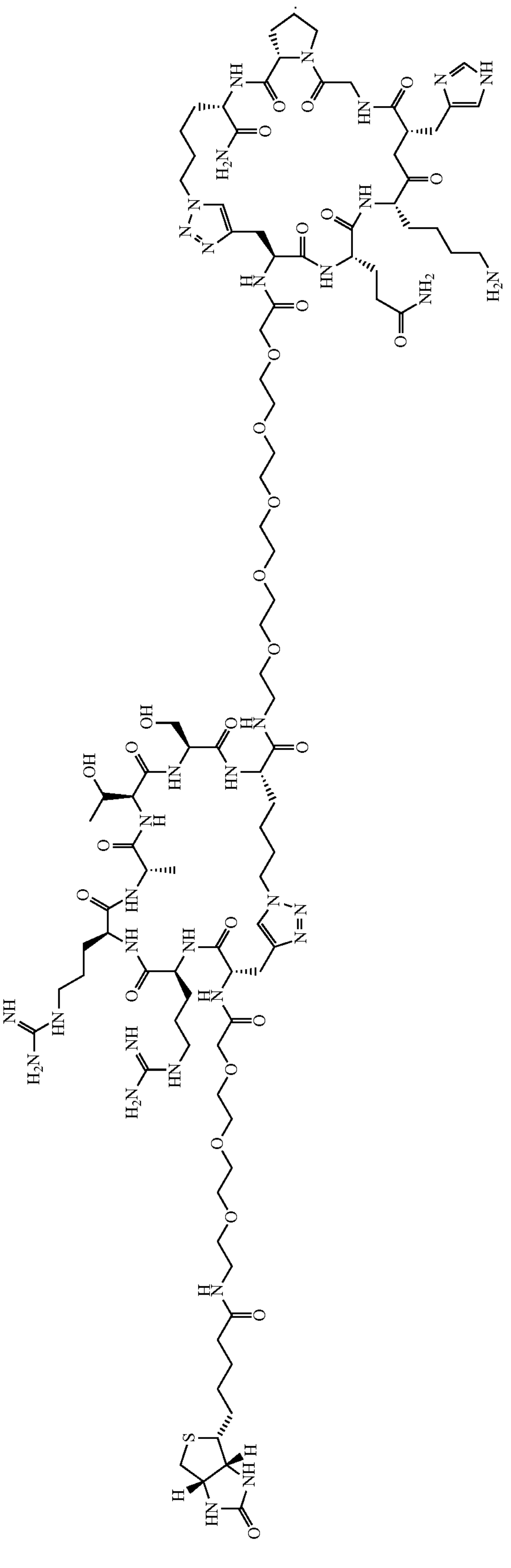
Chemical Formula: $C_{98}H_{163}N_{35}O_{29}S$
Exact Mass: 2326.21
Molecular Weight: 2327.62

38. A stable, synthetic capture agent that specifically binds IL-17F having a structure selected from the group consisting of:

a.
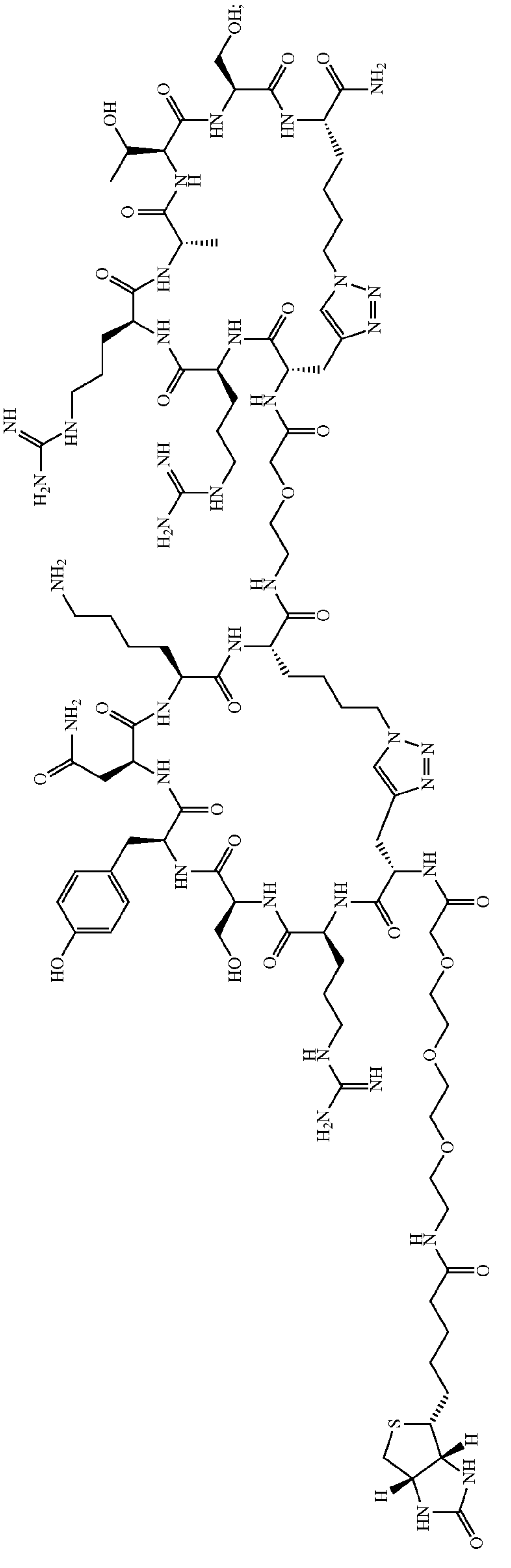
Chemical Formula: $C_{94}H_{154}N_{36}O_{27}S$
Exact Mass: 2251.15
Molecular Weight: 2252.52

-continued
b.
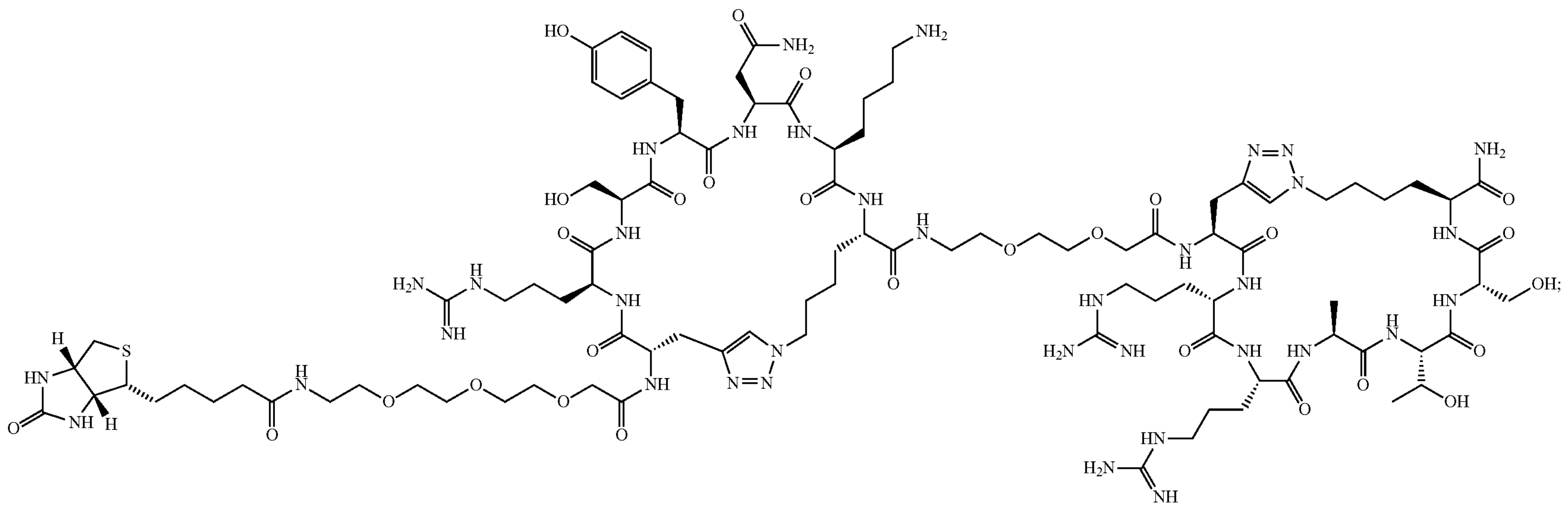
Chemical Formula: $C_{96}H_{158}N_{36}O_{28}S$
Exact Mass: 2295.18
Molecular Weight: 2296.57

-continued
c.
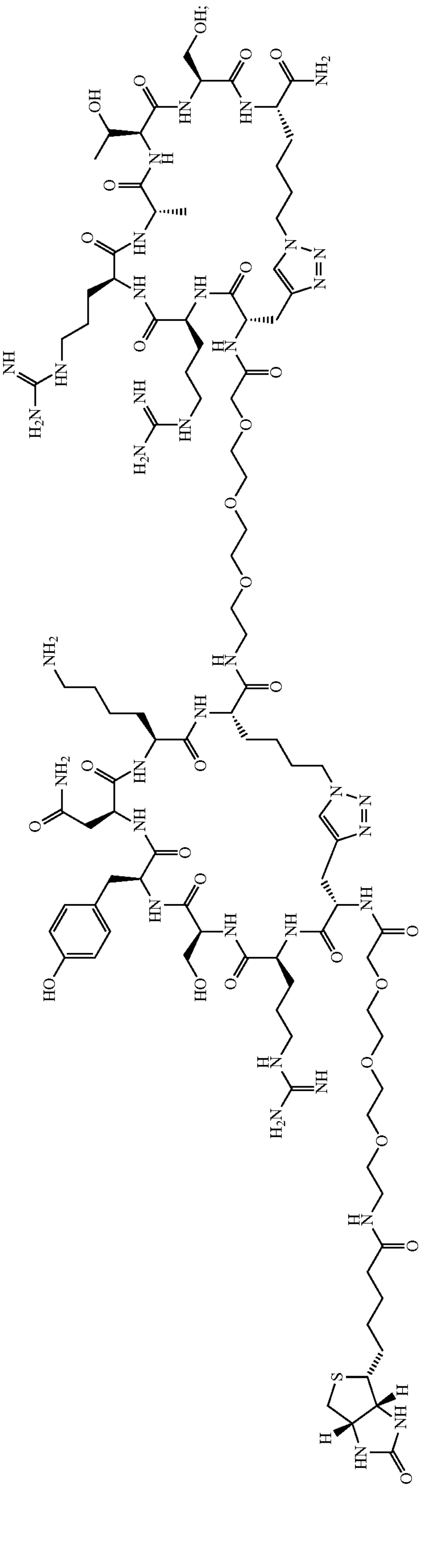
Chemical Formula: $C_{98}H_{162}N_{36}O_{29}S$
Exact Mass: 2339.20
Molecular Weight: 2340.62

-continued
d.
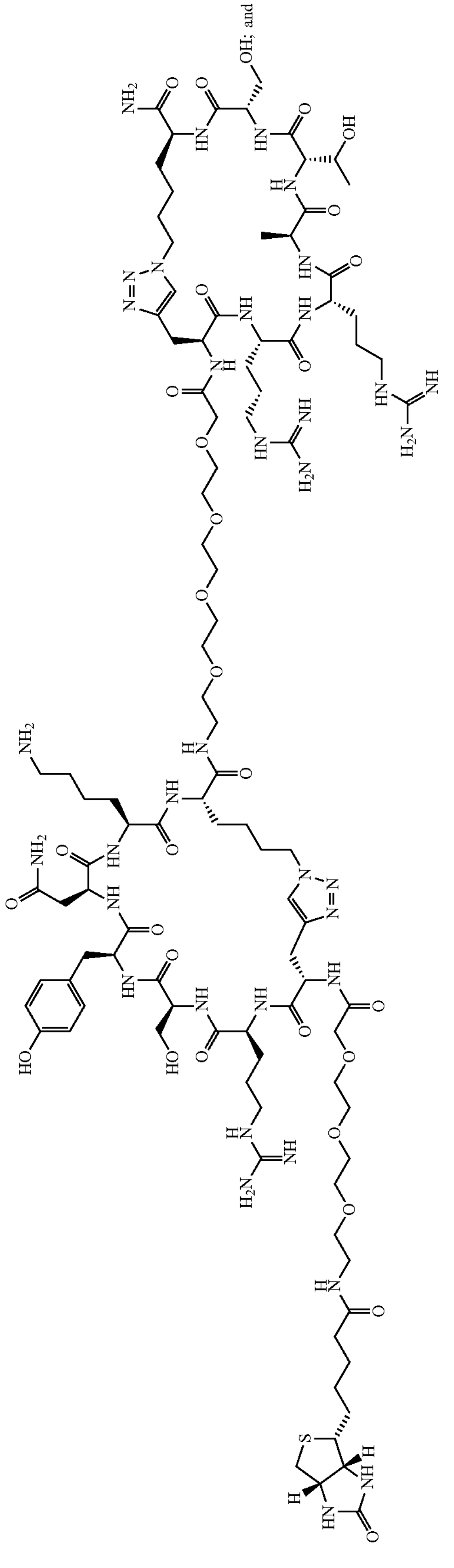
; and
Chemical Formula: $C_{100}H_{166}N_{36}O_{30}S$
Exact Mass: 2383.23
Molecular Weight: 2384.68

-continued
e.
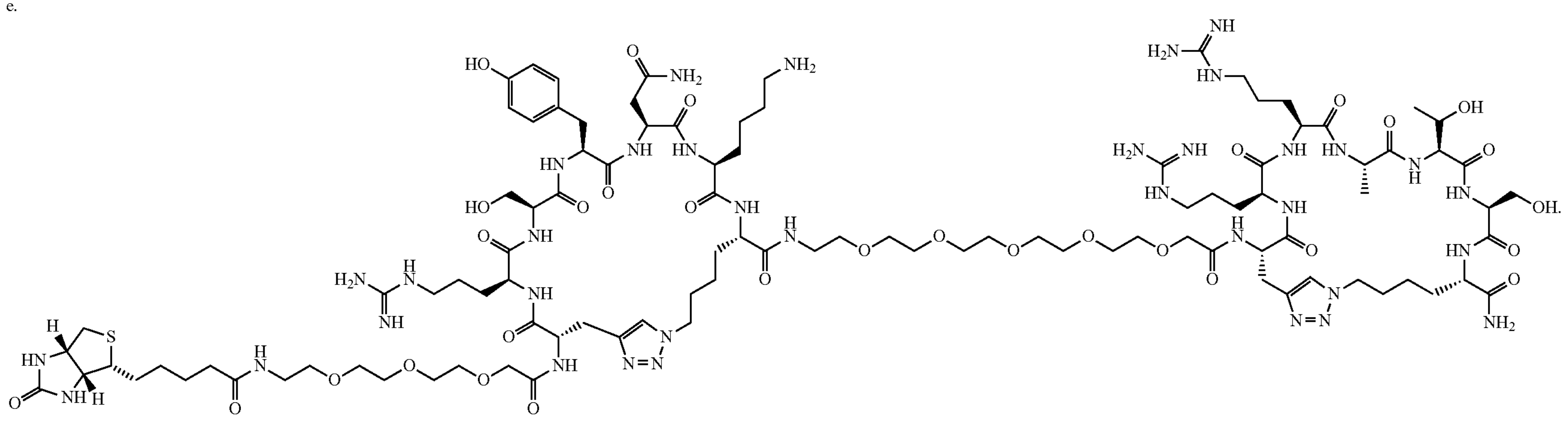
Chemical Formula: $C_{102}H_{170}N_{36}O_{31}S$
Exact Mass: 2427.26
Molecular Weight: 2428.73

39. A method of detecting IL-17F in a biological sample, comprising the steps of contacting the biological sample with one or more of the capture agents of claim 1 under conditions allowing binding of the capture agents to IL-17F present in the sample to form a complex, and detecting the complex to detect IL-17F in the biological sample.

40. The capture agent of claim 1, wherein the length of the linker corresponds to distance between the first epitope and the second epitope, wherein the linker comprises one or more repeat units of ethylene glycol, a peptide, or both.

41. The capture agent of claim 40, wherein the length of the linker is from ~4.4 Å to ~26.4 Å, from ~8.8 Å to ~26.4 Å or from ~7 Å to ~15 Å.

42. The capture agent of claim 40, wherein the length of the linker is ~15 Å.

43. The capture agent of claim 40, wherein the linker is glycine.

44. The capture agent of claim 40, wherein the linker is $PEG_1$.

45. The capture agent of claim 40, wherein the linker is $PEG_2$.

46. The capture agent of claim 40, wherein the linker is $PEG_3$.

47. The capture agent of claim 40, wherein the linker is $PEG_4$.

48. The capture agent of claim 40, wherein the linker is $PEG_5$.

49. The capture agent of claim 40, wherein the first and second ligands are cyclic and comprise a 1,4-substituted-1,2,3-triazole residue (Tz4) or a 1,5-substituted-1,2,3-triazole residue (Tz5).

50. A stable, synthetic capture agent that specifically binds IL-17F, wherein the capture agent comprises a first ligand having binding affinity for a first epitope on an IL-17F, a second ligand having binding affinity for a second epitope on the IL-17F, and a linker covalently connecting the first ligand to the second ligand, wherein the first ligand comprises the sequence RRATS (SEQ ID NO:9) and the second ligand comprises the sequence RSYNK (SEQ ID NO:28), wherein the first and second ligands are cyclic and comprise a Tz4 residue, wherein the linker is glycine, $PEG_1$, $PEG_2$, $PEG_3$, $PEG_4$, or $PEG_5$.

* * * * *

UNITED STATES PATENT AND TRADEMARK OFFICE

CERTIFICATE OF CORRECTION

PATENT NO. : 10,598,671 B2
APPLICATION NO. : 15/211759
DATED : March 24, 2020
INVENTOR(S) : James R. Heath et al.

It is certified that error appears in the above-identified patent and that said Letters Patent is hereby corrected as shown below:

In the Specification

Column 1, Line 12, insert:
--STATEMENT REGARDING FEDERALLY SPONSORED RESEARCH OR DEVELOPMENT
This invention was made with government support under Grant No. W911NF-09-D-0001 awarded by the U.S. Army Research Office. The government has certain rights in the invention.--

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*